United States Patent
Jakobsen

(10) Patent No.: US 9,115,372 B2
(45) Date of Patent: Aug. 25, 2015

(54) CELLS EXPRESSING MODIFIED T CELL RECEPTOR

(71) Applicant: Immunocore Ltd., Abingdon, Oxfordshire (GB)

(72) Inventor: Bent Karsten Jakobsen, Abingdon (GB)

(73) Assignees: IMMUNOCORE LIMITED, Abingdon, Oxon (GB); ADAPTIMMUNE LIMITED, Oxford (GB)

(*) Notice: Subject to any disclaimer, the term of this patent is extended or adjusted under 35 U.S.C. 154(b) by 273 days.

(21) Appl. No.: 13/716,817

(22) Filed: Dec. 17, 2012

(65) Prior Publication Data

US 2013/0189309 A1    Jul. 25, 2013

Related U.S. Application Data

(62) Division of application No. 11/597,252, filed as application No. PCT/GB2005/002570 on Jun. 29, 2005, now Pat. No. 8,361,794.

(51) Int. Cl.
  *C12N 15/85* (2006.01)
  *A61K 35/17* (2015.01)
  *C12N 5/0783* (2010.01)
  *C07K 14/725* (2006.01)

(52) U.S. Cl.
  CPC .............. *C12N 15/85* (2013.01); *A61K 35/17* (2013.01); *C07K 14/7051* (2013.01); *C12N 5/0636* (2013.01); *C12N 2510/00* (2013.01)

(58) Field of Classification Search
  CPC .. C12N 15/85; C12N 5/0636; C12N 2510/00; A61K 35/17; C07K 14/7051
  See application file for complete search history.

(56) References Cited

U.S. PATENT DOCUMENTS 6,558,672 B1   5/2003   Pastan et al.

FOREIGN PATENT DOCUMENTS

| WO | WO 01/55366 A | 8/2001 |
| WO | WO 03/020763 A | 3/2003 |
| WO | WO 2004/033685 | 4/2004 |
| WO | WO 2004/074322 A | 9/2004 |

OTHER PUBLICATIONS

F. Pecorari, et al., Folding, Heterodimeric Association and Specific Peptide Recognition of a Murine Alphabeta T-Cell Receptor Expressed in *Escherichia coli*, Journal of Molecular Biology, London, GB, vol. 285, No. 4, Jan. 29, 1999, p. 1831-1843.

Z.G. Li, et al., Structural Mutations in the Constant Region of the T-Cell Antigen Receptor (TCR) Beta Chain and Their Effect on TCR Alpha and Beta Chain Interaction, Immunology, Blackwell Publishing, Oxford, GB, vol. 88, No. 4, Aug. 1996, p. 524-530.

Y. Reiter, et al., Construction of a functional disulfide-stabilized TCR FV indicates that antibody and TCR FV frameworks are very similar in structure, Immunity, Cell Press, US, vol. 2, No. 3, Mar. 1995, p. 281-287.

*Primary Examiner* — Taeyoon Kim
(74) *Attorney, Agent, or Firm* — Vedder Price P.C.; Thomas J. Kowalski; Deborah L. Lu

(57) ABSTRACT

This invention provides a cell presenting at least one T cell receptor (TCR) anchored to the membrane by a transmembrane sequence, said TCR comprising an interchain disulfide bond between extracellular constant domain residues which is not present in native TCRs.

20 Claims, 27 Drawing Sheets

Figure 1
TCR α Chain
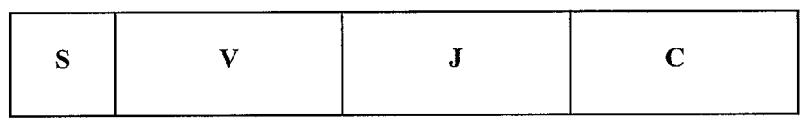
TCR β Chain
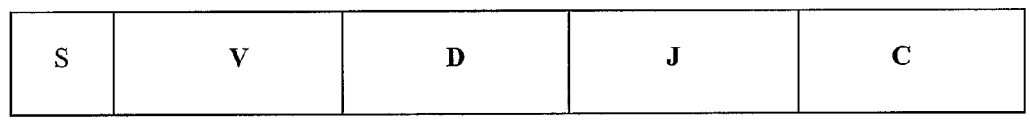

Figure 3a atgcagaaggaagtggagcagaactctggacccctcagtgttccagagggagccattg
cctctctcaactgcacttacagtgaccgaggttcccagtccttcttctggtacagaca
atattctgggaaaagccctgagttgataatgtccatatactccaatggtgacaaagaa
gatggaaggtttacagcacagctcaataaagccagccagtatgtttctctgctcatca
gagactcccagcccagtgattcagccacctacctctgtgccgttacaactgacagctg
ggggaaattgcagtttggagcagggacccaggttgtggtcacccagatatccagaac
cctgaccctgccgtgtaccagctgagagactctaaatccagtgacaagtctgtctgcc
tattcaccgattttgattctcaaacaaatgtgtcacaaagtaaggattctgatgtgta
tatcacagacaaatgtgtgctagacatgaggtctatggacttcaagagcaacagtgct
gtggcctggagcaacaaatctgactttgcatgtgcaaacgccttcaacaacagcatta
ttccagaagacaccttcttccccagcccagaaagttcctaa

Figure 3b atgaacgctggtgtcactcagaccccaaaattccaggtcctgaagacaggacagagca
tgacactgcagtgtgcccaggatatgaaccatgaatacatgtcctggtatcgacaaga
cccaggcatggggctgaggctgattcattactcagttggtgctggtatcactgaccaa
ggagaagtccccaatggctacaatgtctccagatcaaccacagaggatttcccgctca
ggctgctgtcggctgctcctcccagacatctgtgtacttctgtgccagcaggccggg
actagcgggagggcgaccagagcagtacttcgggccgggcaccaggctcacggtcaca
gaggacctgaaaaacgtgttcccacccgaggtcgctgtgtttgagccatcagaagcag
agatctcccacacccaaaaggccacactggtgtgcctggccacaggcttctaccccga
ccacgtggagctgagctggtgggtgaatgggaaggaggtgcacagtggggtctgcaca
gacccgcagcccctcaaggagcagcccgccctcaatgactccagatacgctctgagca
gccgcctgagggtctcggccaccttctggcaggaccccgcaaccacttccgctgtca
agtccagttctacgggctctcggagaatgacgagtggacccaggatagggccaaaccc
gtcacccagatcgtcagcgccgaggcctggggtagagcagactaa

Figure 4a

```
MQ
KEVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QTNVSQSKDS
DVYITDKCVL DMRSMDFKSN SAVAWSNKSD FACANAFNNS IIPEDTFFPS
PESS*
```

Figure 4b

```
M
NAGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VCTDPQPLKE QPALNDSRYA LSSRLRVSAT
FWQDPRNHFR CQVQFYGLSE NDEWTQDRAK PVTQIVSAEA WGRAD*
```

Figure 5
5a
Full length A6 Tax TCR cDNA
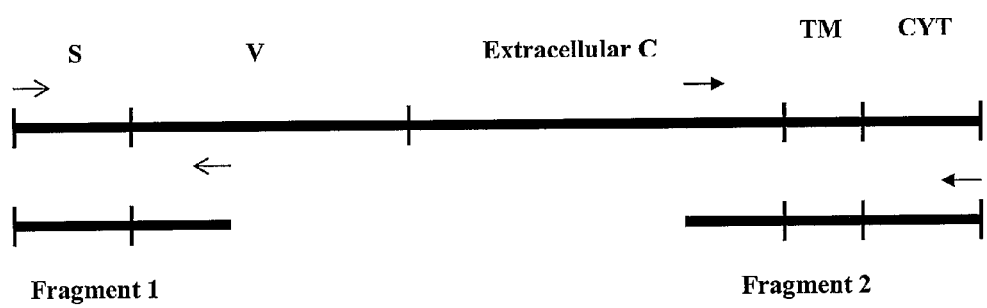
Fragment 1          Fragment 2
5b
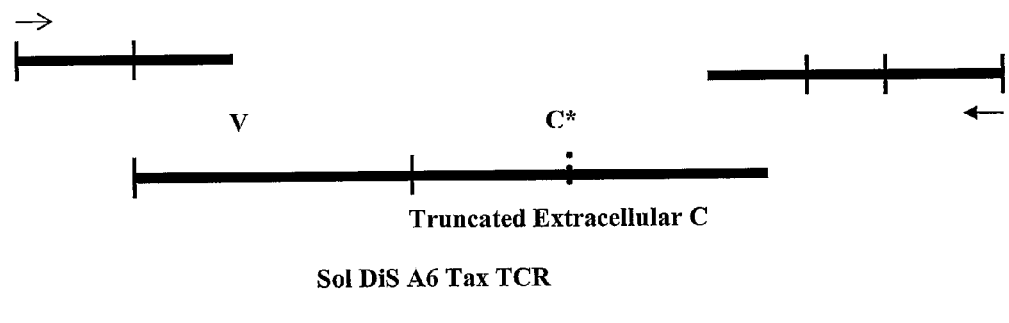
Sol DiS A6 Tax TCR
5c
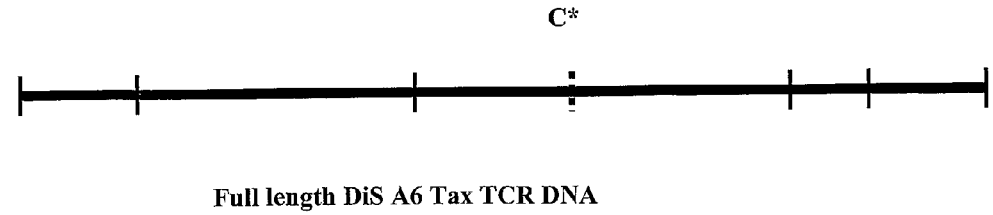
Full length DiS A6 Tax TCR DNA

Figure 6a

```
        M   M   K   S   L   R   V   L   L   V   I   L   W   L   Q   L   S   W   V   W
  1   ATGATGAAAT CCTTGAGAGT TTTACTAGTG ATCCTGTGGC TTCAGTTGAG CTGGGTTTGG
        S   Q   Q   K   E   V   E   Q   N   S   G   P   L   S   V   P   E   G   A   I
 61   AGCCAACAGA AGGAAGTGGA GCAGAACTCT GGACCCCTCA GTGTTCCAGA GGGAGCCATT
        A   S   L   N   C   T   Y   S   D   R   G   S   Q   S   F   F   W   Y   R   Q
121   GCCTCTCTCA ACTGCACTTA CAGTGACCGA GGTTCCCAGT CCTTCTTCTG GTACAGACAA
        Y   S   G   K   S   P   E   L   I   M   S   I   Y   N   G   D   K   E   D
181   TATTCTGGGA AAAGCCCTGA GTTGATAATG TCCATATACT CCAATGGTGA CAAAGAAGAT
        G   R   F   T   A   Q   L   N   K   A   S   Q   Y   V   S   L   L   I   R   D
241   GGAAGGTTTA CAGCACAGCT CAATAAAGCC AGCCAGTATG TTTCTCTGCT CATCAGAGAC
        S   Q   P   S   D   S   A   T   Y   L   C   A   V   T   D   S   W   G   K
301   TCCCAGCCCA GTGATTCAGC CACCTACCTC TGTGCCGTTA CAACTGACAG CTGGGGGAAA
        L   Q   F   G   A   G   T   Q   V   V   V   T   P   D   I   Q   N   P   D   P
361   TTGCAGTTTG GAGCAGGGAC CCAGGTTGTG GTCACCCCAG ATATCCAGAA CCCTGACCCT
        A   V   Y   Q   L   R   D   S   K   S   S   D   K   S   V   C   L   F   T   D
421   GCCGTGTACC AGCTGAGAGA CTCTAAATCC AGTGACAAGT CTGTCTGCCT ATTCACCGAT
        F   D   S   Q   T   N   V   S   Q   S   K   D   S   D   V   Y   I   T   D   K
481   TTTGATTCTC AAACAAATGT GTCACAAAGT AAGGATTCTG ATGTGTATAT CACAGACAAA
        C   V   L   D   M   R   S   M   D   F   K   S   N   S   A   V   A   W   S   N
541   TGTGTGCTAG ACATGAGGTC TATGGACTTC AAGAGCAACA GTGCTGTGGC CTGGAGCAAC
        K   S   D   F   A   C   A   N   A   F   N   N   S   I   I   P   E   D   T   F
601   AAATCTGACT TTGCATGTGC AAACGCCTTC AACAACAGCA TTATTCCAGA AGACACCTTC
        F   P   S   P   E   S   S   S   D   V   K   L   V   E   K   S   F   E   T   D
661   TTCCCCAGCC CAGAAAGTTC CTCTGATGTC AAGCTGGTCG AGAAAAGCTT TGAAACAGAT
        T   N   L   N   F   Q   N   L   S   V   I   G   F   R   I   L   L   K   V
721   ACGAACCTAA ACTTTCAAAA CCTGTCAGTG ATTGGGTTCC GAATCCTCCT CCTGAAAGTG
        A   G   F   N   L   L   M   T   L   R   L   W   S   S   *
781   GCCGGGTTTA ATCTGCTCAT GACGCTGCGG CTGTGGTCCA GCTAA
```

Figure 6b

```
              M   S   I   G   L   L   C     C   A   A     L   S   L   L     W   A   G     P   V   N
  1    ATGAGCATCG GCCTCCTGTG CTGTGCAGCC TTGTCTCTCC TGTGGGCAGG TCCAGTGAAC
         A   G   V   T     Q   T   P     K   F   Q     V   L   K   T     G   Q   S     M   T   L
 61    GCTGGTGTCA CTCAGACCCC AAAATTCCAG GTCCTGAAGA CAGGACAGAG CATGACACTG
         Q   C   A   Q     D   M   N     H   E   Y     M   S   W   Y     R   Q   D     P   G   M
121    CAGTGTGCCC AGGATATGAA CCATGAATAC ATGTCCTGGT ATCGACAAGA CCCAGGCATG
         G   L   R   L     I   H   Y     S   V   G     A   G   I   T     D   Q   G     E   V   P
181    GGGCTGAGGC TGATTCATTA CTCAGTTGGT GCTGGTATCA CTGACCAAGG AGAAGTCCCC
         N   G   Y   N     V   S   R     S   T   T     E   D   F   P     L   R   L     L   S   A
241    AATGGCTACA ATGTCTCCAG ATCAACCACA GAGGATTTCC CGCTCAGGCT GCTGTCGGCT
         A   P   S   Q     T   S   V     Y   F   C     A   S   R   P     G   L   A     G   G   R
301    GCTCCCTCCC AGACATCTGT GTACTTCTGT GCCAGCAGGC CGGGACTAGC GGGAGGGCGA
         P   E   Q   Y     F   G   P     G   T   R     L   T   V   T     E   D   L     K   N   V
361    CCAGAGCAGT ACTTCGGGCC GGGCACCAGG CTCACGGTCA CAGAGGACCT GAAAAACGTG
         F   P   P   E     V   A   V     F   E   P     S   E   A   E     I   S   H     T   Q   K
421    TTCCCACCCG AGGTCGCTGT GTTTGAGCCA TCAGAAGCAG AGATCTCCCA CACCCAAAAG
         A   T   L   V     C   L   A     T   G   F     Y   P   D   H     V   E   L     S   W   W
481    GCCACACTGG TGTGCCTGGC CACAGGCTTC TACCCCGACC ACGTGGAGCT GAGCTGGTGG
         V   N   G   K     E   V   H     S   G   V     C   T   D   P     Q   P   L     K   E   Q
541    GTGAATGGGA AGGAGGTGCA CAGTGGGGTC TGCACAGACC CGCAGCCCCT CAAGGAGCAG
         P   A   L   N     D   S   R     Y   C   L     S   S   R   L     R   V   S     A   T   F
601    CCCGCCCTCA ATGACTCCAG ATACTGCCTG AGCAGCCGCC TGAGGGTCTC GGCCACCTTC
         W   Q   D   P     R   N   H     F   R   C     Q   V   Q   F     Y   G   L     S   E   N
661    TGGCAGGACC CCCGCAACCA CTTCCGCTGT CAAGTCCAGT TCTACGGGCT CTCGGAGAAT
         D   E   W   T     Q   D   R     A   K   P     V   T   Q   I     V   S   A     E   A   W
721    GACGAGTGGA CCCAGGATAG GGCCAAACCC GTCACCCAGA TCGTCAGCGC CGAGGCCTGG
         G   R   A   D     S   G   F     T   S   E     S   Y   Q   Q     G   V   L     S   A   T
781    GGTAGAGCAG ACTCTGGCTT CACCTCCGAG TCTTACCAGC AAGGGGTCCT GTCTGCCACC
         I   L   Y   E     I   L   L     G   K   A     T   L   Y   A     V   L   V     S   A   L
841    ATCCTCTATG AGATCTTGCT AGGGAAGGCC ACCTTGTATG CCGTGCTGGT CAGTGCCCTC
         V   L   M   A     M   V   K     R   K   D     S   R   G   *
901    GTGCTGATGG CCATGGTAAA GAGAAAGGAT TCCAGAGGCT AA
```

Figure 7a

TRAC:
aatatccagaaccctgaccctgccgtgtaccagctgagagactctaaatccagtgacaagtctgtctgcctattcaccgattttgattctca
aacaaatgtgtcacaaagtaaggattctgatgtgtatatcacagacaaaactgtgctagacatgaggtctatggacttcaagagcaacag
tgctgtggcctggagcaacaaatctgactttgcatgtgcaaacgccttcaacaacagcattattccagaagacaccttcttccccagccc
agaaagttcctgtgatgtcaagctggtcgagaaaagctttgaaacagatacgaacctaaacttcaaaacctgtcagtgattgggttccg
aatcctcctcctgaaagtggccgggtttaatctgctcatgacgctgcggctgtggtccagctga TRAV1-1:
atgtggggagctttccttctctatgtttccatgaagatgggaggcactgcaggacaaagccttgagcagccctctgaagtgacagctgt
ggaaggagccattgtccagataaactgcacgtaccagacatctgggtttatgggctgtcctggtaccagcaacatgatggcggagca
cccacatttctttcttacaatgctctggatggtttggaggagacaggtcgttttcttcattccttagtcgctctgatagttatggttacctcctt
ctacaggagctccagatgaaagactctgcctcttacttctgcgctgtgagaga TRAV1-2:
atgtggggagttttccttctttatgtttccatgaagatgggaggcactacaggacaaaacattgaccagcccactgagatgacagctacg
gaaggtgccattgtccagatcaactgcacgtaccagacatctgggttcaacgggctgttctggtaccagcaacatgctggcgaagcac
ccacatttctgtcttacaatgttctggatggtttggaggagaaaggtcgtttttcttcattccttagtcggtctaaagggtacagttacctcctt
ttgaaggagctccagatgaaagactctgcctcttacctctgtgctgtgagaga TRAV2:
atggctttgcagagcactctgggggcggtgtggctagggcttctcctcaactctctctggaaggttgcagaaagcaaggaccaagtgtt
tcagccttccacagtggcatcttcagagggagctgtggtggaaatcttctgtaatcactctgtgtccaatgcttacaacttcttctggtacct
tcacttcccgggatgtgcaccaagactccttgttaaaggctcaaagccttctcagcagggacgatacaacatgacctatgaacggttctc
ttcatcgctgctcatcctccaggtgcgggaggcagatgctgctgtttactactgtgctgtggagga TRAV3:
Atggcctctgcacccatctcgatgcttgcgatgctcttcacattgagtgggctgagagctcagtcagtggctcagccggaagatcaggt
caacgttgctgaagggaatcctctgactgtgaaatgcacctattcagtctctggaaacccttatcttttttggtatgttcaataccccaaccg
aggcctccagttccttctgaaatacatcacaggggataaacctggttaaaggcagctatggctttgaagctgaatttaacaagagccaaac
ctccttccacctgaagaaaccatctgcccttgtgagcgactccgctttgtacttctgtgctgtgagagaca TRAV4:
atgaggcaagtggcgagagtgatcgtgttcctgaccctgagtactttgagccttgctaagaccacccagcccatctccatggactcatat
gaaggacaagaagtgaacataacctgtagccacaacaacattgctacaaatgattatatcacgtggtaccaacagtttcccagccaag
gaccacgatttattattcaaggatacaagacaaaagttacaaacgaagtggcctccctgtttatccctgccgacagaaagtccagcactc
tgagcctgccccgggtttccctgagcgacactgctgtgtactactgcctcgtgggtgaca

Figure 7b

TRAV5:
atgaagacatttgctggattttcgttcctgttttgtggctgcagctggactgtatgagtagaggagaggatgtggagcagagtcttttcct
gagtgtccgagagggagacagctccgttataaactgcacttacacagacagctcctccacctacttatactggtataagcaagaacctg
gagcaggtctccagttgctgacgtatattttcaaatatggacatgaaacaagaccaaagactcactgttctattgaataaaaaggataa
acatctgtctctgcgcattgcagacacccagactggggactcagctatctacttctgtgcagagagta TRAV6:
atggagtcattcctgggaggtgttttgctgattttgtggcttcaagtggactgggtgaagagccaaaagatagaacagaattccgaggcc
ctgaacattcaggagggtaaaacggccaccctgacctgcaactatacaaactattcccagcatacttacagtggtaccgacaagatcc
aggaagaggccctgttttcttgctactcatacgtgaaaatgagaaagaaaaaaggaaagaaagactgaaggtcacctttgataccacc
cttaaacagagtttgtttcatatcacagcctcccagcctgcagactcagctacctacctctgtgctctagaca TRAV7:
atggagaagatgcggagacctgtcctaattatattttgtctatgtcttggctgggcaaatggagaaaaccaggtggagcacagccctcat
tttctgggaccccagcagggagacgttgcctccatgagctgcacgtactctgtcagtcgttttaacaatttgcagtggtacaggcaaaat
acagggatgggtcccaaacacctattatccatgtattcagctggatatgagaagcagaaaggaagactaaatgctacattactgaagaa
tggaagcagcttgtacattacagccgtgcagcctgaagattcagccacctatttctgtgctgtagatg TRAV8-1:
atgctcctgttgctcataccagtgctggggatgattttttgccctgagagatgccagagcccagtctgtgagccagcataaccaccacgta
attctctctgaagcagcctcactggagttgggatgcaactattcctatggtggaactgttaatctcttctggtatgtccagtaccctggtcaa
caccttcagcttctcctcaagtacttttcaggggatccactggttaaaggcatcaagggctttgaggctgaatttataaagagtaaattctc
ctttaatctgaggaaaccctctgtgcagtggagtgacacagctgagtacttctgtgccgtgaatgc TRAV8-2:
atgctcctgctgctcgtcccagtgctcgaggtgattttactctgggaggaaccagagcccagtcggtgacccagcttgacagccacgt
ctctgtctctgaaggaaccccggtgctgctgaggtgcaactactcatcttcttattccaccatctctcttctggtatgtgcaacaccccaaca
aaggactccagcttctcctgaagtacacatcagcggccaccctggttaaaggcatcaacggttttgaggctgaatttaagaagagtgaa
acctccttccacctgacgaaaccctcagcccatatgagcgacgcggctgagtacttctgtgttgtgagtga TRAV8-3:
atgctcctggagcttatcccactgctggggatacattttgtcctgagaactgccagagcccagtcagtgacccagcctgacatccacatc
actgtctctgaaggagcctcactggagttgagatgtaactattcctatggggcaacaccttatctcttctggtatgtccagtcccccggcc
aaggcctccagctgctcctgaagtacttttcaggagacactctggttcaaggcattaaaggctttgaggctgaatttaagaggagtcaat
cttccttcaatctgaggaaaccctctgtgcattggagtgatgctgctgagtacttctgtgctgtgggtgc

Figure 7c

TRAV8-4:
atgctcctgctgctcgtcccagtgctcgaggtgattttacccctgggaggaaccagagcccagtcggtgacccagcttggcagccacg
tctctgtctctgaaggagccctggttctgctgaggtgcaactactcatcgtctgttccaccatatctcttctggtatgtgcaatacccaacc
aaggactccagcttctcctgaagtacacatcagcggccaccctggttaaaggcatcaacggttttgaggctgaatttaagaagagtgaa
acctccttccacctgacgaaaccctcagcccatatgagcgacgcggctgagtacttctgtgctgtgagtga TRAV8-6:
atgctcctgctgctcgtcccagcgttccaggtgattttacccctgggaggaaccagagcccagtctgtgacccagcttgacagccaagt
ccctgtctttgaagaagcccctgtggagctgaggtgcaactactcatcgtctgtttcagtgtatctcttctggtatgtgcaatacccaacc
aaggactccagcttctcctgaagtatttatcaggatccaccctggttaaaggcatcaacggttttgaggctgaatttaacaagagtcaaac
ttccttccacttgaggaaaccctcagtccatataagcgacacggctgagtacttctgtgctgtgagtga TRAV8-7:
atgctcttagtggtcattctgctgcttggaatgttcttcacactgagaggaaccagaacccagtcggtgacccagcttgatggccacatc
actgtctctgaagaagcccctctggaactgaagtgcaactattcctatagtggagttccttctctcttctggtatgtccaatactctagccaa
agcctccagcttctcctcaaagacctaacagaggccacccaggttaaaggcatcagaggttttgaggctgaatttaagaagagcgaaa
cctccttctacctgaggaaaccatcaacccatgtgagtgatgctgctgagtacttctgtgctgtgggtgacaggag TRAV9-1:
atgaattcttctccaggaccagcgattgcactattcttaatgtttgggggaatcaatggagattcagtggtccagacagaaggccaagtg
ctcccctctgaagggggattccctgattgtgaactgctcctatgaaaccacacagtacccttccctttttggtatgtccaatatcctggagaa
ggtccacagctccacctgaaagccatgaaggccaatgacaagggaaggaacaaaggttttgaagccatgtaccgtaaagaaaccac
ttctttccacttggagaaagactcagttcaagagtcagactccgctgtgtacttctgtgctctgagtga TRAV9-2:
atgaactattctccaggcttagtatctctgatactcttactgcttggaagaacccgtggaaattcagtgacccagatggaagggccagtg
actctctcagaagaggccttcctgactataaactgcacgtacacagccacaggatacccttcccttttctggtatgtccaatatcctggag
aaggtctacagctcctcctgaaagccacgaaggctgatgacaagggaagcaacaaaggttttgaagccacataccgtaaagaaacca
cttctttccacttggagaaaggctcagttcaagtgtcagactcagcggtgtacttctgtgctctgagtga TRAV10:
atgaaaaagcatctgacgaccttcttggtgattttgtggctttattttataggggggaatggcaaaaaccaagtggagcagagtcctcagt
ccctgatcatcctggagggaaagaactgcactcttcaatgcaattatacagtgagcccttcagcaacttaaggtggtataagcaagata
ctggggagaggtcctgtttccctgacaatcatgactttcagtgagaacacaaagtcgaacggaagatatacagcaactctggatgcagac
acaaagcaaagctctctgcacatcacagcctcccagctcagcgattcagcctcctacatctgtgtggtgagcg

Figure 7d

TRAV12-1:
atgatatccttgagagttttactggtgatcctgtggcttcagttaagctgggtttggagccaacggaaggaggtggagcaggatcctgga
cccttcaatgttccagagggagccactgtcgctttcaactgtacttacagcaacagtgcttctcagtctttcttctggtacagacaggattg
caggaaagaacctaagttgctgatgtccgtatactccagtggtaatgaagatggaaggtttacagcacagctcaatagagccagccag
tatatttccctgctcatcagagactccaagctcagtgattcagccacctacctctgtgtggtgaaca TRAV12-2:
atgatgaaatccttgagagttttactagtgatcctgtggcttcagttgagctgggtttggagccaacagaaggaggtggagcagaattct
ggaccccctcagtgttccagagggagccattgcctctctcaactgcacttacagtgaccgaggttccagtccttcttctggtacagacaa
tattctgggaaaagccctgagttgataatgttcatatactccaatggtgacaaagaagatggaaggtttacagcacagctcaataaagcc
agccagtatgtttctctgctcatcagagactcccagcccagtgattcagccacctacctctgtgccgtgaaca TRAV12-3:
atgatgaaatccttgagagttttactggtgatcctgtggcttcagttaagctgggtttggagccaacagaaggaggtggagcaggatcct
ggaccactcagtgttccagagggagccattgtttctctcaactgcacttacagcaacagtgcttttcaatacttcatgtggtacagacagta
ttccagaaaaggccctgagttgctgatgtacacatactccagtggtaacaaagaagatggaaggtttacagcacaggtcgataaatcca
gcaagtatatctccttgttcatcagagactcacagcccagtgattcagccacctacctctgtgcaatgagcg TRAV13-1:
atgacatccattcgagctgtatttatattcctgtggctgcagctggacttggtgaatggagagaatgtggagcagcatccttcaaccctga
gtgtccaggagggagacagcgctgttatcaagtgtacttattcagacagtgcctcaaactacttcccttggtataagcaagaacttggaa
aaggacctcagcttattatagacattcgttcaaatgtgggcgaaaagaaagaccaacgaattgctgttacattgaacaagacagccaaa
cattctccctgcacatcacagagacccaacctgaagactcggctgtctacttctgtgcagcaagta TRAV13-2:
atggcaggcattcgagctttatttatgtacttgtggctgcagctggactgggtgagcagaggagagagtgtgggctgcatcttcctacc
ctgagtgtccaggagggtgacaactctattatcaactgtgcttattcaaacagcgcctcagactacttcatttggtacaagcaagaatctg
gaaaaggtcctcaattcattatagacattcgttcaaatatggacaaaaggcaaggccaaagagtcaccgtttttattgaataagacagtga
aacatctctctctgcaaattgcagctactcaacctggagactcagctgtctacttttgtgcagagaata TRAV14:
atgtcactttctagcctgctgaaggtggtcacagcttcactgtggctaggacctggcattgcccagaagataactcaaacccaaccagg
aatgttcgtgcaggaaaaggaggctgtgactctggactgcacatatgacaccagtgatcaaagttatggtctattctggtacaagcagc
ccagcagtggggaaatgattttcttatttatcagggtcttatgacgagcaaaatgcaacagaaggtcgctactcattgaatttccagaa
ggcaagaaaatccgccaaccttgtcatctccgcttcacaactgggggactcagcaatgtatttctgtgcaatgagagaggg

Figure 7e

TRAV16:
atgaagcccaccctcatctcagtgcttgtgataatatttatactcagaggaacaagagcccagagagtgactcagcccgagaagctcct
ctctgtctttaaaggggccccagtggagctgaagtgcaactattcctattctgggagtcctgaactcttctggtatgtccagtactccagac
aacgcctccagttactcttgagacacatctctagagagagcatcaaaggcttcactgctgaccttaacaaaggcgagacatctttccacc
tgaagaaaccatttgctcaagaggaagactcagccatgtattactgtgctctaagtgg TRAV17:
atggaaactctcctgggagtgtctttggtgattctatggcttcaactggctagggtgaacagtcaacagggagaagaggatcctcaggc
cttgagcatccaggagggtgaaaatgccaccatgaactgcagttacaaaactagtataaacaatttacagtggtatagacaaaattcag
gtagaggccttgtccacctaattttaatacgttcaaatgaaagagagaaacacagtggaagattaagagtcacgcttgacacttccaaga
aaagcagttccttgttgatcacggcttcccgggcagcagacactgcttcttacttctgtgctacggacg TRAV18:
atgctgtctgcttcctgctcaggacttgtgatcttgttgatattcagaaggaccagtggagactcggttacccagacagaaggcccagtta
ccctccctgagagggcagctctgacattaaactgcacttatcagtccagctattcaacttttctattctggtatgtccagtatctaaacaaag
agcctgagctcctcctgaaaagttcagaaaaccaggagacggacagcagaggttttcaggccagtcctatcaagagtgacagttcctt
ccacctggagaagccctcggtgcagctgtcggactctgccgtgtactactgcgctctgagaga TRAV19:
atgctgactgccagcctgttgagggcagtcatagcctccatctgtgttgtatccagcatggctcagaaggtaactcaagcgcagactga
aatttctgtggtggagaaggaggatgtgaccttggactgtgtgtatgaaacccgtgatactacttattacttattctggtacaagcaaccac
caagtggagaattggttttccttattcgtcggaactcttttgatgagcaaaatgaaataagtggtcggtattcttggaacttccagaaatcca
ccagttccttcaacttcaccatcacagcctcacaagtcgtggactcagcagtatacttctgtgctctgagtgaggc TRAV20:
atggagaaaatgttggagtgtgcattcatagtcttgtggcttcagcttggctggttgagtggagaagaccaggtgacgcagagtcccga
ggccctgagactccaggagggagagagtagcagtcttaactgcagttacacagtcagcggtttaagagggctgttctggtataggcaa
gatcctgggaaaggccctgaattcctcttcacccctgtattcagctggggaagaaaaggagaaagaaaggctaaaagccacattaacaa
agaaggaaagctttctgcacatcacagcccctaaacctgaagactcagccacttatctctgtgctgtgcagg TRAV21:
atggagaccctcttgggcctgcttatcctttggctgcagctgcaatgggtgagcagcaaacaggaggtgacgcagattcctgcagctct
gagtgtcccagaaggagaaaacttggttctcaactgcagtttcactgatagcgctatttacaacctccagtggtttaggcaggaccctgg
gaaaggtctcacatctctgttgcttattcagtcaagtcagagagagcaaacaagtggaagacttaatgcctcgctggataaatcatcagg
acgtagtactttatacattgcagcttctcagcctggtgactcagccacctacctctgtgctgtgagg

Figure 7f

TRAV22:
atgaagaggatattgggagctctgctggggctcttgagtgcccaggtttgctgtgtgagaggaatacaagtggagcagagtcctccag
acctgattctccaggagggagccaattccacgctgcggtgcaattttctgactctgtgaacaatttgcagtggtttcatcaaaaccttgg
ggacagctcatcaacctgttttacattccctcagggacaaaacagaatggaagattaagcgccacgactgtcgctacggaacgctaca
gcttattgtacatttcctcttcccagaccacagactcaggcgtttatttctgtgctgtggagc TRAV23:
atggacaagatcttaggagcatcattttagttctgtggcttcaactatgctgggtgagtggccaacagaaggagaaaagtgaccagca
gcaggtgaaacaaagtcctcaatctttgatagtccagaaggagggatttcaattataaactgtgcttatgagaacactgcgtttgactac
tttccatggtaccaacaattccctgggaaaggccctgcattattgatagccatacgtccagatgtgagtgaaaagaaagaaggaagatt
cacaatctccttcaataaaagtgccaagcagttctcattgcatatcatggattcccagcctggagactcagccacctacttctgtgcagca
agca TRAV24:
atggagaagaatcctttggcagccccattactaatcctctggtttcatcttgactgcgtgagcagcatactgaacgtggaacaaagtcctc
agtcactgcatgttcaggagggagacagcaccaatttcacctgcagcttcccttccagcaattttttatgccttacactggtacagatggga
aactgcaaaaagccccgaggccttgtttgtaatgactttaaatggggatgaaaagaagaaaggacgaataagtgccactcttaatacca
aggagggttacagctatttgtacatcaaaggatcccagcctgaagactcagccacatacctctgtgcctta TRAV25:
atgctactcatcacatcaatgttggtcttatggatgcaattgtcacaggtgaatggacaacaggtaatgcaaattcctcagtaccagcatgt
acaagaaggagaggacttcaccacgtactgcaattcctcaactactttaagcaatatacagtggtataagcaaaggcctggtggacatc
ccgttttttgatacagttagtgaagagtggagaagtgaagaagcagaaaagactgacatttcagtttggagaagcaaaaaagaacagc
tccctgcacatcacagccacccagactacagatgtaggaacctacttctgtgcaggg TRAV26-1:
atgaggctggtggcaagagtaactgtgtttctgacctttggaactataattgatgctaagaccacccagcccccctccatggattgcgct
gaaggaagagctgcaaacctgccttgtaatcactctaccatcagtggaaatgagtatgtgtattggtatcgacagattcactcccagggg
ccacagtatatcattcatggtctaaaaaacaatgaaaccaatgaaatggcctctctgatcatcacagaagacagaaagtccagcaccttg
atcctgccccacgctacgctgagagacactgctgtgtactattgcatcgtcagagtcg TRAV26-2:
atgaagttggtgacaagcattactgtactcctatctttgggtattatgggtgatgctaagaccacacagccaaattcaatggagagtaacg
aagaagagcctgttcacttgccttgtaaccactccacaatcagtggaactgattacatacattggtatcgacagcttccctcccagggtcc
agagtacgtgattcatggtcttacaagcaatgtgaacaacagaatggcctctctggcaatcgctgaagacagaaagtccagtaccttga
tcctgcaccgtgctaccttgagagatgctgctgtgtactactgcatcctgagagac TRAV27:
atggtcctgaaattctccgtgtccattctttggattcagttggcatgggtgagcacccagctgctggagcagagccctcagtttctaagca
tccaagagggagaaaatctcactgtgtactgcaactcctcaagtgtttttccagcttacaatggtacagacaggagcctggggaaggtc
ctgtcctcctggtgacagtagttacgggtggagaagtgaagaagctgaagagactaacctttcagtttggtgatgcaagaaaggacagt
tctctccacatcactgcagcccagcctggtgatacaggcctctacctctgtgcaggag

Figure 7g

TRAV29:
atggccatgctcctgggggcatcagtgctgattctgtggcttcagccagactgggtaaacagtcaacagaagaatgatgaccagcaag
ttaagcaaaattcaccatccctgagcgtccaggaaggaagaatttctattctgaactgtgactatactaacagcatgtttgattatttcctat
ggtacaaaaaatacccctgctgaaggtcctacattcctgatatctataagttccattaaggataaaaatgaagatggaagattcactgtcttc
ttaaacaaaagtgccaagcacctctctctgcacattgtgccctcccagcctggagactctgcagtgtacttctgtgcagcaagcg TRAV30:
atggagactctcctgaaagtgctttcaggcaccttgttgtggcagttgacctgggtgagaagccaacaaccagtgcagagtcctcaagc
cgtgatcctccgagaaggggaagatgctgtcatcaactgcagttcctccaaggctttatattctgtacactggtacaggcagaagcatg
gtgaagcacccgtcttcctgatgatattactgaagggtggagaacagaaggtcatgaaaaaatatctgcttcatttaatgaaaaaagc
agcaaagctccctgtaccttacggcctcccagctcagttactcaggaacctacttctgcggcacagaga TRAV34:
atggagactgttctgcaagtactcctagggatattggggttccaagcagcctgggtcagtagccaagaactggagcagagtcctcagt
ccttgatcgtccaagagggaaagaatctcaccataaactgcacgtcatcaaagacgttatatggcttatactggtataagcaaaagtatg
gtgaaggtcttatcttcttgatgatgctacagaaaggtggggaagagaaaagtcatgaaaagtaactgccaagttggatgagaaaaa
gcagcaaagttccctgcatatcacagcctcccagcccagccatgcaggcatctacctctgtggagcagaca TRAV35:
atgctccttgaacatttattaataatcttgtggatgcagctgacatgggtcagtggtcaacagctgaatcagagtcctcaatctatgtttatc
caggaaggagaagatgtctccatgaactgcacttcttcaagcatatttaacacctggctatggtacaagcaggaacctggggaaggtc
ctgtcctcttgatagccttatataaggctggtgaattgacctcaaatggaagactgactgctcagtttggtataaccagaaaggacagctt
cctgaatatctcagcatccatacctagtgatgtaggcatctacttctgtgctgggcag TRAV36:
atgatgaagtgtccacaggctttactagctatcttttggcttctactgagctgggtgagcagtgaagacaaggtggtacaaagccctctat
ctctggttgtccacgagggagacaccgtaactctcaattgcagttatgaagtgactaactttcgaagcctactatggtacaagcaggaaa
agaaagctcccacatttctatttatgctaacttcaagtggaattgaaaagaagtcaggaagactaagtagcatattagataagaaagaact
ttccagcatcctgaacatcacagccacccagaccggagactcggccatctacctctgtgctgtggagg TRAV38-1:
atgacacgagttagcttgctgtgggcagtcgtggtctccacctgtcttgaatccggcatggcccagacagtcactcagtctcaaccaga
gatgtctgtgcaggaggcagagactgtgaccctgagttgcacatatgacaccagtgagaataattattatttgttctggtacaagcagcct
cccagcaggcagatgattctcgttattcgccaagaagcttataagcaacagaatgcaacggagaatcgtttctctgtgaacttccagaaa
gcagccaaatccttcagtctcaagatctcagactcacagctggggacactgcgatgtatttctgtgctttcatgaagca

Figure 7h

TRAV38-2:
atggcatgccctggcttcctgtgggcacttgtgatctccacctgtcttgaatttagcatggctcagacagtcactcagtctcaaccagaga
tgtctgtgcaggaggcagagaccgtgaccctgagctgcacatatgacaccagtgagagtgattattatttattctggtacaagcagcctc
ccagcaggcagatgattctcgttattcgccaagaagcttataagcaacagaatgcaacagagaatcgtttctctgtgaacttccagaaag
cagccaaatccttcagtctcaagatctcagactcacagctgggggatgccgcgatgtatttctgtgcttataggagcg TRAV39:
atgaagaagctactagcaatgattctgtggcttcaactagaccggttaagtggagagctgaaagtggaacaaaaccctctgttcctgag
catgcaggagggaaaaaactataccatctactgcaattattcaaccacttcagacagactgtattggtacaggcaggatcctgggaaaa
gtctggaatctctgtttgtgttgctatcaaatggagcagtgaagcaggagggacgattaatggcctcacttgataccaaagcccgtctca
gcaccctccacatcacagctgccgtgcatgacctctctgccacctacttctgtgccgtggaca TRAV40:
atgaactcctctctggactttctaattctgatcttaatgtttggaggaaccagcagcaattcagtcaagcagacgggccaaataaccgtct
cggagggagcatctgtgactatgaactgcacatacacatccacggggtaccctacccttttctggtatgtggaataccccagcaaacct
ctgcagcttcttcagagagagacaatggaaaacagcaaaaacttcggaggcggaaatattaaagacaaaaactcccccattgtgaaat
attcagtccaggtatcagactcagccgtgtactactgtcttctgggaga TRAV41:
atggtgaagatccggcaattttttgttggctattttgtggcttcagctaagctgtgtaagtgccgccaaaaatgaagtggagcagagtcctc
agaacctgactgcccaggaaggagaatttatcacaatcaactgcagttactcggtaggaataagtgccttacactggctgcaacagcat
ccaggaggaggcattgttccttgtttatgctgagctcagggaagaagaagcatggaagattaattgccacaataaacatacaggaaaa
gcacagctccctgcacatcacagcctcccatcccagagactctgccgtctacatctgtgctgtcaga

Figure 8a

TRBC1:
aggacctgaacaaggtgttcccacccgaggtcgctgtgtttgagccatcagaagcagagatctcccacacccaaaaggccacactgg
tgtgcctggccacaggcttcttccccgaccacgtggagctgagctggtgggtgaatgggaaggaggtgcacagtggggtcagcaca
gacccgcagcccctcaaggagcagcccgccctcaatgactccagatactgcctgagcagccgcctgagggtctcggccaccttctg
gcagaaccccccgcaaccacttccgctgtcaagtcctgcctgcctgcaagtccagttctacgggctctcggagaatgacgagtggacccaggatagggccaaac
ccgtcacccagatcgtcagcgccgaggcctggggtagagcagactgtggctttacctcggtgtcctaccagcaagggggtcctgtctg
ccaccatcctctatgagatcctgctagggaaggccaccctgtatgctgtgctggtcagcgcccttgtgttgatggccatggtcaagaga
aaggatttctga TRBC2:
aggacctgaaaaacgtgttcccacccgaggtcgctgtgtttgagccatcagaagcagagatctcccacacccaaaaggccacactgg
tatgcctggccacaggcttctaccccgaccacgtggagctgagctggtgggtgaatgggaaggaggtgcacagtggggtcagcaca
gacccgcagcccctcaaggagcagcccgccctcaatgactccagatactgcctgagcagccgcctgagggtctcggccaccttctg
gcagaaccccccgcaaccacttccgctgtcaagtccagttctacgggctctcggagaatgacgagtggacccaggatagggccaaac
ccgtcacccagatcgtcagcgccgaggcctggggtagagcagactgtggcttcacctccgagtcttaccagcaagggggtcctgtctg
ccaccatcctctatgagatcttgctagggaaggccaccttgtatgccgtgctggtcagtgccctcgtgctgatggccatggtcaagaga
aaggattccagaggctag TRBV2:
atggatacctggctcgtatgctgggcaattttagtctcttgaaagcaggactcacagaacctgaagtcacccagactccagccatcag
gtcacacagatgggacaggaagtgatcttcgctgtgtccccatctctaatcacttatacttctattggtacagacaaatcttggggcaga
aagtcgagtttctggtttccttttataataatgaaatctcagagaagtctgaaatattcgatgatcaattctcagttgaaaggcctgatggatc
aaatttcactctgaagatccggtccacaaagctggaggactcagccatgtacttctgtgccagcagtgaagc TRBV3-1:
atgggctgcaggctcctctgctgtgtggtcttctgcctcctccaagcaggtcccttggacacagctgtttcccagactccaaaatacctg
gtcacacagatgggaaacgacaagtccattaaatgtgaacaaaatctgggccatgatactatgtattggtataaacaggactctaagaa
atttctgaagataatgtttagctacaataataaggagctcattataaatgaaacagttccaaatcgcttctcacctaaatctccagacaaag
ctcacttaaatcttcacatcaattccctggagcttggtgactctgctgtgtatttctgtgccagcagccaaga TRBV4-1:
atgggctgcaggctgctctgctgtgcggttctctgtctcctgggagcagttcccatagacactgaagttacccagacaccaaaacacct
ggtcatgggaatgacaaataagaagtctttgaaatgtgaacaacatatggggcacagggctatgtattggtacaagcagaaagctaag
aagccaccggagctcatgtttgtctacagctatgagaaactctctataaatgaaagtgtgccaagtcgcttctcacctgaatgccccaac
agctctctcttaaaccttcacctacacgccctgcagccagaagactcagccctgtatctctgcgccagcagccaaga

Figure 8b

TRBV4-2:
atgggctgcaggctgctctgctgtgcggttctctgtctcctgggagcggtccccatggaaacgggagttacgcagacaccaagacac
ctggtcatgggaatgacaaataagaagtctttgaaatgtgaacaacatctggggcataacgctatgtattggtacaagcaaagtgctaag
aagccactggagctcatgtttgtctacaactttaaagaacagactgaaaacaacagtgtgccaagtcgcttctcacctgaatgccccaac
agctctcacttattccttcacctacacaccctgcagccagaagactcggccctgtatctctgtgccagcagccaaga TRBV4-3:
atgggctgcaggctgctctgctgtgcggttctctgtctcctgggagcggtccccatggaaacgggagttacgcagacaccaagacac
ctggtcatgggaatgacaaataagaagtctttgaaatgtgaacaacatctgggtcataacgctatgtattggtacaagcaaagtgctaag
aagccactggagctcatgtttgtctacagtcttgaagaacgggttgaaaacaacagtgtgccaagtcgcttctcacctgaatgccccaac
agctctcacttattccttcacctacacaccctgcagccagaagactcggccctgtatctctgcgccagcagccaaga TRBV5-1:
atgggctccaggctgctctgttgggtgctgctttgtctcctgggagcaggcccagtaaaggctggagtcactcaaactccaagatatct
gatcaaaacgagaggacagcaagtgacactgagctgctccctatctctgggcataggagtgtatcctggtaccaacagacccccagg
acagggccttcagttcctctttgaatacttcagtgagacacagagaaacaaaggaaacttccctggtcgattctcagggcgccagttctc
taactctcgctctgagatgaatgtgagcaccttggagctgggggactcggccctttatctttgcgccagcagcttgg TRBV5-3:
atgggccccgggctcctctgctgggaactgctttatctcctgggagcaggcccagtggaggctggagtcacccaaagtcccacacac
ctgatcaaaacgagaggacagcaagtgactctgagatgctctcctatctctgggcacagcagtgtgtcctggtaccaacaggccccgg
gtcaggggcccccagtttatctttgaatatgctaatgagttaaggagatcagaaggaaacttccctaatcgattctcagggcgccagttcc
atgactgttgctctgagatgaatgtgagtgccttggagctgggggactcggccctgtatctctgtgccagaagctt TRBV5-4:
atgggccctgggctcctctgctgggtgctgctttgtctcctgggagcaggctcagtggagactggagtcacccaaagtcccacacacc
tgatcaaaacgagaggacagcaagtgactctgagatgctcttctcagtctgggcacaacactgtgtcctggtaccaacaggccctggg
tcaggggcccccagtttatctttcagtattataggaggaagagaatggcagaggaaacttccctcctagattctcaggtctccagttccct
aattatagctctgagctgaatgtgaacgccttggagctggacgactcggccctgtatctctgtgccagcagcttgg TRBV5-5:
atgggccctgggctcctctgctgggtgctgctttgtctcctgggagcaggcccagtggacgctggagtcacccaaagtcccacacacc
tgatcaaaacgagaggacagcaagtgactctgagatgctctcctatctctgggcacaagagtgtgtcctggtaccaacaggtcctgggt
caggggcccccagtttatctttcagtattatgagaaagaagagagaggaagaggaaacttccctgatcgattctcagctcgccagttccct
aactatagctctgagctgaatgtgaacgccttgttgctgggggactcggccctgtatctctgtgccagcagcttgg

Figure 8c

TRBV5-6:
atgggccccggggctcctctgctgggcactgctttgtctcctgggagcaggcttagtggacgctggagtcacccaaagtcccacacacc
tgatcaaaacgagaggacagcaagtgactctgagatgctctcctaagtctgggcatgacactgtgtcctggtaccaacaggccctggg
tcaggggccccagtttatctttcagtattatgaggaggaagagagacagagaggcaacttccctgatcgattctcaggtcaccagttccc
taactatagctctgagctgaatgtgaacgccttgttgctgggggactcggccctctatctctgtgccagcagcttgg TRBV5-7:
atgggccccggggctcctctgctgggtgctgctttgtccctaggagaaggcccagtggacgctggagtcacccaaagtcccacacac
ctgatcaaaacgagaggacagcacgtgactctgagatgctctcctatctctgggcacaccagtgtgtcctcgtaccaacaggccctgg
gtcaggggccccagtttatctttcagtattatgagaaagaagagagaggaagaggaaacttccctgatcaattctcaggtcaccagttcc
ctaactatagctctgagctgaatgtgaacgccttgttgctaggggactcggccctctatctctgtgccagcagcttgg TRBV5-8:
atgggacccaggctcctcttctgggcactgctttgtctcctcggaacaggcccagtggaggctggagtcacacaaagtcccacacacc
tgatcaaaacgagaggacagcaagcgactctgagatgctctcctatctctgggcacaccagtgtgtactggtaccaacaggccctggg
tctgggcctccagttcctcctttggtatgacgagggtgaagagagaaacagaggaaacttccctcctagattttcaggtcgccagttccc
taattatagctctgagctgaatgtgaacgccttggagctggaggactcggccctgtatctctgtgccagcagcttgg TRBV6-1:
atgagcatcgggctcctgtgctgtgtggccttttctctcctgtgggcaagtccagtgaatgctggtgtcactcagaccccaaaattccag
gtcctgaagacaggacagagcatgacactgcagtgtgcccaggatatgaaccataactccatgtactggtatcgacaagacccaggc
atgggactgaggctgatttattactcagcttctgagggtaccactgacaaaggagaagtcccaatggctacaatgtctccagattaaac
aaacgggagttctcgctcaggctggagtcggctgctccctcccagacatctgtgtacttctgtgccagcagtgaagc TRBV6-2:
atgagcctcgggctcctgtgctgtggggccttttctctcctgtgggcaggtccagtgaatgctggtgtcactcagaccccaaaattccgg
gtcctgaagacaggacagagcatgacactgctgtgtgcccaggatatgaaccatgaatacatgtactggtatcgacaagacccaggc
atggggctgaggctgattcattactcagttggtgagggtacaactgccaaaggagaggtccctgatggctacaatgtctccagattaaa
aaaacagaatttcctgctggggttggagtcggctgctccctcccaaacatctgtgtacttctgtgccagcagttactc TRBV6-3:
atgagcctcgggctcctgtgctgtggggtcttttctctcctgtgggcaggtccagtgaatgctggtgtcactcagaccccaaaattccgg
gtcctgaagacaggacagagcatgacactgctgtgtgcccaggatatgaaccatgaatacatgtactggtatcgacaagacccaggc
atggggctgaggctgattcattactcagttggtgagggtacaactgccaaaggagaggtccctgatggctacaatgtctccagattaaa
aaaacagaatttcctgctggggttggagtcggctgctccctcccaaacatctgtgtacttctgtgccagcagttactc

Figure 8d

TRBV6-4:
atgagaatcaggctcctgtgctgtgtggccttttctctcctgtgggcaggtccagtgattgctgggatcacccaggcaccaacatctcag
atcctggcagcaggacggcgcatgacactgagatgtacccaggatatgagacataatgccatgtactggtatagacaagatctaggac
tggggctaaggctcatccattattcaaatactgcaggtaccactggcaaaggagaagtccctgatggttatagtgtctccagagcaaac
acagatgatttcccccctcacgttggcgtctgctgtaccctctcagacatctgtgtacttctgtgccagcagtgactc TRBV6-5:
atgagcatcggcctcctgtgctgtgcagccttgtctctcctgtgggcaggtccagtgaatgctggtgtcactcagacccccaaaattccag
gtcctgaagacaggacagagcatgacactgcagtgtgcccaggatatgaaccatgaatacatgtcctggtatcgacaagacccaggc
atggggctgaggctgattcattactcagttggtgctggtatcactgaccaaggagaagtccccaatggctacaatgtctccagatcaacc
acagaggatttcccgctcaggctgctgtcggctgctccctcccagacatctgtgtacttctgtgccagcagttactc TRBV6-6:
atgagcatcagcctcctgtgctgtgcagcctttcctctcctgtgggcaggtccagtgaatgctggtgtcactcagacccccaaaattccgc
atcctgaagataggacagagcatgacactgcagtgtacccaggatatgaaccataactacatgtactggtatcgacaagacccaggca
tggggctgaagctgatttattattcagttggtgctggtatcactgataaaggagaagtcccgaatggctacaacgtctccagatcaacca
cagaggatttcccgctcaggctggagttggctgctccctcccagacatctgtgtacttctgtgccagcagttactc TRBV6-7:
atgagcctcgggctcctgtgctgtgtggccttttctctcctgtgggcaggtccaatgaatgctggtgtcactcagacccccaaaattccacg
tcctgaagacaggacagagcatgactctgctgtgtgcccaggatatgaaccatgaatacatgtatcggtatcgacaagacccaggcaa
ggggctgaggctgatttactactcagttgctgctgctctcactgacaaaggagaagttcccaatggctacaatgtctccagatcaaacac
agaggatttccccctcaagctggagtcagctgctccctctcagacttctgtttacttctgtgccagcagttactc TRBV6-8:
atgagcctcgggctcctgtgctgtgcggccttttctctcctgtgggcaggtcccgtgaatgctggtgtcactcagacccccaaaattccac
atcctgaagacaggacagagcatgacactgcagtgtgcccaggatatgaaccatggatacatgtcctggtatcgacaagacccaggc
atggggctgagactgatttactactcagctgctgctggtactactgacaaagaagtcccccaatggctacaatgtctctagattaaacaca
gaggatttcccactcaggctggtgtcggctgctccctcccagacatctgtgtacttgtgtgccagcagttactc TRBV6-9:
atgagcatcgggctcctgtgctgtgtggccttttctctcctgtgggcaggtccagtgaatgctggtgtcactcagacccccaaaattccaca
tcctgaagacaggacagagcatgacactgcagtgtgcccaggatatgaaccatggatacttgtcctggtatcgacaagacccaggcat
ggggctgaggcgcattcattactcagttgctgctggtatcactgacaaaggagaagtccccgatggctacaatgtatccagatcaaaca
cagaggatttcccgctcaggctggagtcagctgctccctcccagacatctgtatacttctgtgccagcagttattc

Figure 8e

TRBV7-1:
atgggcacaaggctcctctgctgggcagccatatgtctcctgggggcagatcacacaggtgctggagtctcccagtccctgagacac
aaggtagcaaagaagggaaaggatgtagctctcagatatgatccaatttcaggtcataatgccctttattggtaccgacagagcctggg
gcagggcctggagtttccaatttacttccaaggcaaggatgcagcagacaaatcgggcttccccgtgatcggttctctgcacagagg
tctgagggatccatctccactctgaagttccagcgcacacagcaggggacttggctgtgtatctctgtgccagcagctcagc TRBV7-2:
atgggcaccaggctcctcttctgggtggccttctgtctcctgggggcagatcacacaggagctggagtctcccagtcccccagtaaca
aggtcacagagaagggaaaggatgtagagctcaggtgtgatccaatttcaggtcatactgccctttactggtaccgacagagcctggg
gcagggcctggagttttaatttacttccaaggcaacagtgcaccagacaaatcagggctgcccagtgatcgcttctctgcagagagga
ctgggggatccgtctccactctgacgatccagcgcacacagcaggaggactcggccgtgtatctctgtgccagcagcttagc TRBV7-3:
atgggcaccaggctcctctgctgggcagccctgtgcctcctgggggcagatcacacaggtgctggagtctcccagacccccagtaac
aaggtcacagagaagggaaaatatgtagagctcaggtgtgatccaatttcaggtcatactgccctttactggtaccgacaaagcctggg
gcagggcccagagtttctaatttacttccaaggcacgggtgcggcagatgactcagggctgcccaacgatcggttctttgcagtcagg
cctgagggatccgtctctactctgaagatccagcgcacagagcgggggactcagccgtgtatctctgtgccagcagcttaac TRBV7-4:
atgggcaccaggctcctctgctgggtggtcctgggtttcctagggacagatcacacaggtgctggagtctcccagtcccaaggtaca
aagtcgcaaagagggacgggatgtagctctcaggtgtgattcaatttcgggtcatgtaaccctttattggtaccgacagaccctgggg
cagggctcagaggttctgacttactcccagagtgatgctcaacgagacaaatcagggcggcccagtggtcggttctctgcagagagg
cctgagagatccgtctccactctgaagatccagcgcacagagcaggggggactcagctgtgtatctctgtgccagcagcttagc TRBV7-6:
atgggcaccagtctcctatgctgggtggtcctgggtttcctagggacagatcacacaggtgctggagtctcccagtctcccaggtacaa
agtcacaaagaggggacaggatgtagctctcaggtgtgatccaatttcgggtcatgtatccctttattggtaccgacaggccctggggc
agggcccagagtttctgacttacttcaattatgaagcccaacaagacaaatcagggctgcccaatgatcggttctctgcagagaggcct
gagggatccatctccactctgacgatccagcgcacagagcagcgggactcggccatgtatcgctgtgccagcagcttagc TRBV7-7:
atgggtaccagtctcctatgctgggtggtcctgggtttcctagggacagatcacacaggtgctggagtctcccagtctcccaggtacaa
agtcacaaagaggggacaggatgtaactctcaggtgtgatccaatttcgagtcatgcaacccttattggtatcaacaggccctggggc
agggcccagagtttctgacttacttcaattatgaagctcaaccagacaaatcagggctgcccagtgatcggttctctgcagagaggcct
gagggatccatctccactctgacgattcagcgcacagagcagcgggactcagccatgtatcgctgtgccagcagcttagc

Figure 8f

TRBV7-8:
atggggcaccaggctcctctgctgggtggtcctgggtttcctagggacagatcacacaggtgctggagtctcccagtcccctaggtaca
aagtcgcaaagagaggacaggatgtagctctcaggtgtgatccaatttcgggtcatgtatcccttttttggtaccaacaggccctggggc
aggggccagagtttctgacttatttccagaatgaagctcaactagacaaatcggggctgcccagtgatcgcttctttgcagaaaggcct
gagggatccgtctccactctgaagatccagcgcacacagcaggaggactccgccgtgtatctctgtgccagcagcttagc TRBV7-9:
atggggcaccagcctcctctgctggatggccctgtgtctcctgggggcagatcacgcagatactggagtctcccagaaccccagacac
aagatcacaaagaggggacagaatgtaactttcaggtgtgatccaatttctgaacacaaccgcctttattggtaccgacagaccctggg
gcagggcccagagtttctgacttacttccagaatgaagctcaactagaaaaatcaaggctgctcagtgatcggttctctgcagagaggc
ctaagggatctttctccaccttggagatccagcgcacagagcagggggactcggccatgtatctctgtgccagcagcttagc TRBV9:
atgggcttcaggctcctctgctgtgtggccttttgtctcctgggagcaggcccagtggattctggagtcacacaaaccccaaagcacct
gatcacagcaactggacagcgagtgacgctgagatgctccccctaggtctggagacctctctgtgtactggtaccaacagagcctgga
ccagggcctccagttcctcattcagtattataatggagaagagagagcaaaaggaaacattcttgaacgattctccgcacaacagttcc
ctgacttgcactctgaactaaacctgagctctctggagctggggggactcagctttgtatttctgtgccagcagcgtag TRBV10-1:
atgggcacgaggctcttcttctatgtggcccttttgtctgctgtgggcaggacacagggatgctgaaatcacccagagcccaagacaca
agatcacagagacaggaaggcaggtgaccttggcgtgtcaccagacttggaaccacaacaatatgttctggtatcgacaagacctgg
gacatgggctgaggctgatccattactcatatggtgttcaagacactaacaaaggagaagtctcagatggctacagtgtctctagatcaa
acacagaggacctcccccctcactctggagtctgctgcctcctcccagacatctgtatatttctgcgccagcagtgagtc TRBV10-2:
atgggcaccaggctcttcttctatgtggcccttttgtctgctgtgggcaggacacagggatgctggaatcacccagagcccaagatacaa
gatcacagagacaggaaggcaggtgaccttgatgtgtcaccagacttggagccacagctatatgttctggtatcgacaagacctggga
catgggctgaggctgatctattactcagcagctgctgatattacagataaaggagaagtccccgatggctatgttgtctccagatccaag
acagagaatttccccctcactctggagtcagctacccgctcccagacatctgtgtatttctgcgccagcagtgagtc TRBV10-3:
atgggcacaaggttgttcttctatgtggcccctttgtctcctgtggacaggacacatggatgctggaatcacccagagcccaagacacaa
ggtcacagagacaggaacaccagtgactctgagatgtcaccagactgagaaccaccgctatatgtactggtatcgacaagacccggg
gcatgggctgaggctgatccattactcatatggtgttaaagatactgacaaaggagaagtctcagatggctatagtgtctctagatcaaa
gacagaggatttcctcctcactctggagtccgctaccagctcccagacatctgtgtacttctgtgccatcagtgagtc

Figure 8g

TRBV11-1:
atgagcaccaggcttctctgctggatggccctctgtctcctgggggcagaactctcagaagctgaagttgcccagtcccccagatataa
gattacagagaaaagccaggctgtggcttttggtgtgatcctatttctggccatgctacccttactggtaccggcagatcctgggacag
ggcccggagcttctggttcaatttcaggatgagagtgtagtagatgattcacagttgcctaaggatcgatttctgcagagaggctcaaa
ggagtagactccactctcaagatccagcctgcagagcttggggactcggccatgtatctctgtgccagcagcttagc TRBV11-2:
atgggcaccaggctcctctgctgggcggccctctgtctcctgggagcagaactcacagaagctggagttgcccagtctcccagatata
agattatagagaaaaggcagagtgtggcttttttggtgcaatcctatatctggccatgctacccttactggtaccagcagatcctgggaca
gggcccaaagcttctgattcagtttcagaataacggtgtagtggatgattcacagttgcctaaggatcgatttctgcagagaggctcaaa
ggagtagactccactctcaagatccagcctgcaaagcttgaggactcggccgtgtatctctgtgccagcagcttaga TRBV11-3:
atgggtaccaggctcctctgctgggtggccttctgtctcctggtggaagaactcatagaagctggagtggttcagtctcccagatataag
attatagagaaaaaacagcctgtggcttttttggtgcaatcctatttctggccacaatacccttactggtacctgcagaacttgggacagg
gcccggagcttctgattcgatatgagaatgaggaagcagtagacgattcacagttgcctaaggatcgatttctgcagagaggctcaaa
ggagtagactccactctcaagatccagcctgcagagcttggggactcggccgtgtatctctgtgccagcagcttaga TRBV12-3:
atggactcctggaccttctgctgtgtgtccctttgcatcctggtagcgaagcatacagatgctggagttatccagtcaccccgccatgag
gtgacagagatgggacaagaagtgactctgagatgtaaaccaatttcaggccacaactccctttctggtacagacagaccatgatgcg
gggactggagttgctcatttactttaacaacaacgttccgatagatgattcagggatgcccgaggatcgattctcagctaagatgcctaat
gcatcattctccactctgaagatccagccctcagaacccagggactcagctgtgtacttctgtgccagcagtttagc TRBV12-4:
atggactcctggaccctctgctgtgtgtccctttgcatcctggtagcaaagcacacagatgctggagttatccagtcaccccggcacga
ggtgacagagatgggacaagaagtgactctgagatgtaaaccaatttcaggacacgactaccttttctggtacagacagaccatgatg
cggggactggagttgctcatttactttaacaacaacgttccgatagatgattcagggatgcccgaggatcgattctcagctaagatgcct
aatgcatcattctccactctgaagatccagccctcagaacccagggactcagctgtgtacttctgtgccagcagtttagc TRBV12-5:
atggccaccaggctcctctgctgtgtggttctttgtctcctgggagaagagcttatagatgctagagtcacccagacaccaaggcacaa
ggtgacagagatgggacaagaagtaacaatgagatgtcagccaattttaggccacaatactgttttctggtacagacagaccatgatgc
aaggactggagttgctggcttacttccgcaaccgggctcctctagatgattcggggatgccgaaggatcgattctcagcagagatgcct
gatgcaactttagccactctgaagatccagccctcagaacccagggactcagctgtgtattttgtgctagtggtttggt

Figure 8h

TRBV13:
atgcttagtcctgacctgcctgactctgcctggaacaccaggctcctctgccatgtcatgctttgtctcctgggagcagtttcagtggctg
ctggagtcatccagtccccaagacatctgatcaaagaaaagagggaaacagccactctgaaatgctatcctatccctagacacgacac
tgtctactggtaccagcagggtccaggtcaggaccccagttcctcatttcgttttatgaaaagatgcagagcgataaaggaagcatcc
ctgatcgattctcagctcaacagttcagtgactatcattctgaactgaacatgagctccttggagctgggggactcagccctgtacttctgt
gccagcagcttagg TRBV14:
atgggtttccaggcttctcagtttagtgtcccttttgtctcctgggagcaaagcacatagaagctggagttactcagttccccagccacagcg
taatagagaagggccagactgtgactctgagatgtgacccaatttctggacatgataatctttattggtatcgacgtgttatgggaaaaga
aataaaatttctgttacattttgtgaaagagtctaaacaggatgagtccggtatgcccaacaatcgattcttagctgaaaggactggaggg
acgtattctactctgaaggtgcagcctgcagaactggaggattctggagtttatttctgtgccagcagccaaga TRBV15:
atgggtcctgggcttctccactggatggcccctttgtctccttggaacaggtcatggggatgccatggtcatccagaacccaagatacca
ggttacccagtttggaaagccagtgaccctgagttgttctcagactttgaaccataacgtcatgtactggtaccagcagaagtcaagtca
ggccccaaagctgctgttccactactatgacaaagattttaacaatgaagcagacacccctgataacttccaatccaggaggccgaaca
cttctttctgctttcttgacatccgctcaccaggcctgggggacacagccatgtacctgtgtgccaccagcagaga TRBV16:
atgagcccaatattcacctgcatcacaatcctttgtctgctggctgcaggttctcctggtgaagaagtcgcccagactccaaaacatcttg
tcagaggggaaggacagaaagcaaaattatattgtgccccaataaaaggacacagttaggttttttggtaccaacaggtcctgaaaaac
gagttcaagttcttgatttccttccagaatgaaaatgtctttgatgaaacaggtatgcccaaggaaagattttcagctaagtgcctcccaaa
ttcaccctgtagccttgagatccaggctacgaagcttgaggattcagcagtgtatttttgtgccagcagccaatc TRBV17:
atggatatctggctcctctgctgggtgaccctgtgtctcttggcggcaggacactcggagcctggagtcagccagaccccagacaca
aggtcaccaacatgggacaggaggtgattctgaggtgcgatccatcttctggtcacatgtttgttcactggtaccgacagaatctgaggc
aagaaatgaagttgctgatttccttccagtaccaaaacattgcagttgattcagggatgcccaaggaacgattcacagctgaaagaccta
acggaacgtcttccacgctgaagatccatcccgcagagccgagggactcagccgtgtatctctacagtagcggtgg TRBV18:
atggacaccagagtactctgctgtgcggtcatctgtcttctgggggcaggtctctcaaatgccggcgtcatgcagaacccaagacacct
ggtcaggaggagggacaggaggcaagactgagatgcagcccaatgaaaggacacagtcatgtttactggtatcggcagctccca
gaggaaggtctgaaattcatggtttatctccagaaagaaaatatcatagatgagtcaggaatgccaaaggaacgattttctgctgaatttc
ccaaagagggcccccagcatcctgaggatccagcaggtagtgcgaggagattcggcagcttattctgtgccagctcaccacc

Figure 8i

TRBV19:
atgagcaaccaggtgctctgctgtgtggtcctttgtttcctgggagcaaacaccgtggatggtggaatcactcagtccccaaagtacctg
ttcagaaaggaaggacagaatgtgaccctgagttgtgaacagaatttgaaccacgatgccatgtactggtaccgacaggacccaggg
caagggctgagattgatctactactcacagatagtaaatgactttcagaaaggagatatagctgaagggtacagcgtctctcgggagaa
gaaggaatccttcctctcactgtgacatcggcccaaaagaacccgacagctttctatctctgtgccagtagtataga TRBV20-1:
atgctgctgcttctgctgcttctggggccaggctccgggcttggtgctgtcgtctctcaacatccgagctgggttatctgtaagagtggaa
cctctgtgaagatcgagtgccgttccctggactttcaggccacaactatgttttggtatcgtcagttcccgaaacagagtctcatgctgatg
gcaacttccaatgagggctccaaggccacatacgagcaaggcgtcgagaaggacaagtttctcatcaaccatgcaagcctgaccttgt
ccactctgacagtgaccagtgcccatcctgaagacagcagcttctacatctgcagtgctagaga TRBV23-1:
atgggcaccaggctcctcggctgtgcagccctgtgtctcctggcagcagactcttttcatgccaaagtcacacagactccaggacattt
ggtcaaaggaaaaggacagaaaacaaagatggattgtaccccgaaaaaggacatactttgtttattggtatcaacagaatcagaata
aagagtttatgcttttgatttcctttcagaatgaacaagttcttcaagaaacggagatgcacaagaagcgattctcatctcaatgccccaag
aacgcaccctgcagcctggcaatcctgtcctcagaaccgggagacacggcactgtatctctgcgccagcagtcaatc TRBV24-1:
atggcctccctgctcttcttctgtggggccttttatctcctgggaacaggggtccatggatgctgatgttacccagaccccaaggaatagga
tcacaaagacaggaaagaggattatgctggaatgttctcagactaagggtcatgatagaatgtactggtatcgacaagacccaggact
gggcctacggttgatctattactcctttgatgtcaaagatataaacaaggagagatctctgatggatacagtgtctctcgacaggcaca
ggctaaattctccctgtccctagagtctgccatccccaaccagacagctctttacttctgtgccaccagtgatttg TRBV25-1:
atgactatcaggctcctctgctacatgggcttttattttctgggggcaggcctcatggaagctgacatctaccagaccccaagataccttg
ttatagggacaggaaagaagatcactctggaatgttctcaaaccatgggccatgacaaaatgtactggtatcaacaagatccaggaatg
gaactacacctcatccactattcctatggagttaattccacagagaagggagatctttcctctgagtcaacagtctccagaataaggacg
gagcattttcccctgaccctggagtctgccaggccctcacatacctctcagtacctctgtgccagcagtgaata TRBV27:
atgggccccccagctccttggctatgtggtcctttgccttctaggagcaggcccctggaagcccaagtgacccagaacccaagatacc
tcatcacagtgactggaaagaagttaacagtgacttgttctcagaatatgaaccatgagtatatgtcctggtatcgacaagacccagggc
tgggcttaaggcagatctactattcaatgaatgttgaggtgactgataagggagatgttcctgaagggtacaaagtctctcgaaaagaga
agaggaatttccccctgatcctggagtcgcccagccccaaccagacctctctgtacttctgtgccagcagtttatc

Figure 8j

TRBV28:
atgggaatcaggctcctctgtcgtgtggccttttgtttcctggctgtaggcctcgtagatgtgaaagtaacccagagctcgagatatctag
tcaaaaggacgggagagaaagtttttctggaatgtgtccaggatatggaccatgaaaatatgttctggtatcgacaagacccaggtctg
gggctacggctgatctatttctcatatgatgttaaaatgaaagaaaaaggagatattcctgaggggtacagtgtctctagagagaagaag
gagcgcttctccctgattctggagtccgccagcaccaaccagacatctatgtacctctgtgccagcagtttatg TRBV29-1:
Atgctgagtcttctgctccttctcctgggactaggctctgtgttcagtgctgtcatctctcaaaagccaagcagggatatctgtcaacgtg
gaacctccctgacgatccagtgtcaagtcgatagccaagtcaccatgatgttctggtaccgtcagcaacctggacagagcctgacact
gatcgcaactgcaaatcagggctctgaggccacatatgagagtggatttgtcattgacaagtttcccatcagccgcccaaacctaacatt
ctcaactctgactgtgagcaacatgagccctgaagacagcagcatatatctctgcagcgttgaaga TRBV30:
atgctctgctctctccttgcccttctcctgggcactttctttgggggtcagatctcagactattcatcaatggccagcgaccctggtgcagcct
gtgggcagcccgctctctctggagtgcactgtggagggaacatcaaacccaacctatactggtaccgacaggctgcaggcaggggg
cctccagctgctcttctactccgttggtattggccagatcagctctgaggtgccccagaatctctcagcctccagaccccaggaccggc
agttcatcctgagttctaagaagctccttctcagtgactctggcttctatctctgtgcctggagtgt

Figure 9a atgaaggaggtggagcagaattctggacccctcagtgttccagagggagccattgcct
ctctcaactgcacttacagtgaccgaggttcccagtccttcttctggtacagacaata
ttctgggaaaagccctgagttgataatgttcatatactccaatggtgacaaagaagat
ggaaggtttacagcacagctcaataaagccagccagtatgtttctctgctcatcagag
actcccagcccagtgattcagccacctacctctgtgccgtgaagggggggtctggggg
ttaccagaaagttacctttggaactggaacaaagctccaagtcatcccaaatatccag
aacccggatcctgccgtgtaccagctgagagactctaaatccagtgacaagtctgtct
gcctattcaccgatttgattctcaaacaaatgtgtcacaaagtaaggattctgatgt
gtatatcacagacaaatgtgtgctagacatgaggtctatggacttcaagagcaacagt
gctgtggcctggagcaacaaatctgactttgcatgtgcaaacgccttcaacaacagca
ttattccagaagacaccttcttccccagcccagaaagttcctaa

Figure 9b atgggcgtcatgcagaacccaagacacctggtcaggaggaggggacaggaggcaagac
tgagatgcagcccaatgaaaggacacagtcatgtttactggtatcggcagctcccaga
ggaaggtctgaaattcatggtttatctccagaaagaaaatatcatagatgagtcagga
atgccaaaggaacgatttctgctgaatttcccaaagagggccccagcatcctgagga
tccagcaggtagtgcgaggagattcggcagcttatttctgtgccagctcaccacagac
aggggcacagatacgcagtattttggcccaggcaccggctgacagtgctcgaggac
ctgaaaaacgtgttcccacccgaggtcgctgtgtttgagccatcagaagcagagatct
cccacacccaaaaggccacactggtgtgcctggccacaggcttctaccccgaccacgt
ggagctgagctggtgggtgaatgggaaggaggtgcacagtgggtctgcacagacccg
cagcccctcaaggagcagcccgccctcaatgactccagatacgctctgagcagccgcc
tgagggtctcggccaccttctggcaggaccccgcaaccacttccgctgtcaagtcca
gttctacgggctctcggagaatgacgagtggacccaggatagggccaaacccgtcacc
cagatcgtcagcgccgaggcctggggtagagcagactaa

Figure 10a

MKEVEQNSGPLSVPEGAIASLNCTYSDRGSQSFFWYRQYSGK
SPELIMFIYSNGDKEDGRFTAQLNKASQYVSLLIRDSQPSDSA
TYLCAVKGGSGGYQKVTFGTGTKLQVIPNIQNPDPAVYQLR
DSKSSDKSVCLFTDFDSQTNVSQSKDSDVYITDKCVLDMRSM
DFKSNSAVAWSNKSDFACANAFNNSIIPEDTFFPSPESS Stop

Figure 10b

MGVMQNPRHLVRRRGQEARLRCSPMKGHSHVYWYRQLPEE
GLKFMVYLQKENIIDESGMPKERFSAEFPKEGPSILRIQQVVR
GDSAAYFCASSPQTGGTDTQYFGPGTRLTVLEDLKNVFPPEV
AVFEPSEAEISHTQKATLVCLATGFYPDHVELSWWVNGKEV
HSGVCTDPQPLKEQPALNDSRYALSSRLRVSATFWQDPRNHF
RCQVQFYGLSENDEWTQDRAKPVTQIVSAEAWGRAD Stop

CELLS EXPRESSING MODIFIED T CELL RECEPTOR

RELATED APPLICATIONS AND INCORPORATION BY REFERENCE

This application is a division of U.S. application Ser. No. 11/597,252 filed Apr. 28, 2009, now U.S. Pat. No. 8,361,794, which is a National Stage application of co-pending PCT application PCT/GB2005/002570 filed Jun. 29, 2005, which was published in English under PCT Article 21(2) on Jan. 5, 2006, and which claims the benefit of Great Britain patent applications Serial No. GB 0414499.4 filed Jun. 29, 2004; Serial No. 0421831.9 filed Oct. 1, 2004; and Serial No. 0511123.2 filed Jun. 1, 2005. These applications are incorporated herein by reference in their entireties.

REFERENCE TO A SEQUENCE LISTING

This application incorporates by reference the contents of a 80.6 kb text file created on Oct. 29, 2009 and named "SN11597252_sequencelisting.txt, which is the sequence listing for this application.

FIELD OF THE INVENTION

The present invention relates to cells, particularly T cells, expressing modified T cell receptors (TCRs), their preparation, and their use in therapy.

BACKGROUND TO THE INVENTION

Native TCRs

As is described in, for example, WO 99/60120 TCRs mediate the recognition of specific Major Histocompatibility Complex (MHC)-peptide complexes by T cells and, as such, are essential to the functioning of the cellular arm of the immune system.

Antibodies and TCRs are the only two types of molecules which recognise antigens in a specific manner, and thus the TCR is the only receptor for particular peptide antigens presented in MHC, the alien peptide often being the only sign of an abnormality within a cell. T cell recognition occurs when a T-cell and an antigen presenting cell (APC) are in direct physical contact, and is initiated by ligation of antigen-specific TCRs with pMHC complexes.

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands are also immunoglobulin superfamily proteins but are specialised for antigen presentation, with a highly polymorphic peptide binding site which enables them to present a diverse array of short peptide fragments at the APC cell surface.

Two further classes of proteins are known to be capable of functioning as TCR ligands. (1) CD1 antigens are MHC class I-related molecules whose genes are located on a different chromosome from the classical MHC class I and class II antigens. CD1 molecules are capable of presenting peptide and non-peptide (eg lipid, glycolipid) moieties to T cells in a manner analogous to conventional class I and class II-MHC-pep complexes. See, for example (Barclay et al, (1997) The Leucocyte Antigen Factsbook $2^{nd}$ Edition, Academic Press) and (Bauer (1997) Eur J Immunol 27 (6) 1366-1373)) (2) Bacterial superantigens are soluble toxins which are capable of binding both class II MHC molecules and a subset of TCRs. (Fraser (1989) Nature 339 221-223) Many superantigens exhibit specificity for one or two Vbeta segments, whereas others exhibit more promiscuous binding. In any event, superantigens are capable of eliciting an enhanced immune response by virtue of their ability to stimulate subsets of T cells in a polyclonal fashion.

The extracellular portion of native heterodimeric αβ and γδ TCRs consist of two polypeptides each of which has a membrane-proximal extracellular constant domain, and a membrane-distal variable region. Each of the extracellular constant domain and variable region includes an intra-chain disulfide bond. The variable regions contain the highly polymorphic loops analogous to the complementarity determining regions (CDRs) of antibodies. CDR3 of αβ TCRs interact with the peptide presented by MHC, and CDRs 1 and 2 of αβ TCRs interact with the peptide and the MHC. The diversity of TCR sequences is generated via somatic rearrangement of linked variable (V), diversity (D), joining (J), and constant genes, the genes products thereof making up the variable region.

Functional α and γ chain polypeptides are formed by rearranged V-J-C domains, whereas β and δ chains consist of V-D-J-C domains. (See FIG. 1) Each functional TCR possessing one of the possible variants of each domain. (See FIGS. 7 and 8 for the DNA sequences of all known TCR C and V domains from TCR α and β chains respectively, also see (LeFranc et al, (2001) The T cell receptor Factsbook, Academic Press) for a complete listing of the DNA and amino acid sequences of all known TCR domains) A further level of diversity is introduced to αβ TCRs by the in-vivo recombination of shortened TCR domains. The extracellular constant domain has a membrane proximal motif and an immunoglobulin motif. There are single α and δ chain constant domains, known as TRAC and TRDC respectively. The β chain constant domain is composed of one of two different β constant domains, known as TRBC1 and TRBC2 (IMGT nomenclature). There are four amino acid changes between these β constant domains, three of which are in exon 1 of TRBC1 and TRBC2: $N_4K_5$->$K_4N_5$ and $F_{37}$->Y, the final amino acid change between the two TCR β chain constant regions being in exon 3 of TRBC1 and TRBC2: $V_1$->E. (IMGT numbering, differences TRBC1->TRBC2) The constant γ domain is composed of one of either TRGC1, TRGC2(2x) or TRGC2(3x). The two TRGC2 constant domains differ only in the number of copies of the amino acids encoded by exon 2 of this gene that are present. TCR constant domains include a transmembrane sequence, the amino acids of which anchor the TCR chains into the cell surface membrane. There are 46 different TRAV domains and 56 TRBV domains. 52 different functional genes encode the TRAJ domains, whereas 12-13 functional genes encode the TRBJ domains. 2 different functional genes encode the TRBD domains.

The extent of each of the TCR extracellular constant domains, bounded by the transmembrane sequences, is somewhat variable. However, a person skilled in the art can readily determine the position of the domain boundaries using a reference such as The T Cell Receptor Facts Book, Lefranc & Lefranc, Publ. Academic Press 2001.

Immunotherapy

Immunotherapy involves enhancing the immune response of a patient to cancerous or infected cells. Active immunotherapy is carried out by stimulation of the endogenous immune system of tumour bearing patients. Passive, or adoptive, immunotherapy involves the transfer of immune competent cells into the patient. (Paul (2002) Curr Gene Therapy 2 91-100) There are three broad approaches to adoptive immunotherapy which have been applied in the clinic for the treatment of metastatic diseases; lymphokine-activated killer (LAK) cells, auto-lymphocyto therapy (ALT) and tumour-infiltrating lymphocutes (TIL). (Paul (2002) *Curr Gene Therapy* 2 91-100).

A recent proposed variation of T cell adoptive therapy is the use of gene therapy techniques to introduce TCRs specific for known cancer-specific MHC-peptide complexes into the T cells of cancer patients. For example, (WO 01/55366) discloses retrovirus-based methods for transfecting, preferably, T cells with heterologous TCRs. This document states that these transfected cells could be used for either the cell surface display of TCR variants as a means of identifying high affinity TCRs or for immunotherapy. Methods for the molecular cloning of cDNA of a human p53-specific, HLA restricted murine TCR and the transfer of this cDNA to human T cells are described in published US patent application no. 20020064521. This document states that the expression of this murine TCR results in the recognition of endogenously processed human p53 expressed in tumour cells pulsed with the p53-derived peptide 149-157 presented by HLA A*0201 and claims the use of the murine TCR in anti-cancer adoptive immunotherapy. However, the concentration of peptide pulsing required achieving half maximal T cell stimulation of the transfected T cells was approximately 250 times that required by T cells expressing solely the murine TCR. As the authors noted "The difference in level of peptide sensitivity is what might be expected of a transfectant line that contained multiple different TCR heterodimers as a result of independent association of all four expressed hu and mu TCR chains."

There are also a number of recent papers relating to T cell adoptive therapy. In one study (Rosenberg (1988) *N Engl J Med* 319 (25) 1676-80) lymphocytes from melanomas were expanded in vitro and these tumor-infiltrating lymphocytes, in combination with IL-2 were used to treat 20 patients with metastatic melanoma by means of adoptive transfer. The authors note that objective regression of the cancer was observed in 9 of 15 patients (60 percent) who had not previously been treated with interleukin-2 and in 2 of 5 patients (40 percent) in whom previous therapy with interleukin-2 had failed. Regression of cancer occurred in the lungs, liver, bone, skin, and subcutaneous sites and lasted from 2 to more than 13 months. A further study describes the administration of an expanded population of Melan-A specific cytotoxic T cells to eight patients with refractory malignant melanoma. These T cells were administered by i.v. infusion at fortnightly intervals, accompanied by s.c. administration of IL-2. The T cell infusions were well tolerated with clinical responses noted as one partial, one mixed with shrinkage of one metastatic deposit and one no change (12 months) among the eight patients. (Meidenbauer (2003) *J Immunol* 170 2161-2169) As noted in this study, recent advances regarding the in vitro stimulation T cells for the generation of cell populations suitable for T cell adoptive therapy have made this approach more practical. See, for example (Oelke (2000) *Clin Cancer Res* 6 1997-2005) and (Szmania (2001) *Blood* 98 505-12).

SUMMARY OF THE INVENTION

The present invention relates to cells presenting at least one T cell receptor (TCR) anchored to the membrane by a transmembrane sequence, said TCR comprising an interchain disulfide bond between extracellular constant domain residues which is not present in native TCRs. Such T cells are expected to be particularly suited for use in T cell adoptive immunotherapy.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 illustrates the domains that comprise TCR α and β chains: wherein "S" denotes the signal peptide, "V" denotes the variable domain, "J" denotes the joining domain, D denotes the diversity domain, and "C" denotes the constant domain which contains the transmembrane sequence;

FIGS. 3a and 3b show respectively the nucleic acid sequences of the a (SEQ ID NO:34) and β (SEQ ID NO:35) chains of a soluble A6 TCR, mutated so as to introduce a cysteine codon. The shading indicates the introduced cysteine codons;

FIG. 4a shows the amino acid sequence (SEQ ID NO:36) encoded by the DNA sequence of FIG. 3a, including the $T_{48}{\rightarrow}C$ mutation (underlined) used to produce the novel disulfide inter-chain bond, and FIG. 4b shows the amino acid sequence (SEQ ID NO:37) encoded by the DNA sequence of FIG. 3b, including the $S_{57}{\rightarrow}C$ mutation (underlined) used to produce the novel disulfide inter-chain bond;

FIG. 5 graphically illustrates the PCR reactions required to produce a DNA sequence encoding a full-length disulfide-linked A6 Tax TCR using DNA encoding soluble disulfide-linked A6 Tax TCR and wild-type A6 Tax TCR as templates;

FIG. 6a shows the nucleic acid (SEQ ID NO:38) and protein sequences (SEQ ID NO:39) of the membrane anchored α chain of A6 TCR, mutated so as to introduce a new cysteine codon and mutate the Cys involved in forming the native inter-chain disulfide bridge to Ser. The first shading indicates the introduced cysteine codon; the underlined Ser codon indicates the position of the Cys->Ser mutation disrupting the capacity to form the native inter-chain disulfide link.

FIG. 6b shows nucleic acid (SEQ ID NO:40) and protein sequences (SEQ ID NO:41) of the membrane anchored β chain of A6 TCR, using the native constant domain, TRBC2 (nomenclature according to the IMGT format as described in (LeFranc et al, (2001) The T cell receptor Factsbook, Academic Press), mutated so as to introduce a new cysteine codon and mutate the Cys involved in forming the native inter-chain disulfide bridge to Ser. The first shading indicates the introduced cysteine codon; the underlined Ser codon indicates the position of the Cys->Ser mutation disrupting the capacity to form the native inter-chain di-sulfide link.

FIGS. 7a-7h detail the DNA sequence of all known TCR α chain constant and variable domains (SEQ ID NOS: 41-89.

FIGS. 8a-8j detail the DNA sequence of all known TCR β chain constant and variable domains SEQ ID NOS:90-145.

FIGS. 9a and 9b show respectively the DNA sequences of the α (SEQ ID NO:146) and β (SEQ ID NO:147) chains of a soluble AH-1.23 TCR, mutated so as to introduce a novel cysteine codon (indicated by shading).

FIGS. 10a and 10b show respectively the AH-1.23 TCR α (SEQ ID NO:148) and P (SEQ ID NO:149) chain extracellular amino acid sequences produced from the DNA sequences of FIGS. 9a and 9b.

DETAILED DESCRIPTION OF THE INVENTION

Figure 2:
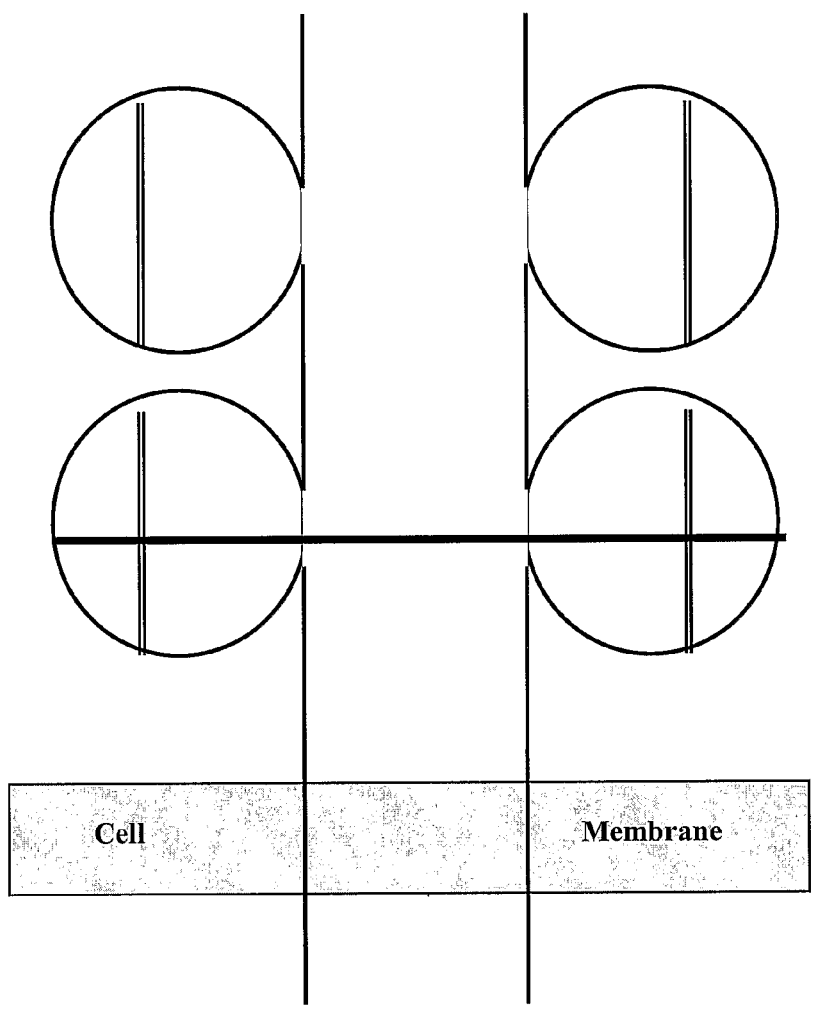
FIG. 2 illustrates the structure of a cell surface TCR containing a non-native interchain disulfide bond.

This invention provides a cell presenting at least one T cell receptor (TCR) anchored to the membrane by a transmembrane sequence, said TCR comprising an interchain disulfide bond between extracellular constant domain residues which is not present in native TCRs.

As noted above native TCRs exist in αβ and γδ forms, the present invention encompasses cells presenting either of these TCR forms, wherein said TCR comprises an interchain disulfide bond between extracellular constant domain residues which is not present in native TCRs.

Another embodiment provides a cell presenting at least one αβ T cell receptor (TCR) anchored to the membrane by a transmembrane sequence, said TCR comprising a disulfide bond between α and β extracellular constant domain residues which is not present in native TCRs.

The presence of the novel cysteine residues (creating the novel disulfide bond) in the transfected heterodimeric TCR (dTCR) chains favour the production of the desired transfected TCRs over TCRs comprising a native TCR chain associated with a transfected TCR chain. Without wishing to be bound by theory, this result is interpreted as being due to the two transfected TCR chains preferentially self-associating due to the formation of the novel inter-chain disulfide bond between the introduced cysteine residues. The formation of any TCR comprising a mismatched pair of TCR chains (one native and one from the transfected TCR) may be further inhibited by ensuring the transfected chains lack the cysteine residue involved in the formation of the native inter-chain disulfide bond. Cells expressed such transfected TCR chains therefore provide a preferred embodiment of the invention.

Use of a single chain TCR (scTCR) in accordance with the invention also avoids formation of mismatched pairs.

The αβ TCRs which comprise a disulfide bond between α and β extracellular constant domain residues which is not present in native TCRs presented by the cells of the invention are targeting moieties. The TCRs of the invention target TCR ligands such as peptide-MHC or CD1-antigen complexes. As such, it would be desirable if the affinity of these TCR could be altered. For example it may be desirable if these TCR had a higher affinity and/or a slower off-rate for the TCR ligands than native TCRs specific for that ligand. The inventors co-pending application WO 2004/044004 details methods of producing and testing TCRs having a higher affinity and/or a slower off-rate for the TCR ligand than native TCRs specific for that ligand.

The TCR functionality of cells transfected to express and present the membrane anchored scTCRs and dTCRs may be tested by confirming that transfected cells bind to the relevant TCR ligand (pMHC complex, CD1-antigen complex, superantigen or superantigen/pMHC complex)—if it binds, then the requirement is met. The binding of the transfected cells to a TCR ligand can be detected by a number of methods. These include attaching a detectable label to the TCR ligand. For example, where the method uses pMHC tetramers, the pMHC may include a fluorescent label. Example 6 herein provides a detailed description of the methods required to analyse the binding of cells transfected to express disulfide-linked TCRs to MHC-peptide complexes. This method is equally applicable to the study of TCR/CD1 interactions. In order to apply this method to the study of TCR/CD1 interactions soluble forms of CD1 are required, the production of which are described in (Bauer (1997) *Eur J Immunol* 27 (6) 1366-1373).

The Cell Membrane Anchored dTCR

In the case of a dTCR, the TCR □ and □ chains may each comprise a transmembrane sequence, fused at its N terminus to an extracellular constant domain sequence, in turn fused at its N terminus to a variable region sequence. Furthermore, at least the said sequences of the TCR α and β chains other than the complementarity determining regions of the variable region, may correspond to human TCR α and β sequences.

The Cell Membrane Anchored scTCR

In the case of an scTCR, the scTCR comprises
(i) a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and a linker sequence linking the C terminus of the first segment to the N terminus of the second segment, or
(ii) a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and a linker sequence linking the C terminus of the first segment to the N terminus of the second segment.

Again, in the scTCR embodiment, the said sequences of the TCR α and β chains other than the complementarity determining regions of the variable region, correspond to human TCR α and β sequences.

Linker in the Membrane Anchored scTCR Polypeptide

For the cell presented scTCRs of the present invention, a linker sequence links the first and second TCR segments, to form a single polypeptide strand. The linker sequence may, for example, have the formula -P-AA-P- wherein P is proline and AA represents an amino acid sequence wherein the amino acids are glycine and serine.

For the cell presented scTCRs of the present invention to bind to a TCR ligand, such as MHC-peptide or CD1-antigen complexes, the first and second segments must be paired so that the variable region sequences thereof are orientated for such binding. Hence the linker should have sufficient length to span the distance between the C terminus of the first segment and the N terminus of the second segment, or vice versa. On the other hand excessive linker length should preferably be avoided, in case the end of the linker at the N-terminal variable region sequence blocks or reduces bonding of the scTCR to the target ligand.

For example, in the case where the constant region extracellular sequences present in the first segment correspond to the constant regions of the α and β chains of a native TCR truncated at their C termini such that the cysteine residue that forms the native interchain disulfide bond of the TCR is excluded, and the linker sequence links the C terminus of the first segment to the N terminus of the second segment, the linker may consist of from 26 to 41, for example 29, 30, 31 or 32 amino acids, and a particular linker has the formula -PGGG-(SGGGG)$_5$-P- wherein P is proline, G is glycine and S is serine (SEQ ID NO:1).

The Cell Membrane Anchored scTCR and dTCR

As mentioned above, preferred embodiments the dTCR or scTCR α and β chain sequences correspond to human TCR α and β sequences, with the exception of the complementarity determining regions (CDRs) of the variable regions which may or may not correspond to human CDR sequences. However, correspondence between such sequences need not be 1:1 on an amino acid level. N- or C-truncation, and/or amino acid deletion and/or substitution relative to corresponding human TCR sequences is acceptable, provided the overall result is a cell membrane anchored TCR comprising mutual orientation of the α and β variable region sequences is as in native αβ T cell receptors respectively. In particular, because the constant domain extracellular sequences are not directly involved in contacts with the ligand to which the cell membrane anchored scTCR or dTCR binds, they may be shorter than, or may contain substitutions or deletions relative to, extracellular constant domain sequences of native TCRs.

Included in the scope of this invention are cells presenting membrane anchored TCRs comprising amino acids encoded by any appropriate combination of the nucleic acid sequences corresponding to those disclosed in FIGS. 7 and 8. As is known to those skilled in the art, TCRs can also be produced by combination of amino acid sequences encoded by truncated variants of the sequences disclosed in FIGS. 7 & 8. Such TCRs form an additional embodiment of the present invention. Also included within the scope of this invention are membrane anchored TCRs encoded by any variants of these nucleic acid molecules.

Usually, cells according to the invention will present a plurality of the said scTCR or dTCR (the exogenous TCRs). Each of the plurality of the said scTCRs or dTCRs is preferably identical, but if the cell is a T-cell, it may also present some native (endogenous) TCRs, residually encoded by the T cell chromosomes.

Another preferred embodiment provides T cells having the said membrane anchored scTCR or dTCR, or a plurality thereof. In a further preferred embodiment these T cells are cytotoxic T cells.

Another preferred embodiment provides cells that reduces the cellular or pro-inflammatory arms of an auto-immune response having the said membrane anchored scTCR or dTCR, or a plurality thereof. Examples of such cells, include, but are not limited to macrophages, γδ T cells, Th3 T cells, Tr1 T cells, NK T cells, macrophages and regulatory T cells. In a further preferred embodiment these cells are regulatory T cells.

Regulatory T cells are characterised by the cell-surface expression of CD4 and CD25. (Bluestone and Tang *Proc Natl Acad Sci USA*. 2004 101 Suppl 2: 14622-6.) provides a review of regulatory T cells.

In a further embodiment of the invention the cells present scTCR or dTCR which contains a covalent disulfide bond linking a residue of the immunoglobulin region of the constant domain of the α chain to a residue of the immunoglobulin region of the constant domain of the β chain.

A further embodiment of the invention provides a cell presenting scTCR or dTCR wherein in the said TCR an interchain disulfide bond in native TCR is not present.

A further embodiment of the invention provides a cell presenting scTCR or dTCR wherein in the said TCR cysteine residues which form the native interchain disulfide bond are substituted to another residue.

A further embodiment of the invention provides a cell presenting scTCR or dTCR wherein in the said TCR cysteine residues which form the native interchain disulfide bond are substituted to serine or alanine.

A further embodiment of the invention provides a cell presenting scTCR or dTCR wherein in the said TCR an unpaired cysteine residue present in native TCR β chain is not present.

Inter-Chain Disulfide Bond

A principal characterising feature of the cell membrane anchored scTCRs and dTCRs of the present invention, is a disulfide bond between the constant region extracellular sequences of the dTCR polypeptide pair or first and second segments of the scTCR polypeptide. That bond may correspond to the native inter-chain disulfide bond present in native dimeric αβ TCRs, or may have no counterpart in native TCRs, being between cysteines specifically incorporated into the constant region extracellular sequences of dTCR polypeptide pair or first and second segments of the scTCR polypeptide. In some cases, both a native and a non-native disulfide bond may be desirable.

The position of the disulfide bond is subject to the requirement that the variable region sequences of dTCR polypeptide pair or first and second segments of the scTCR polypeptide are mutually orientated substantially as in native αβ T cell receptors.

The disulfide bond may be formed by mutating non-cysteine residues on the first and second segments to cysteine, and causing the bond to be formed between the mutated residues. Residues whose respective β carbons are approximately 6 Å (0.6 nm) or less, and preferably in the range 3.5 Å (0.35 nm) to 5.9 Å (0.59 nm) apart in the native TCR are preferred, such that a disulfide bond can be formed between cysteine residues introduced in place of the native residues. It is preferred if the disulfide bond is between residues in the constant immunoglobulin region, although it could be between residues of the membrane proximal region. Preferred sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 48 | Ser 57 | 0.473 |
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

Now that the residues in human TCRs which can be mutated into cysteine residues to form a new interchain disulfide bond in cell membrane bound dTCRs or scTCRs according to the invention have been identified, those of skill in the art will be able to mutate TCRs of other species in the same way to produce a dTCR or scTCR of that species for cell membrane bound expression. In humans, the skilled person merely needs to look for the following motifs in the respective TCR chains to identify the residue to be mutated (the shaded residue is the residue for mutation to a cysteine).

```
αChain Thr 48:   DSDVYITDKTVLDMRSMDFK  (amino acids 39-58 of exon 1
                 of the TRAC*01 gene)  (SEQ ID NO: 2)

αChain Thr 45:   QSKDSDVYITDKTVLDMRSM  (amino acids 36-55 of exon 1
                 of the TRAC*01 gene)  (SEQ ID NO: 3)

αChain Tyr 10:   DIQNPDPAVYQLRDSKSSDK  (amino acids 1-20 of exon 1
                 of the TRAC*01 gene)  (SEQ ID NO: 4)

αChain Ser 15:   DPAVYQLRDSKSSDKSVCLF  (amino acids 6-25 of exon 1
                 of the TRAC*01 gene)  (SEQ ID NO: 5)
```

```
β Chain Ser 57:    NGKEVHSGVSTDPQPLKEQP (amino acids 48-67 of exon 1
                   of the TRBC1*01 & TRBC2*01 genes) (SEQ ID NO: 6)

β Chain Ser 77:    ALNDSRYALSSRLRVSATFW (amino acids 68-87 of exon 1
                   of the TRBC*01 & TRBC2*01 genes) (SEQ ID NO: 7)

β Chain Ser 17:    PPEVAVFEPSEAEISHTQKA (amino acids 8-27 of exon 1
                   of the TRBC1*01 & TRBC2*01 genes) (SEQ ID NO: 8)

β Chain Asp 59:    KEVHSGVSTDPQPLKEQPAL (amino acids 50-69 of exon 1
                   of the TRBC1*01 & TRBC2*01 genes gene) SEQ ID NO:
                   9)

β Chain Glu 15:    VFPPEVAVFEPSEAEISHTQ (amino acids 6-25 of exon 1
                   of the TRBC1*01 & TRBC2*01 genes (SEQ ID NO: 10)
```

In other species, the TCR chains may not have a region which has 100% identity to the above motifs. However, those of skill in the art will be able to use the above motifs to identify the equivalent part of the TCR α or β chain and hence the residue to be mutated to cysteine. Alignment techniques may be used in this respect. For example, ClustalW, available on the European Bioinformatics Institute website at www.e-bi.ac.uk/index.html can be used to compare the motifs above to a particular TCR chain sequence in order to locate the relevant part of the TCR sequence for mutation.

The present invention includes within its scope cell membrane bound αβ scTCRs and dTCRs, as well as those of other mammals, including, but not limited to, mouse, rat, pig, goat and sheep. As mentioned above, those of skill in the art will be able to determine sites equivalent to the above-described human sites at which cysteine residues can be introduced to form an inter-chain disulfide bond. For example, the following shows the amino acid sequences of the mouse Cα and Cβ soluble domains, together with motifs showing the murine residues equivalent to the human residues mentioned above that can be mutated to cysteines to form a TCR interchain disulfide bond (where the relevant residues are shaded):

```
Mouse Cα soluble domain:
                                          (SEQ ID NO: 11)
PYIQNPEPAVYQLKDPRSQDSTLCLFTDFDSQINVPKTMESGTFITDKTV

LDMKAMDSKSNGAIAWSNQTSFTCQDIFKETNATYPSSDVP

Mouse Cβ soluble domain:
                                          (SEQ ID NO: 12)
EDLRNVTPPKVSLFEPSKAEIANKQKATLVCLARGFFPDHVELSWWVNGR

EVHSGVSTDPQAYKESNYSYCLSSRLRVSATFWHNPRNHFRCQVQFHGLS

EEDKWPEGSPKPVTQNISAEAWGRAD

Murine equivalent of human α Chain Thr 48:
                                          (SEQ ID NO: 13)

ESGTFITDKTVLDMKAMDSK

Murine equivalent of human α Chain Thr 45:
                                          (SEQ ID NO: 14)

KTMESGTFITDKTVLDMKAM

Murine equivalent of human α Chain Tyr 10:
                                          (SEQ ID NO: 15)

YIQNPEPAVYQLKDPRSQDS

Murine equivalent of human α Chain Ser 15:
                                          (SEQ ID NO: 16)

AVYQLKDPRSQDSTLCLFTD

Murine equivalent of human β Chain Ser 57:
                                          (SEQ ID NO: 17)

NGREVHSGVSTDPQAYKESN

Murine equivalent of human β Chain Ser 77:
                                          (SEQ ID NO: 18)

KESNYSYCLSSRLRVSATFW

Murine equivalent of human β Chain Ser 17:
                                          (SEQ ID NO: 19)

PPKVSLFEPSKAEIANKQKA

Murine equivalent of human β Chain Asp 59:
                                          (SEQ ID NO: 20)

REVHSGVSTDPQAYKESNYS

Murine equivalent of human β Chain Glu 15:
                                          (SEQ ID NO: 21)

VTPPKVSLFEPSKAEIANKQ
```

A nucleic acid molecule or molecules comprising a sequence or sequences encoding a membrane anchored scTCR or dTCR are also provided, as are vectors comprising said nucleic acid molecules. Included in the scope of this invention are nucleic acid sequences encoding membrane anchored TCR comprising any appropriate combination of nucleic acid sequence corresponding to those disclosed in FIGS. 7 and 8. As is known to those skilled in the art, TCRs can also be produced that comprise combinations of amino acids encoded by truncated variants of the nucleic sequences disclosed in FIGS. 7 and 8, such nucleic acid sequences form an additional embodiment of the present invention. Also included within the scope of this invention are variants of these nucleic acid molecules that encode membrane anchored TCRs.

The nucleic acid or nucleic acids encoding TCRs of the invention may be provided in a form which has been adapted for expression in a prokaryote or eukaryote host cell. Suitable host cells include, but are not limited to, bacterial, yeast, mammalian or insect cells. For example, the host cell may be a human T cell or a human haematopoietic stem cell.

Such adapted nucleic acid or nucleic acids is/are mutated to reflect the codon preference of the host cell in to which it is introduced. The mutations introduced are silent mutations which do not affect the amino acid sequence of the polypeptide or polypeptides thereby encoded. GeneArt (Regensburg, Germany) offer a suitable nucleic acid optimisation service (GeneOptimizer™). WO 2004/059556, owned by GeneArt, provides further details of the optimisation process. Nucleic acid complementary to any such adapted nucleic acid sequence or a RNA sequence corresponding thereto also forms part of this invention. Furthermore, as will be obvious to those skilled in the art such nucleic acid or nucleic acids encoding TCRs of the invention may also comprise non-coding (intron) sequences.

As will be obvious to those skilled in the art such full-length TCR chain DNA sequences encode for the following sequences:
A leader sequence and the extracellular, transmembrane, and cytoplasmic TCR sequences.

A method for obtaining a cell expressing a membrane anchored scTCR or dTCR is also provided, said method comprises incubating a host cell harbouring a vector encoding the membrane anchored scTCR or dTCR under conditions causing expression of the scTCR or dTCR.

Preparation of Cells Expressing TCRs Comprising a Non-Native Disulfide Interchain Bond Another embodiment provides a method for the preparation of cells of the invention said method comprising:
(a) isolation of a population of cells, preferably a population of T cells
(b) in vitro transfection of said population of cells with an expression vector encoding a TCR of the invention specific for a target cell,
(c) optional in vitro growth of the transfected cells.

In a preferred embodiment the population of cells is isolated from a patient to be treated by a method of directing said cells to a population of target cells.

The following provides details of the isolation, transformation and optional in-vitro growth of T cells.

Isolation of T cells

T cells are found in both the bloodstream and lymphatic system. Generally, in order to obtain a suitable sample of T cells a venous blood sample is first obtained. In a preferred embodiment of the invention this blood sample is obtained from the patient requiring treatment.

The skilled person will be able to prepare a suitable sample of T cells for use in the present invention. For example, the sample may be whole blood, or a sample prepared from blood including, but not limited to, peripheral blood leucocytes (PBLs) or peripheral blood mononuclear cells (PBMC).

The T cells in the blood sample obtained are then be isolated by fluorescent activated cell sorting (FACS). Briefly, this involves the addition of florescent labels which specifically bind to T cell-specific 'marker' proteins and sorting the cells into populations based on the presence or absence of these labels. These fluorescent labels typically comprise an antibody, or fragment thereof, to which is attached a fluorescent moiety such as phycoerythicin (PE). The choice of label, or labels, used will determine the cell types present in the sorted populations:

| Label Used | Cell Population isolated |
| --- | --- |
| Anti CD3 fluorescent label | All (cytotoxic and helper) T cells |
| Anti CD8 fluorescent label | $CD8^+$ (cyto-toxic) T cells |
| Anti CD4 fluorescent label | $CD4^+$ (helper) T cells |
| Anti CD4 and anti CD25 fluorescent label | Regulatory T cells |

In Vitro Transfection T Cells with a Vector Encoding a TCR Specific for the Target Cell There are many techniques suitable for the transfection of mammalian cells, such as human T cells, that are known to those skilled in the art. Textbooks including the following provide experimental examples that describe the methods involved: Sambrook et al. *Molecular Cloning: A Laboratory Manual*, 2nd Ed., Cold Spring Harbor Laboratory, Cold Spring Harbor, N.Y., 1989; Ausubel et al. *Current Protocols in Molecular Biology*, John Wiley & Sons, New York, 1992; Glover *DNA Cloning, I and II*, Oxford Press, Oxford, 1985; B. D. Hames & S. J. Higgins *Nucleic Acid Hybridization* 1984; J. H. Miller and M. P. Calos, *Gene Transfer Vectors For Mammalian Cells*, Cold Spring Harbor Laboratory, Cold Spring Harbor, N.Y., 1987).

As stated above two recent patent applications are directed to the transfection of T cells with TCRs. (WO 01/55366 and US 20020064521) The methods disclosed in these applications are also applicable to the transfection of T cells with the TCRs of this invention that comprise a disulfide bond between residues not present in native TCRs. Briefly, WO 01/55366 discloses a retro-viral method for the introduction of TCRs with defined specificity into T cells. The application describes methods for the production of a retro-viral vector containing the α and β chains of a high affinity murine TCR specific for a nucleoprotein peptide (ASNENMDAM) (SEQ ID NO:22) presented by the murine class I MHC $H-2D^b$. This vector was then replicated in a human embryonic kidney cell line and the retroviral supernatant was collected to provide the material required for T cell transfection. US 20020064521 describes methods for the molecular cloning of cDNA of a human p53-specific, HLA restricted murine TCR and the transfer of this cDNA to human T cells. α and β chain TCR cDNAs were subcloned separately into a mammalian expression vector. This vector was then transferred into Jurkat cells using standard liposome transfection procedures. Surface expression Of the transfected TCR was then confirmed by flow cytometry.

In Vitro Growth of the Transfected T Cells

Once the T cells required for adoptive therapy have been transfected with the required TCR they can optionally be cultured in vitro to provide an expanded population of T cells using standard techniques.

One preferred method for the expansion of transfected T cells of the invention relies on the use of magnetic beads coated with the specific TCR ligand recognised by the introduced TCR, and a combination of anti CD28 and anti-CD3. Briefly, the use of these beads allows the selective expansion of T cells possessing functional transfected TCRs. The beads are commercially available in an anti-biotin coated form (Miltenyi Biotec, Bisley UK) which can then be coated with the biotinylated ligands of choice. (Example 9 herein details the required methodology)

Once the T cells have been prepared using the above methods they can be administered to patients together with a pharmaceutically acceptable carrier.

Administration of the Transfected Cells to the Patient

The invention provides a method of directing cells to a population of target cells in a patient, said method comprising administering to a patient a plurality of cells expressing a surface anchored TCR, wherein said TCR comprises a disulfide interchain bond between extracellular constant domain residues which is not present in native TCRs and wherein the TCR presented by such cells is specific for a TCR ligand on the population of target cells.

The invention also provides a method of directing a T cell response to a target cell phenotype in a patient, said method comprising administering to a patient a plurality of T cells expressing a surface anchored TCR, wherein said TCR comprises a disulfide interchain bond between extracellular constant domain residues which is not present in native TCRs and wherein the TCR presented by such T cells is specific for a TCR ligand on the target cell type.

In another embodiment of the invention the TCR ligand on the target cell type is a peptide-MHC complex or a CD1-antigen complex.

In a further embodiment of the invention the administered cells are not cytotoxic T cells.

In a further embodiment of the invention the target cell is a cancer cell or infected cell and the administered cells are cytotoxic T cells.

In a further embodiment of the invention the TCR ligand is unique to one tissue-type or to cells characteristic of one organ of the body.

In another embodiment of the invention the target cell is a target for auto-reactive T cells in autoimmune disease, organ rejection or Graft Versus Host Disease (GVHD). In a specific embodiment the target cells is an islet cell.

Examples of suitable MHC-peptide targets for the TCR according to the invention include, but are not limited to, viral epitopes such as HTLV-1 epitopes (e.g. the Tax peptide restricted by HLA-A2; HTLV-1 is associated with leukaemia), HIV epitopes, EBV epitopes, CMV epitopes; insulin and/or IGRP-derived diabetes epitopes; melanoma epitopes (e.g. MAGE-1 HLA-A1 restricted epitope) and other cancer-specific epitopes (e.g. the renal cell carcinoma associated antigen G250 restricted by HLA-A2). Further disease-associated pMHC targets, suitable for use in the present invention, are listed in the HLA Factsbook (Barclay (Ed) Academic Press), and many others are being identified.

In a further embodiment of the invention the population of T cells is isolated from a patient to be treated.

T cells expressing the transfected TCRs can be administered to the patients by a number of routes. For example, i.v. infusion at regular intervals, optionally accompanied by the administration of a cytokine such as IL-2.

A further embodiment of the invention provides an infusible or injectable pharmaceutical composition comprising a plurality of cells expressing a surface anchored TCR, said TCR comprises a disulfide bond between α and β extracellular constant domain residues which is not present in native TCRs together with a pharmaceutically acceptable carrier.

Such pharmaceutical compositions adapted for parenteral administration include aqueous and non-aqueous sterile injection formulations which may contain suspending agents, anti-oxidants, buffers, bacteriostats and solutes which render the formulation substantially isotonic with the blood of the intended recipient.

Dosages of the cells of the present invention can vary between wide limits, depending upon the disease or disorder to be treated, the age and condition of the individual to be treated, etc. and a physician will ultimately determine appropriate dosages to be used. For example, a effective dosage may vary between $10^5$ to $10^{10}$ cells/kg body weight. The practice of therapeutic administration by infusion is described in a number of papers. See, for example (Rosenberg 1988 New Eng. J Med 319 1676-1680). The dosage may be repeated as often as appropriate. If side effects develop the amount and/or frequency of the dosage can be reduced, in accordance with normal clinical practice.

Additional Aspects

The invention provides a method of treatment of cancer, GVHD, infection, organ rejection, or auto-immune disease comprising administering a plurality of cells presenting at least one αβ T cell receptor (TCR) anchored to the membrane by a transmembrane sequence, said TCR comprising a disulfide interchain bond between extracellular constant domain residues which is not present in native TCRs. A specific embodiment is provided wherein the auto-immune disease is a disease selected from Rheumatoid Arthritis, Diabetes, Multiple Sclerosis or Reactive Arthritis Another aspect of the invention is provided by the use of a cell presenting at least one αβ T cell receptor (TCR) anchored to the membrane by a transmembrane sequence, said TCR comprising a disulfide interchain bond between extracellular constant domain residues which is not present in native TCRs in the preparation of a medicament for treatment of cancer, GVHD, infection, organ rejection, or auto-immune disease.

Cancers which may benefit the methods of the present invention include: leukaemia, head, neck, lung, breast, colon, cervical, liver, pancreatic, ovarian and testicular.

Auto-immune diseases which may benefit the methods of the following invention include:

Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune Neutrogena
Autoimmune thrombocytopenic purpura
Behçet's disease
Cerebellar degeneration
Chronic active hepatitis
Chronic inflammatory demyelinating polyradiculoneuropathy Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis Preferred features of each aspect of the invention are as for each of the other aspects mutatis mutandis. The prior art documents mentioned herein are incorporated to the fullest extent permitted by law.

The present invention will be further illustrated in the following Examples which are given for illustration purposes only and are not intended to limit the invention in any way.

EXAMPLES

The following example describes the preparation of the DNA sequences of FIGS. 3a and 3b. This example is usable for the preparation of the coding sequences of any given αβ TCR including a non-native disulfide interchain bond.

Example 1

Design of Primers and Mutagenesis of A6 Tax TCR α and β Chains to Introduce the Cysteine Residues Required for the Formation of a Novel Inter-Chain Disulfide Bond For mutating A6 Tax threonine 48 of exon 1 in TRAC*01 to cysteine, the following primers were designed (mutation shown in lower case):

```
                                            (SEQ ID NO: 23)
    5'-C ACA GAC AAA tgT GTG CTA GAC AT (SEQ ID NO: 24)
    5'-AT GTC TAG CAC Aca TTT GTC TGT G
```

For mutating A6 Tax serine 57 of exon 1 in TRBC1*01 or TRBC2*01 to cysteine, the following primers were designed (mutation shown in lower case):

```
                                            (SEQ ID NO: 25)
    5'-C AGT GGG GTC tGC ACA GAC CC (SEQ ID NO: 26)
    5'-GG GTC TGT GCa GAC CCC ACT G
```

PCR Mutagenesis:

Expression plasmids containing the genes for the A6 Tax TCR α or β chain were mutated using the α-chain primers or the β-chain primers respectively, as follows. 100 ng of plasmid was mixed with 5 µl 10 mM dNTP, 25 µl 10×Pfu-buffer (Stratagene), 10 units Pfu polymerase (Stratagene) and the final volume was adjusted to 240 µl with $H_2O$. 48 µl of this mix was supplemented with primers diluted to give a final concentration of 0.2 µM in 50 µl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 µl of the digested reaction was transformed into competent E. coli XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen mini-prep column according to the manufacturer's instructions and the sequence was verified by automated sequencing. The respective mutated nucleic acid and amino acid sequences are shown in FIGS. 3a and 4a for the α chain and FIGS. 3b and 4b for the β chain.

The following example describes the extension of the DNA of FIGS. 3a and 3b to add sequences coding for the remainder of the constant domains of the A6 TCR. Again, this example is usable for the extension of the constant domain encoding sequences of a corresponding soluble variant of any given αβ TCR.

Example 2

Design of A6 Tax TCR α and β Chain Nucleic Acid Sequences Required to Produce a Cell Surface Membrane Anchored A6 Tax TCR Including Cysteine Residues Required for the Formation of a Novel Inter-Chain Disulfide Bond The constructs encoding the α and β chains of a soluble disulfide-linked A6 Tax TCR molecule prepared as described in example 1 are used, along with cDNA from human peripheral blood mononuclear cells (PBMCs), in the production of constructs encoding the α and β chains of a membrane anchored A6 Tax TCR including cysteine residues required for the formation of a novel inter-chain disulfide bond. (Refer to FIG. 5 for a diagrammatic representation of the method involved).

TCR α chain DNA corresponding to Fragment 1 (See FIG. 5a) is amplified from cDNA encoding wild-type TRAY 12-2 TCR by PCR using the following primer pair specific for the TRAY 12-2 TCR signal peptide (Fwd primer) and the TRAY 12-2 TCR variable domain (Rev primer):

```
    5' Fwd α primer:
                                            (SEQ ID NO: 27)
    5'- ATG ATG AAA TCC TTG AGA GTTTT -3'
```

-continued

5' Rev α primer:
(SEQ ID NO: 28)
5'- GTA AGT GCA GTT GAGAGAGG -3'

TCR β chain DNA corresponding to Fragment 1 (See FIG. 5a) is amplified from cDNA encoding wild-type TRBV 6-5 TCR by PCR using the following primer pair specific for the TRBV 6-5 TCR signal peptide (Fwd primer) and the TRBV 6-5 TCR variable domain (Rev primer):

5' Fwd β primer:
(SEQ ID NO: 29)
5'- ATG AGC ATC GGC CTC CTG T -3'

5' Rev β primer:
(SEQ ID NO: 30)
5'- TT CAT ATC CTGGGC ACA CTG -3'

The above primers are designed to produce a PCR product that incorporates an overlap with the DNA encoding the variable region of the soluble disulfide-linked A6 Tax TCR produced in example 1.

TCR α chain DNA corresponding to Fragment 2 (See FIG. 5b) is amplified from cDNA from PBMC using the following primer pair specific for the 3' end of TRAC, this primer pair also introduces a Cys to Ser mutation disrupting the formation of the native inter-chain disulfide bond:

3' Fwd α primer:
(SEQ ID NO: 31)
5'- TC CCC AGC CCA GAA AGT TCC TCT GAT GTC

AAG CTG GTC GAG AAA AG -3'

3' Rev α primer:
(SEQ ID NO: 32)
5'- TTA GCT GGA CCA CAG CCG CAG -3'

TCR β chain DNA corresponding to Fragment 2 (See FIG. 5b) is amplified from cDNA from PBMC using the following primer pair specific for the 3' end of TRBC2, this primer pair also introduces a Cys to Ser mutation disrupting the formation of the native inter-chain disulfide bond:

3' Fwd β primer:
(SEQ ID NO: 33)
5'- CC GAG GCC TGG GGT AGA GCA GAC TCT GGC

TTC ACC TCC GAG TCT TAC C -3'

3' Rev β primer:
(SEQ ID NO: 34)
5'- TTA GCC TCT GGA ATC CTT TCT C- 3'

These primers are designed to produce a PCR product that incorporates an overlap with the DNA encoding the constant region of the soluble disulfide-linked A6 Tax TCR produced in example 1.

Final PCRs are required to assemble the entire genes for the two TCR-chains. For the alpha chain fragments 1 and 2 are mixed with the plasmid coding for the soluble alpha-chain and the full length coding region is amplified using the 5' Fwd a primer and the 3' Rev a primer with suitable restriction site sequences added to the primers as flanking sequences to facilitate sub-cloning in the required vector (for example, the retroviral pLXSN vector, BD Clontech, UK). The fragment is sub-cloned into the expression vector and sequenced.

For the beta chain fragments 1 and 2 are mixed with the plasmid coding for the soluble beta-chain and the full length coding region is amplified using the 5' Fwd β primer and the 3' Rev β primer with suitable restriction site sequences added to the primer as flanking sequences to facilitate sub-cloning into the required vector (for example, the retroviral pLXSN vector, BD Clontech, UK). The fragment is sub-cloned into the expression vector and sequenced.

FIGS. 6a and 6b show the nucleic acid and protein sequences of the membrane anchored α and β chain of A6 TCR respectively, mutated so as to introduce a new cysteine codon and mutate the cysteine residues involved in forming the native inter-chain disulfide bridge to Ser.

The above PCR reactions are all carried out using the following methodology.

For a 100 µl reaction mix:
1. 18 MO quality H2O to 100
2. 50 pmol Forward Primer
3. 50 pmol Reverse Primer
4. 2 µl 10 mM dNTP (10 mM each of dATP, dTTP, dCTP, dGTP).
5. 10 µl 10× Buffer (Pfu buffer for cloning purposes and Taq buffer for diagnostic PCR).
6. 5 units of enzyme (Pfu DNA Polymerase or Taq polymerase according to the particular application).

PCR program:
1. A denaturation step where the sample is heated to 94° for 10 minutes.
2. A number of cycles (20-40) including
   a denaturation step 1 minute @94°
   an annealing step 1 minute @45-60° (use the gradient block in PCR-1 if you need to establish the optimal annealing temperature).
   an elongation step 5-10 minutes @72-73°.
3. A final elongation step 10 minutes @72-73° to ensure that all products are full length
4. followed by a soak step at 4°.

The following example describes the preparation of the DNA sequences of FIGS. 9a and 9b. This example is usable for the preparation of the coding sequences of any given αβ TCR which includes a non-native disulfide interchain bond.

Example 3

Production of DNA Encoding a Soluble AH-1.23 TCR Comprising a Non-Native Disulfide Inter-Chain Bond Synthetic genes encoding the TCR α and TCR β chains of a soluble AH1.23 TCR can be manufactured to order. There are a number of companies which carry out this service such as GeneArt (Germany).

FIGS. 9a and 9b show respectively the DNA sequences of the α and β chains of a soluble AH-1.23 TCR, mutated so as to introduce a novel cysteine codon (indicated by shading).

FIGS. 10a and 10b show respectively the AH-1.23 TCR α and β chain extracellular amino acid sequences produced from the DNA sequences of FIGS. 9a and 9b The DNA sequences shown in FIGS. 9a and 9b can then be sub-cloned into the required vector containing the DNA sequences of FIGS. 3a and 3b respectively in such a way as to replace the DNA encoding the corresponding extracellular portions of the A6 TCR.

The following example describes a means of preparing DNA sequences encoding full-length TCRs containing a non-native disulfide interchain bond for use in the current invention. Preferably, said DNA sequences will comprise restriction enzyme recognition site to facilitate ligation of the sequences into the vector of choice. This example is usable for the production of any αβ or γδ TCR.

Example 4

Production of Nucleic Acids Encoding Alternative TCR α and β Chains of Membrane Anchored TCRs Including Cysteine Residues Required for the Formation of a Novel Inter-Chain Disulfide Bond To incorporate DNA encoding an alternative TCR into the vector(s) of choice synthetic genes encoding the required full-length TCR α and TCR β chains, altered in order to encode the required introduced cysteine residues in the constant domains thereof, can be manufactured to order. There are a number of companies which carry out this service such as GeneArt (Germany). Such DNA sequences can be produced which incorporate restriction enzyme recognition sequences to facilitate ligation of the DNA produced into the vector of choice.

For transfection of the desired cells with the expression vectors prepared according to example 6, selection of the appropriate vector is required:

Example 5

Vector Choice for the Transfection of T Cells with DNA Encoding TCRs Containing Cysteine Residues Required for the Formation of a Novel Inter-Chain Disulfide Bond As will be obvious to those skilled in the art the primary difference between transient and stable transfection methods is the choice of vector. The following table provides a summary of a number of vectors suitable for the transient transfection and/or stable transfection of T cells with DNA encoding TCRs containing cysteine residues required for the formation of a novel inter-chain disulfide bond:

| Vector and Supplier | Transient Expression | Random Stable Integration | Stable Site-Specific Integration | Stable Episomal Maintenance |
|---|---|---|---|---|
| pCI (Promega) | ✓ | ✓* | x | x |
| pCI$_{neo}$ (Promega) | ✓ | ✓* | x | x |
| pREP4 (Invitrogen) | ✓ | x | x | ✓ |
| pCEP4 (Invitrogen) | ✓ | x | x | ✓ |
| pcDNA5/FRT (Invitrogen) | ✓ | (✓) | ✓ | x |
| FRT Retroviral Vectors | ✓ | ✓ | ✓ | x |
| Standard Retroviral Vectors | ✓ | ✓ | x | x |

✓* Suitable when in combination with an appropriate vector (e.g. pCI$_{neo}$ with pCI).
(✓) Capable of random integration, but designed for site-specific integration into specialised recipient cells.

Ligation of the DNA sequences encoding a TCR containing a non-native disulfide interchain bond, prepared for example, as described in examples 1 and 2, or examples 3 or 4, into the desired vector or vectors is required. These vectors may be one of those listed in example 5. This example is usable for the ligation of the coding sequences of any given αβ or γδ TCR including a non-native disulfide interchain bond into the vector(s) of choice:

Example 6

Ligation of DNA Sequences Encoding a TCR Containing a Non-Native Disulfide Interchain Bond into the Desired Vector In order to facilitate the insertion of DNA encoding the TCR chains in the desired orientation into the vector or vectors of choice the vector(s) and DNA encoding the TCR chains should each have the same pair of different complementary ends. To achieve this the desired recipient vector or vectors, and the DNA sequences encoding the TCR chains are digested with the same appropriate pair of differing restriction enzymes. The cut DNA chains and the cut vector or vectors are then ligated using the Rapid DNA Ligation kit (Roche) following the manufacturers instructions.

Example 7 describes a general procedure for the isolation of T cell sub-populations for transformation to produce cells in accordance with the invention.

Example 7

Isolation of T Cell Sub Populations

PBMCs are isolated from venous blood samples using Leucosep® tubes (Greiner Bio-one, Germany) following the manufacturer's instruction. The isolated PBMCs are washed and used immediately. Freshly isolated PBMCs are washed twice in 10% autologous human serum/RPMI (Gibco BRL). Finally, the cells are re-suspended in RPMI medium.

T cell sub-populations are isolated from PBMCs by FACS using the relevant combination of antibodies in the table below for the T cell sub-population required and the following procedure:

| Label Used | Cell Population isolated |
|---|---|
| Anti CD3 fluorescent label | All (cytotoxic and helper) T cells |
| Anti CD8 fluorescent label | CD8$^+$ (cyto-toxic) T cells |
| Anti CD4 fluorescent label | CD4$^+$ (helper) T cells |
| Anti CD4 and anti CD25 fluorescent label | Regulatory T cells |

Under sterile conditions, the relevant fluorescently-labeled antibodies (0.01 mg/ml final concentration) are incubated with PBMCs (1×10$^7$/ml) for 30 mins at 37° C., 5% CO$_2$. Cells are then washed using medium (37° C.), centrifuged for 10 mins at 250×g and the supernatant discarded. The pellet is re-suspended and the cells are then bulk-sorted by FACS. The selected T cells are collected in either medium containing 10% autologous serum (for in-vitro culturing), or in the appropriate infusion medium, such as Hank's balanced buffer solution (Sigma, UK) with 10% autologous human serum albumin for immediate therapeutic use.

Alternatively, the required T cell sub-population may be isolated using magnetic beads coated with the same antibodies and antibody combinations described above.

Minimacs beads, produced by Miltenyi Biotech, are suitable for use in the isolation of T sub-populations and the manufacturer provides instructions for their use. This method "positively" selects and isolates the desired T cell sub-population. It is also possible to "negatively" select the desired T cell sub-population. This is achieved by coating the beads with a range of antibodies that will bind to all but the required T cell population in PBMCs.

Example 8 describes one method, usable in accordance with the invention, of modifying isolated cells for expression of TCRs containing a non-native disulfide interchain bond.

Example 8

Retro-Viral Transduction of T Cell with TCRs Containing Introduced Cysteine Residues Capable of Forming a Non-Native Disulfide Interchain Bond Primary T cells or T cell lines/clones are transduced with an appropriate retroviral vector, (e.g. the pLXSN retrovirus (BD ClonTech, UK)) following a T cell transduction methodology based on that described in (Clay (1999) *J Immunol* 163 507-513 and Bunnel (1995) *PNAS USA* 92 7739)

Production of Retroviral Supernatant

Briefly, in order to produce retroviral supernatant, the PG13 retrovirus producer cell line is transduced with the retroviral vector (pLXSN, BD Clontech, UK) produced in example 2 that contains DNA encoding the α and β chains of a membrane anchored A6 Tax TCR including cysteine residues required for the formation of a novel inter-chain disulfide bond. High titre clones are then isolated using standard techniques familiar to those skilled in the art. (See, for example (Miller (1991) *J Virol* 65 2220) A high titre clone is then grown to 80% confluence and the supernatant is then harvested.

Transduction of T Cells with Retroviral Supernatant

T cells are then re-suspended at $1\times10^6$ cells/ml in microtitre well plates in retroviral supernatant containing 8 μg/ml polybrene and 600 IU/ml IL-2. The plates are then centrifuged at 1000×g for 90 mins and incubated overnight at 37° C. in a humidified 5% $CO_2$ incubator. This transduction procedure is repeated after 2 days. The transduction procedure described in (Clay (1999) *J. Immunol.* 163 507-513) is then followed, thereby providing transfected T cells ready for in-vitro testing.

Example 9 describes a general method for enriching and enlarging a population of T cells in accordance with the invention. This method is not TCR specific.

Example 9

In-Vitro Growth of Transfected T Cells

After the transfection of T cells to express modified TCRs as described in Example 8 these T cells can, if necessary, be grown in-vitro to produce an enriched and enlarged populations of cells for in-vitro evaluation or therapeutic use using the following method.

Anti-biotin coated Clinimacs beads (Miltenyi Biotec, Germany) are coated with biotinylated anti-CD28 and anti-CD3 antibodies. 500,000 T cells and 500,000 autologous irradiated (33 Gy) APCs pulsed with the appropriate peptide (Tax peptide), are added to RPMI 1640 buffer containing 10-50 U/ml IL-2 and 10% autologous serum. $5\times10^6$/ml anti-CD28 and anti-CD3 antibody coated Clinibeads are then added to the cells.

The cells are then incubated under sterile conditions at 37° C., 5% $CO_2$ for 7 days. During this incubation period the buffer is replaced every 3 days. The cells can be re-stimulated the following week with the same ratio of beads to T-cells and fresh peptide-pulsed APCs. Once the required total number of transfected T cells has been reached the T cells are then re-suspended in the appropriate buffer for in-vitro evaluation or therapeutic use.

Example 10 describes one method of testing for successful cell surface expression of the desired TCRs on the chosen modified cell. This method is generally applicable, and not restricted to any particular cell surface TCR.

Example 10

Fluorescence Activated Cell Sorting (FACS)-Based Assay to Demonstrate Specific Binding of Cognate Peptide-MHC Complexes to T Cells Transfected to Express an A6 Tax TCR Incorporating Cysteine Residues Required for the Formation of a Novel Inter-Chain Disulfide Bond Preparation of T Cell Samples for Staining The transfected T cells are re-suspended in FACS staining buffer (2% FCS/PBS, at 37° C.) and counted. The cells are aliquoted into FACS tubes and pre-incubated at 37° C. for 5-10 minutes prior to staining.

Staining of T cells with HLA-A2 Tax Tetramers to Assess TCR-pMHC Binding

In order to stain the transfected T cells HLA-A2 Tax monomers are prepared using the methods described in WO 99/60120, and tetramerised using Phycoerythrin (PE)-labelled streptadivin via the methods described in (O'Callaghan (1999) *Anal Biochem* 266 9-15)

The following fluorescently labelled molecules are also used in the FACS assay as controls:

FITC-labelled isotype controls

PE-labelled "irrelevant" peptide-HLA-A2 tetramers

PE-labelled HLA-A2 Tax tetramer (48 μg) is incubated with $1\times10^6$ transfected T cells and 5 μg anti-CD8-FITC labelled antibody (or 5 μg anti-CD4-FITC labelled antibody) for 20 mins at 37° C. Cells are then washed using FACS buffer (37° C.), centrifuged for 10 mins at 250×g and the supernatant discarded.

After the wash, transfected T cells are re-suspended in 0.5 ml PBS. The T cell populations present in the samples are then analysed by flow cytometry.

Any T cells that are double-labelled by both the PE-HLA-A2 Tax tetramers and the αCD8-FITC labels (or anti-CD4-FITC labelled antibody) are $CD8^+$ T cells (or CD4+ T cells) expressing the transfected A6 Tax TCR.

The above HLA tetramer FACs staining method can be adapted to assess the expression level of any exogenous TCR on the surface of T cells by using tetramers of the cognate peptide-HLA for the desired exogenous TCR.

Staining of Transfected T Cells with Antibodies to Assess Exogenous TCR Expression As will be obvious to those skilled in the art there are other binding agent that can be utilised in such FACS methods, or any other suitable detection methods, for the assessment of exogenous TCR. The following table provides a summary of some antibodies suitable for this purpose:

| Antibody Specificity | Usage |
| --- | --- |
| Specific TCR variable domain (e.g. anti-Vβ30) | Assessment of exogenous TCR expression on T cells posessing an endogenous TCR of differing V domain usage |
| Pan TCR | Assessment of exogenous TCR expression on TCR- cells |

| Antibody Specificity | Usage |
|---|---|
| CD3 | Assessment of exogenous TCR expression on CD3− TCR− cells. The presence of the exogenous TCR should "rescue" cell surface CD3 presentation |

Example 11 describes one method of testing for successful cell surface expression of functional exogenous TCRs on the surface of a CTL. This method is specific for such CTL cells. However, the method is not limited to a specific TCR.

Example 11

Europium-Release Method for Assessing the Ability of CTL 'Killer' T Cells Transfected to Express the Membrane-Anchored A6 Tax TCR to Specifically Lyse Target Cells The following assay is used to assess the ability of CTLs transfected to express the membrane-anchored A6 Tax TCR to specifically lyse HLA-A*0201+ target cells.
The following mixtures are prepared for the assays:
Experimental wells: 50 µl of Transfected CTLs, 50 µl of media, 50 µl targets cells pulsed with the cognate HLA-A2 peptide.
Negative control wells: 50 µl of Transfected CTLs (effector cells), 50 µl of media, 50 µl targets cells pulsed with an irrelevant HLA-A2 peptide.
Background wells: APC Target cells are spun down after dilution to final concentration and the 50 µl of supernatant added to 100 µl media.
Spontaneous release wells: Target cells alone (no effector cells)+100 µl media
Maximum release wells: spontaneous release wells +15 µl of 10% Triton (Sigma T-9284)
Briefly, the above mixtures of effector and target cells are incubated for 2 to 4 hours and the Europium release assay is then carried out following the instructions supplied with the Delfia EuTDA Cytotoxicity Kit (Perkin Elmer).

Example 12 describes one method of testing for successful cell surface expression of functional exogenous TCRs on the surface of regulatory T cells or CTLs. The method is not limited to a specific TCR.

Example 12

Thymidine Incorporation Assay for Assessing the Ability of T Cells Transfected to Express the Membrane-Anchored AH1.23 TCR to Specifically Alter T Cell Proliferation $5 \times 10^6$ PMBCs are pulsed with 1 µM of the cognate peptide for the AH1.23 TCR and then cultured in RPMI 1640 medium at 37° C., 5% $CO_2$ for 14 days. A control group of $5 \times 10^6$ PMBCs cultured at 37° C., 5% $CO_2$ for 14 days without peptide pulsing. Both cultures are fed with 40 units/ml recombinant human IL-2 every 3 days.

The following are then added to $1 \times 10^5$ cells in a 96 well plate both the cultures prepared above:
$1 \times 10^5$ fresh autologous irradiated (33Gy) PBMCs, and a range (0 cells, $5 \times 10^4$, $1 \times 10^5$, $2 \times 10^5$, $5 \times 10^5$) of T cells transfected with the AH1.23 TCR using the methods described in the previous examples. These cultures are then incubated in RPMI 1640 medium for 3 days at 37° C., 5% $CO_2$.
1.85 MBq/ml of $H^3$ Thymidine is then added to these cultures and they are incubated for a further 8 hours at 37° C., 5% $CO_2$. The cells are harvested using a cell-harvester, and the level of thymidine incorporation into the cells is measured using a TopCount scintillation counter.

A reduction in thymidine incorporation into the previously peptide-pulsed PBMCs, compared to that seen in the non-pulsed PMBCs indicates that the transfected Regulatory T cells are causing a pMHC-specific down-regulation of cell proliferation.

An increase in thymidine incorporation into the previously peptide-pulsed PBMCs, compared to that seen in the non-pulsed PMBCs indicates that the transfected CTLs are causing a pMHC-specific up-regulation of cell proliferation.

Example 13 describes the treatment of patients with cells in accordance with the invention. This treatment method can be used for T cells transfected with any exogenous TCR.

Example 13

Infusion into Patients of T Cells Transfected to Express TCRs Including Cysteine Residues Required for the Formation of a Novel Inter-Chain Disulfide Bond In order to infuse the transfected T cells expressing TCRs including cysteine residues required for the formation of a novel inter-chain disulfide bond into patients the following methodology, as described in (Hague (2002) *Lancet* 360 436-442), is used. Briefly, the transfected T cells are washed in Hank's balanced buffer solution (Sigma, UK) with 10% autologous human serum albumin and then re-suspended in 20 ml of the same buffer solution. The transfected T cells are then slowly infused into the patient requiring treatment at a dose of $10^6$ cells per kg bodyweight over a 15 minute period. The patient's vital signs are regularly checked over the next 4 hours to detect any toxic effects.

These infusions are then repeated periodically, and the condition of the patient assessed by the most appropriate method. For example, in the case of a patient receiving the transfected TCRs as a means of treating a tumour these could include one or more of the following palpation, radiography, CT scanning or biopsy. The dosage and frequency of the infusions is varied if required. Finally the outcome of the treatment at 6 months after the final infusion is also recorded in accordance with WHO criteria.

The invention claimed is:

1. A method for obtaining modified mammalian cell, wherein the modified mammalian cell comprising a membrane presenting at least one modified T cell receptor (TCR) anchored to the membrane by a transmembrane sequence, the modified TCR comprising an interchain disulfide bond between extracellular constant domain residues which is not present in native TCRs, which method comprises incubating mammalian cell containing an expression vector encoding the modified TCR under conditions whereby the modified TCR is expressed, thereby obtaining the modified mammalian cell.

2. A method of directing immune cells to a population of target cells in a patient, said method comprising administering to the patient a plurality of immune cells comprising a membrane presenting at least one modified TCR anchored to the membrane by a transmembrane sequence, wherein the modified TCR comprises an interchain disulfide bond between extracellular constant domain residues which is not present in native TCRs wherein the modified TCR presented by such cells is specific for a TCR ligand presented on the target cells thereby directing the cells to the population of target cells in the patient.

3. A method of directing a T cell response to a target cell in a patient, said method comprising administering to the patient a plurality of T cells comprising a membrane presenting at least one modified TCR anchored to the membrane by a transmembrane sequence, wherein the modified TCR comprises an interchain disulfide bond between extracellular constant domain residues which is not present in native TCRs, wherein the modified TCR presented by such T cells is specific for a TCR ligand presented on the target cell, thereby directing the T cell response to the target cell in the patient.

4. The method according to claim 2 wherein the TCR ligand presented on the target cells is a peptide-MHC complex or a CD1-antigen complex.

5. The method according to claim 2 wherein the administered cells are not cytotoxic T cells.

6. The method according to claim 2 wherein the target cell is a cancer cell or infected cell and the administered cells are cytotoxic T cells.

7. The method according to claim 2 wherein the TCR ligand is unique to one tissue type or to cells characteristic of one organ of the body.

8. The method according to claim 7 wherein the target cell is a target for autoreactive T cells in autoimmune disease, organ rejection or graft versus host disease (GVHD).

9. The method according to claim 8 wherein the target cell is an islet cell.

10. A method for the preparation of cells comprising a membrane presenting a plurality of modified (TCRs) anchored to the membrane by a transmembrane sequence, wherein the modified TCRs comprise an interchain disulfide bond between extracellular constant domain residues which is not present in native TCRs, said method comprising: (a) isolation of a population of cells (b) in vitro transfection of said population of cells with an expression vector encoding the modified TCRs, said TCRs being specific for a target cell, and optionally (c) in vitro growth of the transfected cells.

11. The method according to claim 10 wherein the cells are T cells.

12. The method according to claim 10 wherein the population of cells is isolated from a patient who is to be treated by directing immune cells comprising a membrane presenting at least one modified TCR anchored to the membrane by a transmembrane sequence, wherein the modified TCR comprises an interchain disulfide bond between extracellular constant domain residues which is not present in native TCRs wherein the modified TCR presented by such cells is specific for a TCR ligand on the population of target cells to a population of target cells in the patient.

13. A method of treatment of cancer, GVHD, infection, organ rejection, or autoimmune disease comprising administering a plurality of immune cells comprising a membrane presenting at least one modified TCR anchored to the membrane by a transmembrane sequence, wherein the modified TCR comprises an interchain disulfide bond between extracellular constant domain residues which is not present in native TCRs.

14. The method according to claim 13 wherein the autoimmune disease is rheumatoid arthritis, diabetes, multiple sclerosis or reactive arthritis.

15. The method according to claim 3 wherein the TCR ligand on the target cell type is a peptide-MHC complex or a CD1-antigen complex.

16. The method according to claim 3 wherein the administered cells are not cytotoxic T cells.

17. The method according to claim 3 wherein the target cell is a cancer cell or infected cell and the administered cells are cytotoxic T cells.

18. The method according to claim 3 wherein the TCR ligand is unique to one tissue type or to cells characteristic of one organ of the body.

19. The method according to claim 18 wherein the target cell is a target for autoreactive T cells in autoimmune disease, organ rejection or (GVHD).

20. The method according to claim 19 wherein the target cell is an islet cell.

\* \* \* \* \*

UNITED STATES PATENT AND TRADEMARK OFFICE
CERTIFICATE OF CORRECTION

Page 1 of 1

PATENT NO. : 9,115,372 B2
APPLICATION NO. : 13/716817
DATED : August 25, 2015
INVENTOR(S) : Jakobsen It is certified that error appears in the above-identified patent and that said Letters Patent is hereby corrected as shown below:

On the title page insert item [30]

--(30) Foreign Application Priority Data

June 29, 2004 (GB)..................................0414499.4
October 1, 2004 (GB)..................................0421831.9
June 1, 2005 (GB)..................................0511123.2--

Signed and Sealed this
Nineteenth Day of January, 2016

Michelle K. Lee
*Director of the United States Patent and Trademark Office*

SEQUENCE LISTING

<160> NUMBER OF SEQ ID NOS: 149

<210> SEQ ID NO 1
<211> LENGTH: 30
<212> TYPE: PRT
<213> ORGANISM: Artificial Sequence

```
<220> FEATURE:
<223> OTHER INFORMATION: scTCR Linker

<400> SEQUENCE: 1

Pro Gly Gly Gly Ser Gly Gly Gly Ser Gly Gly Gly Ser Gly
1               5                   10                  15

Gly Gly Gly Ser Gly Gly Gly Ser Gly Gly Gly Pro
            20                  25                  30

<210> SEQ ID NO 2
<211> LENGTH: 20
<212> TYPE: PRT
<213> ORGANISM: Homo sapiens

<400> SEQUENCE: 2

Asp Ser Asp Val Tyr Ile Thr Asp Lys Thr Val Leu Asp Met Arg Ser
1               5                   10                  15

Met Asp Phe Lys
            20

<210> SEQ ID NO 3
<211> LENGTH: 20
<212> TYPE: PRT
<213> ORGANISM: Homo sapiens

<400> SEQUENCE: 3

Gln Ser Lys Asp Ser Asp Val Tyr Ile Thr Asp Lys Thr Val Leu Asp
1               5                   10                  15

Met Arg Ser Met
            20

<210> SEQ ID NO 4
<211> LENGTH: 20
<212> TYPE: PRT
<213> ORGANISM: Homo sapiens

<400> SEQUENCE: 4

Asp Ile Gln Asn Pro Asp Pro Ala Val Tyr Gln Leu Arg Asp Ser Lys
1               5                   10                  15

Ser Ser Asp Lys
            20

<210> SEQ ID NO 5
<211> LENGTH: 20
<212> TYPE: PRT
<213> ORGANISM: Homo sapiens

<400> SEQUENCE: 5

Asp Pro Ala Val Tyr Gln Leu Arg Asp Ser Lys Ser Ser Asp Lys Ser
1               5                   10                  15

Val Cys Leu Phe
            20

<210> SEQ ID NO 6
<211> LENGTH: 20
<212> TYPE: PRT
<213> ORGANISM: Homo sapiens

<400> SEQUENCE: 6

Asn Gly Lys Glu Val His Ser Gly Val Ser Thr Asp Pro Gln Pro Leu
1               5                   10                  15

Lys Glu Gln Pro
```

<210> SEQ ID NO 7
<211> LENGTH: 20
<212> TYPE: PRT
<213> ORGANISM: Homo sapiens

<400> SEQUENCE: 7

Ala Leu Asn Asp Ser Arg Tyr Ala Leu Ser Ser Arg Leu Arg Val Ser
1               5                   10                  15

Ala Thr Phe Trp
            20

<210> SEQ ID NO 8
<211> LENGTH: 20
<212> TYPE: PRT
<213> ORGANISM: Homo sapiens

<400> SEQUENCE: 8

Pro Pro Glu Val Ala Val Phe Glu Pro Ser Glu Ala Glu Ile Ser His
1               5                   10                  15

Thr Gln Lys Ala
            20

<210> SEQ ID NO 9
<211> LENGTH: 20
<212> TYPE: PRT
<213> ORGANISM: Homo sapiens

<400> SEQUENCE: 9

Lys Glu Val His Ser Gly Val Ser Thr Asp Pro Gln Pro Leu Lys Glu
1               5                   10                  15

Gln Pro Ala Leu
            20

<210> SEQ ID NO 10
<211> LENGTH: 20
<212> TYPE: PRT
<213> ORGANISM: Homo sapiens

<400> SEQUENCE: 10

Val Phe Pro Pro Glu Val Ala Val Phe Glu Pro Ser Glu Ala Glu Ile
1               5                   10                  15

Ser His Thr Gln
            20

<210> SEQ ID NO 11
<211> LENGTH: 91
<212> TYPE: PRT
<213> ORGANISM: Mus musculus

<400> SEQUENCE: 11

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
                20                  25                  30

Ile Asn Val Pro Lys Thr Met Glu Ser Gly Thr Phe Ile Thr Asp Lys
            35                  40                  45

Thr Val Leu Asp Met Lys Ala Met Asp Ser Lys Ser Asn Gly Ala Ile
        50                  55                  60

Ala Trp Ser Asn Gln Thr Ser Phe Thr Cys Gln Asp Ile Phe Lys Glu

```
65                  70                  75                  80
Thr Asn Ala Thr Tyr Pro Ser Ser Asp Val Pro
                85                  90

<210> SEQ ID NO 12
<211> LENGTH: 126
<212> TYPE: PRT
<213> ORGANISM: Mus musculus

<400> SEQUENCE: 12

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Arg Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp
        115                 120                 125

<210> SEQ ID NO 13
<211> LENGTH: 20
<212> TYPE: PRT
<213> ORGANISM: Mus musculus

<400> SEQUENCE: 13

Glu Ser Gly Thr Phe Ile Thr Asp Lys Thr Val Leu Asp Met Lys Ala
1               5                   10                  15

Met Asp Ser Lys
            20

<210> SEQ ID NO 14
<211> LENGTH: 20
<212> TYPE: PRT
<213> ORGANISM: Mus musculus

<400> SEQUENCE: 14

Lys Thr Met Glu Ser Gly Thr Phe Ile Thr Asp Lys Thr Val Leu Asp
1               5                   10                  15

Met Lys Ala Met
            20

<210> SEQ ID NO 15
<211> LENGTH: 20
<212> TYPE: PRT
<213> ORGANISM: Mus musculus

<400> SEQUENCE: 15

Tyr Ile Gln Asn Pro Glu Pro Ala Val Tyr Gln Leu Lys Asp Pro Arg
1               5                   10                  15

Ser Gln Asp Ser
            20
```

<210> SEQ ID NO 16
<211> LENGTH: 20
<212> TYPE: PRT
<213> ORGANISM: Mus musculus

<400> SEQUENCE: 16

Ala Val Tyr Gln Leu Lys Asp Pro Arg Ser Gln Asp Ser Thr Leu Cys
1               5                   10                  15

Leu Phe Thr Asp
            20

<210> SEQ ID NO 17
<211> LENGTH: 20
<212> TYPE: PRT
<213> ORGANISM: Mus musculus

<400> SEQUENCE: 17

Asn Gly Arg Glu Val His Ser Gly Val Ser Thr Asp Pro Gln Ala Tyr
1               5                   10                  15

Lys Glu Ser Asn
            20

<210> SEQ ID NO 18
<211> LENGTH: 20
<212> TYPE: PRT
<213> ORGANISM: Mus musculus

<400> SEQUENCE: 18

Lys Glu Ser Asn Tyr Ser Tyr Cys Leu Ser Arg Leu Arg Val Ser
1               5                   10                  15

Ala Thr Phe Trp
            20

<210> SEQ ID NO 19
<211> LENGTH: 20
<212> TYPE: PRT
<213> ORGANISM: Mus musculus

<400> SEQUENCE: 19

Pro Pro Lys Val Ser Leu Phe Glu Pro Ser Lys Ala Glu Ile Ala Asn
1               5                   10                  15

Lys Gln Lys Ala
            20

<210> SEQ ID NO 20
<211> LENGTH: 20
<212> TYPE: PRT
<213> ORGANISM: Mus musculus

<400> SEQUENCE: 20

Arg Glu Val His Ser Gly Val Ser Thr Asp Pro Gln Ala Tyr Lys Glu
1               5                   10                  15

Ser Asn Tyr Ser
            20

<210> SEQ ID NO 21
<211> LENGTH: 20
<212> TYPE: PRT
<213> ORGANISM: Mus musculus

<400> SEQUENCE: 21

Val Thr Pro Pro Lys Val Ser Leu Phe Glu Pro Ser Lys Ala Glu Ile

```
1               5                  10                 15
Ala Asn Lys Gln
            20

<210> SEQ ID NO 22
<211> LENGTH: 9
<212> TYPE: PRT
<213> ORGANISM: Mus musculus

<400> SEQUENCE: 22

Ala Ser Asn Glu Asn Met Asp Ala Met
1               5

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
cacagacaaa tgtgtgctag acat                                             24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
atgtctagca cacatttgtc tgtg                                             24

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cagtggggtc tgcacagacc c                                                21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
gggtctgtgc agaccccact g                                                21

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
atgatgaaat ccttgagagt ttt                                              23

<210> SEQ ID NO 28
<211> LENGTH: 20
```

```
<212> TYPE: DNA
<213> ORGANISM: Artificial Sequence
<220> FEATURE:
<223> OTHER INFORMATION: Primer

<400> SEQUENCE: 28
gtaagtgcag ttgagagagg                                                    20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
atgagcatcg gcctcctgt                                                     19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ttcatatcct gggcacactg                                                    20

<210> SEQ ID NO 31
<211> LENGTH: 46
<212> TYPE: DNA
<213> ORGANISM: Artificial Sequence
<220> FEATURE:
<223> OTHER INFORMATION: Primer

<400> SEQUENCE: 31
tccccagccc agaaagttcc tctgatgtca agctggtcga gaaaag                       46

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ttagctggac cacagccgca g                                                  21

<210> SEQ ID NO 33
<211> LENGTH: 48
<212> TYPE: DNA
<213> ORGANISM: Artificial Sequence
<220> FEATURE:
<223> OTHER INFORMATION: Primer

<400> SEQUENCE: 33
ccgaggcctg gggtagagca gactctggct tcacctccga gtcttacc                     48

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
```

```
ttagcctctg gaatcctttc tc                                             22
```

<210> SEQ ID NO 35
<211> LENGTH: 621
<212> TYPE: DNA
<213> ORGANISM: Artificial Sequence
<220> FEATURE:
<223> OTHER INFORMATION: DNA encoding the alpha chain of a soluble
      disulfide-linked A6 TCR

<400> SEQUENCE: 35

```
atgcagaagg aagtggagca gaactctgga cccctcagtg ttccagaggg agccattgcc    60
tctctcaact gcacttacag tgaccgaggt tcccagtcct tcttctggta cagacaatat   120
tctgggaaaa gccctgagtt gataatgtcc atatactcca atggtgacaa agaagatgga   180
aggtttacag cacagctcaa taaagccagc cagtatgttt ctctgctcat cagagactcc   240
cagcccagtg attcagccac ctacctctgt gccgttacaa ctgacagctg ggggaaattg   300
cagtttggag cagggaccca ggttgtggtc accccagata tccagaaccc tgaccctgcc   360
gtgtaccagc tgagagactc taaatccagt gacaagtctg tctgcctatt caccgatttt   420
gattctcaaa caaatgtgtc acaaagtaag gattctgatg tgtatatcac agacaaatgt   480
gtgctagaca tgaggtctat ggacttcaag agcaacagtg ctgtggcctg agcaacaaa   540 tctgactttg catgtgcaaa cgccttcaac aacagcatta ttccagaaga caccttcttc   600
cccagcccag aaagttccta a                                             621
```

<210> SEQ ID NO 36
<211> LENGTH: 741
<212> TYPE: DNA
<213> ORGANISM: Artificial Sequence
<220> FEATURE:
<223> OTHER INFORMATION: DNA encoding the beta chain of a soluble
      disulfide-linked A6 TCR

<400> SEQUENCE: 36

```
atgaacgctg gtgtcactca gaccccaaaa ttccaggtcc tgaagacagg acagagcatg    60
acactgcagt gtgcccagga tatgaaccat gaatacatgt cctggtatcg acaagaccca   120 ggcatgggc tgaggctgat tcattactca gttggtgctg gtatcactga ccaaggagaa   180
gtccccaatg gctacaatgt ctccagatca accacagagg atttcccgct caggctgctg   240
tcggctgctc cctcccagac atctgtgtac ttctgtgcca gcaggccggg actagcggga   300
gggcgaccag agcagtactt cgggccgggc accaggctca cggtcacaga ggacctgaaa   360
aacgtgttcc cacccgaggt cgctgtgttt gagccatcag aagcagagat ctcccacacc   420
caaaaggcca cactggtgtg cctggccaca ggcttctacc ccgaccacgt ggagctgagc   480
tggtgggtga atgggaagga ggtgcacagt ggggtctgca cagacccgca gccctcaag   540 gagcagcccg ccctcaatga ctccagatac gctctgagca gccgcctgag ggtctcggcc   600
accttctggc aggacccccg caaccacttc cgctgtcaag tccagttcta cgggctctcg   660
gagaatgacg agtggaccca ggatagggcc aaacccgtca cccagatcgt cagcgccgag   720 gcctgggta gagcagacta a                                             741
```

<210> SEQ ID NO 37
<211> LENGTH: 206
<212> TYPE: PRT
<213> ORGANISM: Artificial Sequence
<220> FEATURE:
<223> OTHER INFORMATION: Alpha chain of a soluble disulfide-linked A6

TCR

<400> SEQUENCE: 37

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Pro
            100                 105                 110

Asp Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 38
<211> LENGTH: 246
<212> TYPE: PRT
<213> ORGANISM: Artificial Sequence
<220> FEATURE:
<223> OTHER INFORMATION: Beta chain of a soluble disulfide-linked A6
      TCR

<400> SEQUENCE: 38

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr

-continued

```
                130                 135                 140
Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
            195                 200                 205

His Phe Arg Cys Gln Val Gln Phe Tyr Gly Leu Ser Glu Asn Asp Glu
        210                 215                 220

Trp Thr Gln Asp Arg Ala Lys Pro Val Thr Gln Ile Val Ser Ala Glu
225                 230                 235                 240

Ala Trp Gly Arg Ala Asp
                245
```

<210> SEQ ID NO 39
<211> LENGTH: 274
<212> TYPE: PRT
<213> ORGANISM: Artificial Sequence
<220> FEATURE:
<223> OTHER INFORMATION: Membrane-anchored A6 TCR alpha chain with
      introduced disulfide in terchain bond

<400> SEQUENCE: 39

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
                20                  25                  30

Leu Ser Val Pro Glu Gly Ala Ile Ala Ser Leu Asn Cys Thr Tyr Ser
            35                  40                  45

Asp Arg Gly Ser Gln Ser Phe Phe Trp Tyr Arg Gln Tyr Ser Gly Lys
        50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Thr Thr Asp Ser Trp Gly Lys Leu Gln Phe Gly Ala Gly Thr Gln
        115                 120                 125

Val Val Val Thr Pro Asp Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Ser Asp Val Lys Leu Val Glu Lys Ser Phe Glu Thr Asp
225                 230                 235                 240
```

Thr Asn Leu Asn Phe Gln Asn Leu Ser Val Ile Gly Phe Arg Ile Leu
            245                 250                 255

Leu Leu Lys Val Ala Gly Phe Asn Leu Leu Met Thr Leu Arg Leu Trp
        260                 265                 270

Ser Ser

<210> SEQ ID NO 40
<211> LENGTH: 825
<212> TYPE: DNA
<213> ORGANISM: Artificial Sequence
<220> FEATURE:
<223> OTHER INFORMATION: DNA encoding membrane-anchored A6 TCR alpha
      chain with introduced disulfide interchain bond

<400> SEQUENCE: 40

```
atgatgaaat ccttgagagt tttactagtg atcctgtggc ttcagttgag ctgggtttgg      60
agccaacaga aggaagtgga gcagaactct ggacccctca gtgttccaga gggagccatt     120
gcctctctca actgcactta cagtgaccga ggttcccagt ccttcttctg gtacagacaa     180
tattctggga aaagccctga gttgataatg tccatatact ccaatggtga caaagaagat     240
ggaaggttta cagcacagct caataaagcc agccagtatg tttctctgct catcagagac     300
tcccagccca gtgattcagc cacctacctc tgtgccgtta caactgacag ctgggggaaa     360
ttgcagtttg gagcagggac ccaggttgtg gtcaccccag atatccagaa ccctgaccct     420
gccgtgtacc agctgagaga ctctaaatcc agtgacaagt ctgtctgcct attcaccgat     480
tttgattctc aaacaaatgt gtcacaaagt aaggattctg atgtgtatat cacagacaaa     540
tgtgtgctag acatgaggtc tatggacttc aagagcaaca gtgctgtggc ctggagcaac     600
aaatctgact ttgcatgtgc aaacgccttc aacaacagca ttattccaga agacaccttc     660
ttccccagcc cagaaagttc ctctgatgtc aagctggtcg agaaaagctt tgaaacagat     720
acgaacctaa actttcaaaa cctgtcagtg attgggttcc gaatcctcct cctgaaagtg     780
gccgggttta atctgctcat gacgctgcgg ctgtggtcca gctaa                     825
```

<210> SEQ ID NO 41
<211> LENGTH: 313
<212> TYPE: PRT
<213> ORGANISM: Artificial Sequence
<220> FEATURE:
<223> OTHER INFORMATION: Membrane-anchored A6 TCR beta chain with
      introduced disulfide interchain bond

<400> SEQUENCE: 41

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

```
Arg Pro Gly Leu Ala Gly Gly Arg Pro Glu Gln Tyr Phe Gly Pro Gly
            115                 120                 125
Thr Arg Leu Thr Val Thr Glu Asp Leu Lys Asn Val Phe Pro Pro Glu
        130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Tyr Pro Asp His Val Glu
                165                 170                 175
Leu Ser Trp Trp Val Asn Gly Lys Glu Val His Ser Gly Val Cys Thr
            180                 185                 190
Asp Pro Gln Pro Leu Lys Glu Gln Pro Ala Leu Asn Asp Ser Arg Tyr
        195                 200                 205
Cys Leu Ser Ser Arg Leu Arg Val Ser Ala Thr Phe Trp Gln Asp Pro
    210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Ser Gly Phe Thr Ser Glu Ser Tyr
            260                 265                 270
Gln Gln Gly Val Leu Ser Ala Thr Ile Leu Tyr Glu Ile Leu Leu Gly
        275                 280                 285
Lys Ala Thr Leu Tyr Ala Val Leu Val Ser Ala Leu Val Leu Met Ala
    290                 295                 300
Met Val Lys Arg Lys Asp Ser Arg Gly
305                 310

<210> SEQ ID NO 42
<211> LENGTH: 942
<212> TYPE: DNA
<213> ORGANISM: Artificial Sequence
<220> FEATURE:
<223> OTHER INFORMATION: DNA encoding membrane-anchored A6 TCR beta
      chain with introduced disulfide interchain bond

<400> SEQUENCE: 42
atgagcatcg gcctcctgtg ctgtgcagcc ttgtctctcc tgtgggcagg tccagtgaac      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcaggc cgggactagc gggagggcga     360
ccagagcagt acttcgggcc gggcaccagg ctcacggtca cagaggacct gaaaaacgtg     420
ttcccacccg aggtcgctgt gtttgagcca tcagaagcag agatctccca cacccaaaag     480
gccacactgg tgtgcctggc cacaggcttc taccccgacc acgtggagct gagctggtgg     540
gtgaatggga aggaggtgca cagtggggtc tgcacagacc cgcagcccct caaggagcag     600
cccgccctca tgactccaga atactgcctg agcagccgcc tgagggtctc ggccaccttc     660
tggcaggacc ccgcaaccca cttccgctgt caagtccagt tctacgggct ctcggagaat     720
gacgagtgga cccaggatag ggccaaaccc gtcacccaga tcgtcagcgc cgaggcctgg     780
ggtagagcag actctggctt cacctccgag tcttaccagc aaggggtcct gtctgccacc     840
atcctctatg agatcttgct agggaaggcc accttgtatg ccgtgctggt cagtgccctc     900
```

```
gtgctgatgg ccatggtaaa gagaaaggat tccagaggct aa              942
```

<210> SEQ ID NO 43
<211> LENGTH: 425
<212> TYPE: DNA
<213> ORGANISM: Homo sapiens

<400> SEQUENCE: 43

```
atatccagaa ccctgaccct gccgtgtacc agctgagaga ctctaaatcc agtgacaagt    60
ctgtctgcct attcaccgat tttgattctc aaacaaatgt gtcacaaagt aaggattctg   120
atgtgtatat cacagacaaa actgtgctag acatgaggtc tatggacttc aagagcaaca   180
gtgctgtggc ctggagcaac aaatctgact tgcatgtgc aaacgccttc aacaacagca   240
ttattccaga agacaccttc ttccccagcc cagaaagttc ctgtgatgtc aagctggtcg   300
agaaaagctt tgaaacagat acgaacctaa actttcaaaa cctgtcagtg attgggttcc   360
gaatcctcct cctgaaagtg gccgggttta atctgctcat acgctgcgg ctgtggtcca   420
gctga                                                              425
```

<210> SEQ ID NO 44
<211> LENGTH: 326
<212> TYPE: DNA
<213> ORGANISM: Homo sapiens

<400> SEQUENCE: 44

```
atgtggggag cttccttct ctatgtttcc atgaagatgg gaggcactgc aggacaaagc    60
cttgagcagc cctctgaagt gacagctgtg gaaggagcca ttgtccagat aaactgcacg   120
taccagacat ctgggttta tgggctgtcc tggtaccagc aacatgatgg cggagcaccc   180
acatttcttt cttacaatgc tctggatggt ttggaggaga caggtcgttt tcttcattc   240
cttagtcgct ctgatagtta tggttacctc cttctacagg agctccagat gaaagactct   300
gcctcttact tctgcgctgt gagaga                                        326
```

<210> SEQ ID NO 45
<211> LENGTH: 326
<212> TYPE: DNA
<213> ORGANISM: Homo sapiens

<400> SEQUENCE: 45

```
atgtggggag ttttccttct ttatgtttcc atgaagatgg gaggcactac aggacaaaac    60
attgaccagc ccactgagat gacagctacg gaaggtgcca ttgtccagat caactgcacg   120
taccagacat ctgggttcaa cgggctgttc tggtaccagc aacatgctgg cgaagcaccc   180
acatttctgt cttacaatgt tctggatggt ttggaggaga aggtcgttt tcttcattc    240
cttagtcggt ctaaagggta cagttacctc cttttgaagg agctccagat gaaagactct   300
gcctcttacc tctgtgctgt gagaga                                        326
```

<210> SEQ ID NO 46
<211> LENGTH: 338
<212> TYPE: DNA
<213> ORGANISM: Homo sapiens

<400> SEQUENCE: 46

```
atggctttgc agagcactct ggggcggtg tggctagggc ttctcctcaa ctctctctgg    60
aaggttgcag aaagcaagga ccaagtgttt cagccttcca cagtggcatc ttcagaggga   120
```

```
gctgtggtgg aaatcttctg taatcactct gtgtccaatg cttacaactt cttctggtac      180
cttcacttcc cgggatgtgc accaagactc cttgttaaag gctcaaagcc ttctcagcag      240
ggacgataca acatgaccta tgaacggttc tcttcatcgc tgctcatcct ccaggtgcgg      300
gaggcagatg ctgctgttta ctactgtgct gtggagga                             338

<210> SEQ ID NO 47
<211> LENGTH: 343
<212> TYPE: DNA
<213> ORGANISM: Homo sapiens

<400> SEQUENCE: 47
atggcctctg cacccatctc gatgcttgcg atgctcttca cattgagtgg gctgagagct      60
cagtcagtgg ctcagccgga agatcaggtc aacgttgctg aagggaatcc tctgactgtg     120
aaatgcacct attcagtctc tggaaaccct tatcttttttt ggtatgttca ataccccaac    180
cgaggcctcc agttccttct gaaatacatc acagggata acctggttaa aggcagctat      240
ggctttgaag ctgaatttaa caagagccaa acctccttcc acctgaagaa accatctgcc     300
cttgtgagcg actccgcttt gtacttctgt gctgtgagag aca                       343

<210> SEQ ID NO 48
<211> LENGTH: 328
<212> TYPE: DNA
<213> ORGANISM: Homo sapiens

<400> SEQUENCE: 48
atgaggcaag tggcgagagt gatcgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga    180
ccacgattta ttattcaagg atacaagaca aaagttacaa cgaagtggc ctccctgttt      240 atccctgccg acagaaagtc cagcactctg agcctgcccc gggtttccct gagcgacact     300
gctgtgtact actgcctcgt gggtgaca                                        328

<210> SEQ ID NO 49
<211> LENGTH: 340
<212> TYPE: DNA
<213> ORGANISM: Homo sapiens

<400> SEQUENCE: 49
atgaagacat tgctggatt ttcgttcctg tttttgtggc tgcagctgga ctgtatgagt       60
agaggagagg atgtggagca gagtctttc ctgagtgtcc gagagggaga cagctccgtt      120
ataaactgca cttacacaga cagctcctcc acctacttat actggtataa gcaagaacct    180
ggagcaggtc tccagttgct gacgtatatt ttttcaaata tggacatgaa acaagaccaa    240
agactcactg ttctattgaa taaaaaggat aaacatctgt ctctgcgcat tgcagacacc    300
cagactgggg actcagctat ctacttctgt gcagagagta                           340

<210> SEQ ID NO 50
<211> LENGTH: 340
<212> TYPE: DNA
<213> ORGANISM: Homo sapiens

<400> SEQUENCE: 50
atggagtcat tcctgggagg tgttttgctg attttgtggc ttcaagtgga ctgggtgaag      60
agccaaaaga tagaacagaa ttccgaggcc ctgaacattc aggagggtaa aacggccacc     120
```

| | | |
|---|---|---|
| ctgacctgca actatacaaa ctattcccca gcatacttac agtggtaccg acaagatcca | 180 | |
| ggaagaggcc ctgttttctt gctactcata cgtgaaaatg agaaagaaaa aaggaaagaa | 240 | |
| agactgaagg tcacctttga taccacccct aaacagagtt tgtttcatat cacagcctcc | 300 | |
| cagcctgcag actcagctac ctacctctgt gctctagaca | 340 | |

<210> SEQ ID NO 51
<211> LENGTH: 337
<212> TYPE: DNA
<213> ORGANISM: Homo sapiens

<400> SEQUENCE: 51

| | | |
|---|---|---|
| atggagaaga tgcggagacc tgtcctaatt atattttgtc tatgtcttgg ctgggcaaat | 60 | |
| ggagaaaacc aggtggagca cagccctcat tttctgggac cccagcaggg agacgttgcc | 120 | |
| tccatgagct gcacgtactc tgtcagtcgt tttaacaatt tgcagtggta caggcaaaat | 180 | |
| acagggatgg gtcccaaaca cctattatcc atgtattcag ctggatatga aagcagaaa | 240 | |
| ggaagactaa atgctacatt actgaagaat ggaagcagct tgtacattac agccgtgcag | 300 | |
| cctgaagatt cagccaccta tttctgtgct gtagatg | 337 | |

<210> SEQ ID NO 52
<211> LENGTH: 341
<212> TYPE: DNA
<213> ORGANISM: Homo sapiens

<400> SEQUENCE: 52

| | | |
|---|---|---|
| atgctcctgt tgctcatacc agtgctgggg atgattttg ccctgagaga tgccagagcc | 60 | |
| cagtctgtga ccagcataa ccaccacgta attctctctg aagcagcctc actggagttg | 120 | |
| ggatgcaact attcctatgg tggaactgtt aatctcttct ggtatgtcca gtaccctggt | 180 | |
| caacaccttc agcttctcct caagtacttt tcaggggatc cactggttaa aggcatcaag | 240 | |
| ggctttgagg ctgaatttat aaagagtaaa ttctccttta atctgaggaa accctctgtg | 300 | |
| cagtggagtg acacagctga gtacttctgt gccgtgaatg c | 341 | |

<210> SEQ ID NO 53
<211> LENGTH: 341
<212> TYPE: DNA
<213> ORGANISM: Homo sapiens

<400> SEQUENCE: 53

| | | |
|---|---|---|
| atgctcctgc tgctcgtccc agtgctcgag gtgattttta ctctgggagg aaccagagcc | 60 | |
| cagtcggtga cccagcttga cagccacgtc tctgtctctg aaggaacccc ggtgctgctg | 120 | |
| aggtgcaact actcatcttc ttattcacca tctctcttct ggtatgtgca acaccccaac | 180 | |
| aaaggactcc agcttctcct gaagtacaca tcagcggcca ccctggttaa aggcatcaac | 240 | |
| ggttttgagg ctgaatttaa gaagagtgaa acctccttcc acctgacgaa accctcagcc | 300 | |
| catatgagcg acgcggctga gtacttctgt gttgtgagtg a | 341 | |

<210> SEQ ID NO 54
<211> LENGTH: 341
<212> TYPE: DNA
<213> ORGANISM: Homo sapiens

<400> SEQUENCE: 54

| | | |
|---|---|---|
| atgctcctgg agcttatccc actgctgggg atacattttg tcctgagaac tgccagagcc | 60 | |

```
cagtcagtga cccagcctga catccacatc actgtctctg aaggagcctc actggagttg    120
agatgtaact attcctatgg ggcaacacct tatctcttct ggtatgtcca gtcccccggc    180
caaggcctcc agctgctcct gaagtacttt tcaggagaca ctctggttca aggcattaaa    240
ggctttgagg ctgaatttaa gaggagtcaa tcttccttca atctgaggaa accctctgtg    300
cattggagtg atgctgctga gtacttctgt gctgtgggtg c                        341

<210> SEQ ID NO 55
<211> LENGTH: 341
<212> TYPE: DNA
<213> ORGANISM: Homo sapiens

<400> SEQUENCE: 55
atgctcctgc tgctcgtccc agtgctcgag gtgattttta ccctgggagg aaccagagcc    60
cagtcggtga cccagcttgg cagccacgtc tctgtctctg aaggagccct ggttctgctg    120
aggtgcaact actcatcgtc tgttccacca tatctcttct ggtatgtgca ataccccaac    180
caaggactcc agcttctcct gaagtacaca tcagcggcca ccctggttaa aggcatcaac    240
ggttttgagg ctgaatttaa gaagagtgaa acctccttcc acctgacgaa accctcagcc    300
catatgagcg acgcggctga gtacttctgt gctgtgagtg a                        341

<210> SEQ ID NO 56
<211> LENGTH: 341
<212> TYPE: DNA
<213> ORGANISM: Homo sapiens

<400> SEQUENCE: 56
atgctcctgc tgctcgtccc agcgttccag gtgattttta ccctgggagg aaccagagcc    60
cagtctgtga cccagcttga cagccaagtc cctgtctttg aagaagcccc tgtggagctg    120
aggtgcaact actcatcgtc tgtttcagtg tatctcttct ggtatgtgca ataccccaac    180
caaggactcc agcttctcct gaagtattta tcaggatcca ccctggttaa aggcatcaac    240
ggttttgagg ctgaatttaa caagagtcaa acttccttcc acttgaggaa accctcagtc    300
catataagcg acacggctga gtacttctgt gctgtgagtg a                        341

<210> SEQ ID NO 57
<211> LENGTH: 347
<212> TYPE: DNA
<213> ORGANISM: Homo sapiens

<400> SEQUENCE: 57
atgctcttag tggtcattct gctgcttgga atgttcttca cactgagagg aaccagaacc    60
cagtcggtga cccagcttga tggccacatc actgtctctg aagaagcccc tctggaactg    120
aagtgcaact attcctatag tggagttcct tctctcttct ggtatgtcca atactctagc    180
caaagcctcc agcttctcct caaagaccta acagaggcca cccaggttaa aggcatcaga    240
ggttttgagg ctgaatttaa gaagagcgaa acctccttct acctgaggaa accatcaacc    300
catgtgagtg atgctgctga gtacttctgt gctgtgggtg acaggag                  347

<210> SEQ ID NO 58
<211> LENGTH: 338
<212> TYPE: DNA
<213> ORGANISM: Homo sapiens

<400> SEQUENCE: 58
atgaattctt ctccaggacc agcgattgca ctattcttaa tgtttgggg aatcaatgga    60
```

```
gattcagtgg tccagacaga aggccaagtg ctcccctctg aagggattc  cctgattgtg    120 aactgctcct atgaaaccac acagtaccct tccctttttt ggtatgtcca atatcctgga    180
gaaggtccac agctccacct gaaagccatg aaggccaatg acaagggaag gaacaaaggt    240
tttgaagcca tgtaccgtaa agaaaccact tctttccact tggagaaaga ctcagttcaa    300
gagtcagact ccgctgtgta cttctgtgct ctgagtga                            338

<210> SEQ ID NO 59
<211> LENGTH: 338
<212> TYPE: DNA
<213> ORGANISM: Homo sapiens

<400> SEQUENCE: 59
atgaactatt ctccaggctt agtatctctg atactcttac tgcttggaag aacccgtgga     60
aattcagtga cccagatgga agggccagtg actctctcag aagaggcctt cctgactata    120
aactgcacgt acacagccac aggataccct tcccttttct ggtatgtcca atatcctgga    180
gaaggtctac agctcctcct gaaagccacg aaggctgatg acaagggaag caacaaaggt    240
tttgaagcca cataccgtaa agaaaccact tctttccact tggagaaagg ctcagttcaa    300
gtgtcagact cagcggtgta cttctgtgct ctgagtga                            338

<210> SEQ ID NO 60
<211> LENGTH: 343
<212> TYPE: DNA
<213> ORGANISM: Homo sapiens

<400> SEQUENCE: 60
atgaaaaagc atctgacgac cttcttggtg attttgtggc tttatttta  tagggggaat     60 ggcaaaaacc aagtggagca gagtcctcag tccctgatca tcctggaggg aaagaactgc    120
actcttcaat gcaattatac agtgagcccc ttcagcaact taaggtggta taagcaagat    180
actgggagag gtcctgtttc cctgacaatc atgactttca gtgagaacac aaagtcgaac    240
ggaagatata cagcaactct ggatgcagac acaaagcaaa gctctctgca catcacagcc    300
tcccagctca gcgattcagc ctcctacatc tgtgtggtga gcg                      343

<210> SEQ ID NO 61
<211> LENGTH: 337
<212> TYPE: DNA
<213> ORGANISM: Homo sapiens

<400> SEQUENCE: 61
atgatatcct tgagagtttt actggtgatc ctgtggcttc agttaagctg ggtttggagc     60
caacggaagg aggtggagca ggatcctgga cccttcaatg ttccagaggg agccactgtc    120
gctttcaact gtacttacag caacagtgct tctcagtctt tcttctggta cagacaggat    180
tgcaggaaag aacctaagtt gctgatgtcc gtatactcca gtggtaatga agatggaagg    240
tttacagcac agctcaatag agccagccag tatatttccc tgctcatcag agactccaag    300
ctcagtgatt cagccaccta cctctgtgtg gtgaaca                             337

<210> SEQ ID NO 62
<211> LENGTH: 343
<212> TYPE: DNA
<213> ORGANISM: Homo sapiens

<400> SEQUENCE: 62
```

```
atgatgaaat ccttgagagt tttactagtg atcctgtggc ttcagttgag ctgggtttgg      60
agccaacaga aggaggtgga gcagaattct ggacccctca gtgttccaga gggagccatt     120
gcctctctca actgcactta cagtgaccga ggttcccagt ccttcttctg gtacagacaa     180
tattctggga aaagccctga gttgataatg ttcatatact ccaatggtga caaagaagat     240
ggaaggttta cagcacagct caataaagcc agccagtatg tttctctgct catcagagac     300
tcccagccca gtgattcagc cacctacctc tgtgccgtga aca                       343
```

```
<210> SEQ ID NO 63
<211> LENGTH: 343
<212> TYPE: DNA
<213> ORGANISM: Homo sapiens

<400> SEQUENCE: 63
atgatgaaat ccttgagagt tttactggtg atcctgtggc ttcagttaag ctgggtttgg      60
agccaacaga aggaggtgga gcaggatcct ggaccactca gtgttccaga gggagccatt     120
gtttctctca actgcactta cagcaacagt gcttttcaat acttcatgtg gtacagacag     180
tattccagaa aagccctga gttgctgatg tacacatact ccagtggtaa caaagaagat     240
ggaaggttta cagcacaggt cgataaatcc agcaagtata tctccttgtt catcagagac     300
tcacagccca gtgattcagc cacctacctc tgtgcaatga gcg                       343
```

```
<210> SEQ ID NO 64
<211> LENGTH: 337
<212> TYPE: DNA
<213> ORGANISM: Homo sapiens

<400> SEQUENCE: 64
atgacatcca ttcgagctgt atttatattc ctgtggctgc agctggactt ggtgaatgga      60
gagaatgtgg agcagcatcc ttcaaccctg agtgtccagg agggagacag cgctgttatc     120
aagtgtactt attcagacag tgcctcaaac tacttccctt ggtataagca agaacttgga     180
aaaggacctc agcttattat agacattcgt tcaaatgtgg gcgaaaagaa agaccaacga     240
attgctgtta cattgaacaa gacagccaaa catttctccc tgcacatcac agagacccaa     300
cctgaagact cggctgtcta cttctgtgca gcaagta                              337
```

```
<210> SEQ ID NO 65
<211> LENGTH: 340
<212> TYPE: DNA
<213> ORGANISM: Homo sapiens

<400> SEQUENCE: 65
atggcaggca ttcgagcttt atttatgtac ttgtggctgc agctggactg ggtgagcaga      60
ggagagagtg tggggctgca tcttcctacc ctgagtgtcc aggagggtga caactctatt     120
atcaactgtg cttattcaaa cagcgcctca gactacttca tttggtacaa gcaagaatct     180
ggaaaaggtc ctcaattcat tatagacatt cgttcaaata tggacaaaag gcaaggccaa     240
agagtcaccg tttattgaa taagacagtg aaacatctct ctctgcaaat tgcagctact     300
caacctggag actcagctgt ctactttgt gcagagaata                           340
```

```
<210> SEQ ID NO 66
<211> LENGTH: 350
<212> TYPE: DNA
<213> ORGANISM: Homo sapiens

<400> SEQUENCE: 66
```

```
atgtcacttt ctagcctgct gaaggtggtc acagcttcac tgtggctagg acctggcatt    60
gcccagaaga taactcaaac ccaaccagga atgttcgtgc aggaaaagga ggctgtgact   120
ctggactgca catatgacac cagtgatcaa agttatggtc tattctggta caagcagccc   180
agcagtgggg aaatgatttt tcttatttat caggggtctt atgacgagca aaatgcaaca   240
gaaggtcgct actcattgaa tttccagaag gcaagaaaat ccgccaacct tgtcatctcc   300
gcttcacaac tgggggactc agcaatgtat ttctgtgcaa tgagagaggg              350
```

<210> SEQ ID NO 67
<211> LENGTH: 329
<212> TYPE: DNA
<213> ORGANISM: Homo sapiens

<400> SEQUENCE: 67

```
atgaagccca ccctcatctc agtgcttgtg ataatattta tactcagagg aacaagagcc    60
cagagagtga ctcagcccga gaagctcctc tctgtcttta aggggcccc agtggagctg    120 aagtgcaact attcctattc tgggagtcct gaactcttct ggtatgtcca gtactccaga   180
caacgcctcc agttactctt gagacacatc tctagagaga gcatcaaagg cttcactgct   240
gaccttaaca aaggcgagac atctttccac ctgaagaaac catttgctca gaggaagac   300 tcagccatgt attactgtgc tctaagtgg                                     329
```

<210> SEQ ID NO 68
<211> LENGTH: 337
<212> TYPE: DNA
<213> ORGANISM: Homo sapiens

<400> SEQUENCE: 68

```
atggaaactc tcctgggagt gtctttggtg attctatggc ttcaactggc tagggtgaac    60
agtcaacagg agaagagga tcctcaggcc ttgagcatcc aggagggtga aaatgccacc   120
atgaactgca gttacaaaac tagtataaac aatttacagt ggtatagaca aaattcaggt   180
agaggccttg tccacctaat tttaatacgt tcaaatgaaa gagagaaaca cagtggaaga   240
ttaagagtca cgcttgacac ttccaagaaa agcagttcct tgttgatcac ggcttcccgg   300
gcagcagaca ctgcttctta cttctgtgct acggacg                            337
```

<210> SEQ ID NO 69
<211> LENGTH: 335
<212> TYPE: DNA
<213> ORGANISM: Homo sapiens

<400> SEQUENCE: 69

```
atgctgtctg cttcctgctc aggacttgtg atcttgttga tattcagaag gaccagtgga    60
gactcggtta cccagacaga aggcccagtt accctccctg agagggcagc tctgacatta   120
aactgcactt atcagtccag ctattcaact tttctattct ggtatgtcca gtatctaaac   180
aaagagcctg agctcctcct gaaaagttca gaaaaccagg agacggacag cagaggtttt   240
caggccagtc ctatcaagag tgacagttcc ttccacctgg agaagccctc ggtgcagctg   300
tcggactctg ccgtgtacta ctgcgctctg agaga                              335
```

<210> SEQ ID NO 70
<211> LENGTH: 350
<212> TYPE: DNA
<213> ORGANISM: Homo sapiens

<400> SEQUENCE: 70

```
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctgta caagcaacca     180
ccaagtggag aattggtttt ccttattcgt cggaactctt tgatgagca aatgaaata      240
agtggtcggt attcttggaa cttccagaaa tccaccagtt ccttcaactt caccatcaca    300
gcctcacaag tcgtggactc agcagtatac ttctgtgctc tgagtgaggc                350
```

<210> SEQ ID NO 71
<211> LENGTH: 337
<212> TYPE: DNA
<213> ORGANISM: Homo sapiens

<400> SEQUENCE: 71

```
atggagaaaa tgttggagtg tgcattcata gtcttgtggc ttcagcttgg ctggttgagt      60
ggagaagacc aggtgacgca gagtcccgag gccctgagac tccaggaggg agagagtagc    120
agtcttaact gcagttacac agtcagcggt ttaagagggc tgttctggta taggcaagat    180
cctgggaaag gccctgaatt cctcttcacc ctgtattcag ctggggaaga aaggagaaa     240
gaaaggctaa agccacatt aacaaagaag gaaagctttc tgcacatcac agcccctaaa    300
cctgaagact cagccactta tctctgtgct gtgcagg                             337
```

<210> SEQ ID NO 72
<211> LENGTH: 336
<212> TYPE: DNA
<213> ORGANISM: Homo sapiens

<400> SEQUENCE: 72

```
atggagaccc tcttgggcct gcttatcctt tggctgcagc tgcaatgggt gagcagcaaa      60
caggaggtga cgcagattcc tgcagctctg agtgtcccag aaggagaaaa cttggttctc    120
aactgcagtt tcactgatag cgctatttac aacctccagt ggtttaggca ggaccctggg    180
aaaggtctca catctctgtt gcttattcag tcaagtcaga gagagcaaac aagtggaaga    240
cttaatgcct cgctggataa atcatcagga cgtagtactt tatacattgc agcttctcag    300
cctggtgact cagccaccta cctctgtgct gtgagg                               336
```

<210> SEQ ID NO 73
<211> LENGTH: 331
<212> TYPE: DNA
<213> ORGANISM: Homo sapiens

<400> SEQUENCE: 73

```
atgaagagga tattgggagc tctgctgggg ctcttgagtg cccaggtttg ctgtgtgaga      60
ggaatacaag tggagcagag tcctccagac ctgattctcc aggagggagc caattccacg    120
ctgcggtgca ttttctga ctctgtgaac aatttgcagt ggtttcatca aaacccttgg      180
ggacagctca tcaacctgtt ttacattccc tcagggacaa acagaatgg aagattaagc     240
gccacgactg tcgctacgga acgctacagc ttattgtaca tttcctcttc ccagaccaca    300
gactcaggcg tttatttctg tgctgtggag c                                    331
```

<210> SEQ ID NO 74
<211> LENGTH: 364
<212> TYPE: DNA
<213> ORGANISM: Homo sapiens

<400> SEQUENCE: 74

```
atggacaaga tcttaggagc atcatttta gttctgtggc ttcaactatg ctgggtgagt    60
ggccaacaga aggagaaaag tgaccagcag caggtgaaac aaagtcctca atctttgata  120
gtccagaaag gagggatttc aattataaac tgtgcttatg agaacactgc gtttgactac  180
tttccatggt accaacaatt ccctgggaaa ggccctgcat tattgatagc catacgtcca  240
gatgtgagtg aaaagaaaga aggaagattc acaatctcct tcaataaaag tgccaagcag  300
ttctcattgc atatcatgga ttcccagcct ggagactcag ccacctactt ctgtgcagca  360
agca                                                               364
```

<210> SEQ ID NO 75
<211> LENGTH: 343
<212> TYPE: DNA
<213> ORGANISM: Homo sapiens

<400> SEQUENCE: 75

```
atggagaaga atcctttggc agccccatta ctaatcctct ggtttcatct tgactgcgtg    60
agcagcatac tgaacgtgga acaaagtcct cagtcactgc atgttcagga gggagacagc  120
accaatttca cctgcagctt cccttccagc aattttatg ccttacactg gtacagatgg   180
gaaactgcaa aaagccccga ggccttgttt gtaatgactt aaatggggga tgaaaagaag  240
aaaggacgaa taagtgccac tcttaatacc aaggagggtt acagctattt gtacatcaaa  300
ggatcccagc ctgaagactc agccacatac ctctgtgcct tta                    343
```

<210> SEQ ID NO 76
<211> LENGTH: 327
<212> TYPE: DNA
<213> ORGANISM: Homo sapiens

<400> SEQUENCE: 76

```
atgctactca tcacatcaat gttggtctta tggatgcaat tgtcacaggt gaatggacaa    60
caggtaatgc aaattcctca gtaccagcat gtacaagaag gagaggactt caccacgtac  120
tgcaattcct caactacttt aagcaatata cagtggtata agcaaaggcc tggtggacat  180
cccgttttt tgatacagtt agtgaagagt ggagaagtga agaagcagaa aagactgaca  240
tttcagtttg gagaagcaaa aaagaacagc tccctgcaca tcacagccac ccagactaca  300
gatgtaggaa cctacttctg tgcaggg                                      327
```

<210> SEQ ID NO 77
<211> LENGTH: 328
<212> TYPE: DNA
<213> ORGANISM: Homo sapiens

<400> SEQUENCE: 77

```
atgaggctgg tggcaagagt aactgtgttt ctgacctttg gaactataat tgatgctaag    60
accacccagc cccctccat ggattgcgct gaaggaagag ctgcaaacct gccttgtaat   120
cactctacca tcagtggaaa tgagtatgtg tattggtatc gacagattca ctcccagggg  180
ccacagtata tcattcatgg tctaaaaaac aatgaaacca atgaaatggc ctctctgatc  240
atcacagaag acagaaagtc cagcaccttg atcctgcccc acgctacgct gagagacact  300
gctgtgtact attgcatcgt cagagtcg                                     328
```

<210> SEQ ID NO 78

```
<211> LENGTH: 327
<212> TYPE: DNA
<213> ORGANISM: Homo sapiens

<400> SEQUENCE: 78
atgaagttgg tgacaagcat tactgtactc ctatctttgg gtattatggg tgatgctaag      60
accacacagc caaattcaat ggagagtaac gaagaagagc ctgttcactt gccttgtaac     120
cactccacaa tcagtggaac tgattacata cattggtatc gacagcttcc ctcccagggt     180
ccagagtacg tgattcatgg tcttacaagc aatgtgaaca acagaatggc ctctctggca     240
atcgctgaag acagaaagtc cagtaccttg atcctgcacc gtgctacctt gagagatgct     300
gctgtgtact actgcatcct gagagac                                        327

<210> SEQ ID NO 79
<211> LENGTH: 328
<212> TYPE: DNA
<213> ORGANISM: Homo sapiens

<400> SEQUENCE: 79
atggtcctga aattctccgt gtccattctt tggattcagt tggcatgggt gagcacccag      60
ctgctggagc agagccctca gtttctaagc atccaagagg gagaaaatct cactgtgtac     120
tgcaactcct caagtgtttt ttccagctta caatggtaca gacaggagcc tggggaaggt     180
cctgtcctcc tggtgacagt agttacgggt ggagaagtga agaagctgaa gagactaacc     240
tttcagtttg gtgatgcaag aaaggacagt tctctccaca tcactgcagc ccagcctggt     300
gatacaggcc tctacctctg tgcaggag                                       328

<210> SEQ ID NO 80
<211> LENGTH: 358
<212> TYPE: DNA
<213> ORGANISM: Homo sapiens

<400> SEQUENCE: 80
atggccatgc tcctgggggc atcagtgctg attctgtggc ttcagccaga ctgggtaaac      60
agtcaacaga gaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgc tgaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaagcg     358

<210> SEQ ID NO 81
<211> LENGTH: 337
<212> TYPE: DNA
<213> ORGANISM: Homo sapiens

<400> SEQUENCE: 81
atggagactc tcctgaaagt gctttcaggc accttgttgt ggcagttgac ctgggtgaga      60
agccaacaac cagtgcagag tcctcaagcc gtgatcctcc gagaagggga agatgctgtc     120
atcaactgca gttcctccaa ggctttatat tctgtacact ggtacaggca agcatggt      180 gaagcacccg tcttcctgat gatattactg aagggtggag aacagaaggg tcatgaaaaa     240
atatctgctt catttaatga aaaaaagcag caaagctccc tgtaccttac ggcctcccag     300
ctcagttact caggaaccta cttctgcggc acagaga                             337
```

```
<210> SEQ ID NO 82
<211> LENGTH: 337
<212> TYPE: DNA
<213> ORGANISM: Homo sapiens

<400> SEQUENCE: 82
atggagactg ttctgcaagt actcctaggg atattggggt tccaagcagc ctgggtcagt      60
agccaagaac tggagcagag tcctcagtcc ttgatcgtcc aagagggaaa gaatctcacc     120
ataaactgca cgtcatcaaa gacgttatat ggcttatact ggtataagca aaagtatggt     180
gaaggtctta tcttcttgat gatgctacag aaaggtgggg aagagaaaag tcatgaaaag     240
ataactgcca agttggatga aaaaagcag caaagttccc tgcatatcac agcctcccag      300
cccagccatg caggcatcta cctctgtgga gcagaca                              337

<210> SEQ ID NO 83
<211> LENGTH: 330
<212> TYPE: DNA
<213> ORGANISM: Homo sapiens

<400> SEQUENCE: 83
atgctccttg aacatttatt aataatcttg tggatgcagc tgacatgggt cagtggtcaa      60
cagctgaatc agagtcctca atctatgttt atccaggaag gagaagatgt ctccatgaac     120
tgcacttctt caagcatatt taacacctgg ctatggtaca gcaggaacc tggggaaggt      180 cctgtcctct tgatagcctt atataaggct ggtgaattga cctcaaatgg aagactgact     240
gctcagtttg gtataaccag aaaggacagc ttcctgaata tctcagcatc catacctagt     300
gatgtaggca tctacttctg tgctgggcag                                      330

<210> SEQ ID NO 84
<211> LENGTH: 340
<212> TYPE: DNA
<213> ORGANISM: Homo sapiens

<400> SEQUENCE: 84
atgatgaagt gtccacaggc tttactagct atcttttggc ttctactgag ctgggtgagc      60
agtgaagaca aggtggtaca aagccctcta tctctggttg tccacgaggg agacaccgta     120
actctcaatt gcagttatga agtgactaac tttcgaagcc tactatggta caagcaggaa     180
aagaaagctc ccacatttct atttatgcta acttcaagtg gaattgaaaa gaagtcagga     240
agactaagta gcatattaga taagaaagaa cttttccagca tcctgaacat cacagccacc     300
cagaccggag actcggccat ctacctctgt gctgtggagg                           340

<210> SEQ ID NO 85
<211> LENGTH: 350
<212> TYPE: DNA
<213> ORGANISM: Homo sapiens

<400> SEQUENCE: 85
atgacacgag ttagcttgct gtgggcagtc gtggtctcca cctgtcttga atccggcatg      60
gcccagacag tcactcagtc tcaaccagag atgtctgtgc aggaggcaga gactgtgacc     120
ctgagttgca catatgacac cagtgagaat aattattatt tgttctggta caagcagcct     180
cccagcaggc agatgattct cgttattcgc caagaagctt ataagcaaca gaatgcaacg     240
gagaatcgtt tctctgtgaa cttccagaaa gcagccaaat ccttcagtct caagatctca     300
gactcacagc tgggggacac tgcgatgtat ttctgtgctt tcatgaagca                350
```

<210> SEQ ID NO 86
<211> LENGTH: 349
<212> TYPE: DNA
<213> ORGANISM: Homo sapiens

<400> SEQUENCE: 86

```
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tggggatgc cgcgatgtat ttctgtgctt ataggagcg                   349
```

<210> SEQ ID NO 87
<211> LENGTH: 331
<212> TYPE: DNA
<213> ORGANISM: Homo sapiens

<400> SEQUENCE: 87

```
atgaagaagc tactagcaat gattctgtgg cttcaactag accggttaag tggagagctg      60
aaagtggaac aaaaccctct gttcctgagc atgcaggagg gaaaaaacta taccatctac     120
tgcaattatt caaccacttc agacagactg tattggtaca ggcaggatcc tgggaaaagt     180
ctggaatctc tgtttgtgtt gctatcaaat ggagcagtga agcaggaggg acgattaatg     240
gcctcacttg ataccaaagc ccgtctcagc accctccaca tcacagctgc cgtgcatgac     300
ctctctgcca cctacttctg tgccgtggac a                                     331
```

<210> SEQ ID NO 88
<211> LENGTH: 317
<212> TYPE: DNA
<213> ORGANISM: Homo sapiens

<400> SEQUENCE: 88

```
atgaactcct ctctggactt tctaattctg atcttaatgt ttggaggaac cagcagcaat      60
tcagtcaagc agacgggcca ataaccgtc tcggagggag catctgtgac tatgaactgc     120
acatacacat ccacggggta ccctacccct ttctggtatg tggaataccc cagcaaacct     180
ctgcagcttc ttcagagaga gacaatggaa acagcaaaaa acttcggagg cggaaatatt     240
aaagacaaaa actcccccat tgtgaaatat tcagtccagg tatcagactc agccgtgtac     300
tactgtcttc tgggaga                                                     317
```

<210> SEQ ID NO 89
<211> LENGTH: 336
<212> TYPE: DNA
<213> ORGANISM: Homo sapiens

<400> SEQUENCE: 89

```
atggtgaaga tccggcaatt tttgttggct attttgtggc ttcagctaag ctgtgtaagt      60
gccgccaaaa atgaagtgga gcagagtcct cagaacctga ctgcccagga aggagaattt     120
atcacaatca actgcagtta ctcggtagga ataagtgcct acactggct gcaacagcat     180
ccaggaggag gcattgtttc cttgtttatg ctgagctcag ggaagaagaa gcatggaaga     240
ttaattgcca caataaacat acaggaaaag cacagctccc tgcacatcac agcctcccat     300
cccagagact ctgccgtcta catctgtgct gtcaga                                336
```

<210> SEQ ID NO 90
<211> LENGTH: 533
<212> TYPE: DNA
<213> ORGANISM: Homo sapiens

<400> SEQUENCE: 90

| | | | | | |
|---|---|---|---|---|---|
| aggacctgaa | caaggtgttc | ccacccgagg | tcgctgtgtt | tgagccatca gaagcagaga | 60 |
| tctcccacac | ccaaaaggcc | acactggtgt | gcctggccac | aggcttcttc cccgaccacg | 120 |
| tggagctgag | ctggtgggtg | aatgggaagg | aggtgcacag | tggggtcagc acagacccgc | 180 |
| agccctcaa | ggagcagccc | gccctcaatg | actccagata | ctgcctgagc agccgcctga | 240 |
| gggtctcggc | caccttctgg | cagaaccccc | gcaaccactt | ccgctgtcaa gtccagttct | 300 |
| acgggctctc | ggagaatgac | gagtggaccc | aggatagggc | caaacccgtc acccagatcg | 360 |
| tcagcgccga | ggcctggggt | agagcagact | gtggctttac | ctcggtgtcc taccagcaag | 420 |
| gggtcctgtc | tgccaccatc | ctctatgaga | tcctgctagg | gaaggccacc ctgtatgctg | 480 |
| tgctggtcag | cgcccttgtg | ttgatggcca | tggtcaagag | aaaggatttc tga | 533 |

<210> SEQ ID NO 91
<211> LENGTH: 539
<212> TYPE: DNA
<213> ORGANISM: Homo sapiens

<400> SEQUENCE: 91

| | | | | | |
|---|---|---|---|---|---|
| aggacctgaa | aaacgtgttc | ccacccgagg | tcgctgtgtt | tgagccatca gaagcagaga | 60 |
| tctcccacac | ccaaaaggcc | acactggtat | gcctggccac | aggcttctac cccgaccacg | 120 |
| tggagctgag | ctggtgggtg | aatgggaagg | aggtgcacag | tggggtcagc acagacccgc | 180 |
| agccctcaa | ggagcagccc | gccctcaatg | actccagata | ctgcctgagc agccgcctga | 240 |
| gggtctcggc | caccttctgg | cagaaccccc | gcaaccactt | ccgctgtcaa gtccagttct | 300 |
| acgggctctc | ggagaatgac | gagtggaccc | aggatagggc | caaacccgtc acccagatcg | 360 |
| tcagcgccga | ggcctggggt | agagcagact | gtggcttcac | ctccgagtct taccagcaag | 420 |
| gggtcctgtc | tgccaccatc | ctctatgaga | tcttgctagg | gaaggccacc ttgtatgccg | 480 |
| tgctggtcag | tgccctcgtg | ctgatggcca | tggtcaagag | aaaggattcc agaggctag | 539 |

<210> SEQ ID NO 92
<211> LENGTH: 347
<212> TYPE: DNA
<213> ORGANISM: Homo sapiens

<400> SEQUENCE: 92

| | | | | | |
|---|---|---|---|---|---|
| atggatacct | ggctcgtatg | ctgggcaatt | tttagtctct | tgaaagcagg actcacagaa | 60 |
| cctgaagtca | cccagactcc | cagccatcag | gtcacacaga | tgggacagga agtgatcttg | 120 |
| cgctgtgtcc | ccatctctaa | tcacttatac | ttctattggt | acagacaaat cttggggcag | 180 |
| aaagtcgagt | ttctggtttc | cttttataat | aatgaaatct | cagagaagtc tgaaatattc | 240 |
| gatgatcaat | tctcagttga | aaggcctgat | ggatcaaatt | tcactctgaa gatccggtcc | 300 |
| acaaagctgg | aggactcagc | catgtacttc | tgtgccagca | gtgaagc | 347 |

<210> SEQ ID NO 93
<211> LENGTH: 344
<212> TYPE: DNA
<213> ORGANISM: Homo sapiens

<400> SEQUENCE: 93

```
atgggctgca ggctcctctg ctgtgtggtc ttctgcctcc tccaagcagg tcccttggac      60
acagctgttt cccagactcc aaaatacctg gtcacacaga tgggaaacga caagtccatt    120
aaatgtgaac aaaatctggg ccatgatact atgtattggt ataaacagga ctctaagaaa    180
tttctgaaga taatgtttag ctacaataat aaggagctca ttataaatga aacagttcca    240
aatcgcttct cacctaaatc tccagacaaa gctcacttaa atcttcacat caattccctg    300
gagcttggtg actctgctgt gtatttctgt gccagcagcc aaga                     344
```

<210> SEQ ID NO 94
<211> LENGTH: 344
<212> TYPE: DNA
<213> ORGANISM: Homo sapiens

<400> SEQUENCE: 94

```
atgggctgca ggctgctctg ctgtgcggtt ctctgtctcc tgggagcagt tcccatagac      60
actgaagtta cccagacacc aaaacacctg gtcatgggaa tgacaaataa gaagtctttg    120
aaatgtgaac aacatatggg gcacagggct atgtattggt acaagcagaa agctaagaag    180
ccaccggagc tcatgtttgt ctacagctat gagaaactct ctataaatga aagtgtgcca    240
agtcgcttct cacctgaatg ccccaacagc tctctcttaa accttcacct cacgccctg    300
cagccagaag actcagccct gtatctctgc gccagcagcc aaga                     344
```

<210> SEQ ID NO 95
<211> LENGTH: 344
<212> TYPE: DNA
<213> ORGANISM: Homo sapiens

<400> SEQUENCE: 95

```
atgggctgca ggctgctctg ctgtgcggtt ctctgtctcc tgggagcggt ccccatggaa      60
acgggagtta cgcagacacc aagacacctg gtcatgggaa tgacaaataa gaagtctttg    120
aaatgtgaac aacatctggg gcataacgct atgtattggt acaagcaaag tgctaagaag    180
ccactggagc tcatgtttgt ctacaacttt aaagaacaga ctgaaaacaa cagtgtgcca    240
agtcgcttct cacctgaatg ccccaacagc tctcacttat tccttcacct acacaccctg    300
cagccagaag actcggccct gtatctctgt gccagcagcc aaga                     344
```

<210> SEQ ID NO 96
<211> LENGTH: 344
<212> TYPE: DNA
<213> ORGANISM: Homo sapiens

<400> SEQUENCE: 96

```
atgggctgca ggctgctctg ctgtgcggtt ctctgtctcc tgggagcggt ccccatggaa      60
acgggagtta cgcagacacc aagacacctg gtcatgggaa tgacaaataa gaagtctttg    120
aaatgtgaac aacatctggg tcataacgct atgtattggt acaagcaaag tgctaagaag    180
ccactggagc tcatgtttgt ctacagtctt gaagaacggg ttgaaaacaa cagtgtgcca    240
agtcgcttct cacctgaatg ccccaacagc tctcacttat tccttcacct acacaccctg    300
cagccagaag actcggccct gtatctctgc gccagcagcc aaga                     344
```

<210> SEQ ID NO 97
<211> LENGTH: 343
<212> TYPE: DNA
<213> ORGANISM: Homo sapiens

<400> SEQUENCE: 97

```
atgggctcca ggctgctctg ttgggtgctg ctttgtctcc tgggagcagg cccagtaaag    60
gctggagtca ctcaaactcc aagatatctg atcaaaacga gaggacagca agtgacactg   120
agctgctccc ctatctctgg gcataggagt gtatcctggt accaacagac cccaggacag   180
ggccttcagt tcctctttga atacttcagt gagacacaga gaaacaaagg aaacttccct   240
ggtcgattct cagggcgcca gttctctaac tctcgctctg agatgaatgt gagcaccttg   300
gagctggggg actcggccct ttatctttgc gccagcagct tgg                     343
```

<210> SEQ ID NO 98
<211> LENGTH: 341
<212> TYPE: DNA
<213> ORGANISM: Homo sapiens

<400> SEQUENCE: 98

```
atgggccccg ggctcctctg ctgggaactg ctttatctcc tgggagcagg cccagtggag    60
gctggagtca cccaaagtcc cacacacctg atcaaaacga gaggacagca agtgactctg   120
agatgctctc ctatctctgg gcacagcagt gtgtcctggt accaacaggc cccgggtcag   180
ggcccccagt ttatctttga atatgctaat gagttaagga gatcagaagg aaacttccct   240
aatcgattct cagggcgcca gttccatgac tgttgctctg agatgaatgt gagtgccttg   300
gagctggggg actcggccct gtatctctgt gccagaagct t                       341
```

<210> SEQ ID NO 99
<211> LENGTH: 343
<212> TYPE: DNA
<213> ORGANISM: Homo sapiens

<400> SEQUENCE: 99

```
atgggccctg ggctcctctg ctgggtgctg ctttgtctcc tgggagcagg ctcagtggag    60
actggagtca cccaaagtcc cacacacctg atcaaaacga gaggacagca agtgactctg   120
agatgctctt ctcagtctgg gcacaacact gtgtcctggt accaacaggc cctgggtcag   180
ggcccccagt ttatctttca gtattatagg gaggaagaga atggcagagg aaacttccct   240
cctagattct caggtctcca gttccctaat tatagctctg agctgaatgt gaacgccttg   300
gagctggacg actcggccct gtatctctgt gccagcagct tgg                     343
```

<210> SEQ ID NO 100
<211> LENGTH: 343
<212> TYPE: DNA
<213> ORGANISM: Homo sapiens

<400> SEQUENCE: 100

```
atgggccctg ggctcctctg ctgggtgctg ctttgtctcc tgggagcagg cccagtggac    60
gctggagtca cccaaagtcc cacacacctg atcaaaacga gaggacagca agtgactctg   120
agatgctctc ctatctctgg gcacaagagt gtgtcctggt accaacaggt cctgggtcag   180
ggcccccagt ttatctttca gtattatgag aagaagaga gaggaagagg aaacttccct   240
gatcgattct cagctcgcca gttccctaac tatagctctg agctgaatgt gaacgccttg   300
ttgctggggg actcggccct gtatctctgt gccagcagct tgg                     343
```

<210> SEQ ID NO 101
<211> LENGTH: 343
<212> TYPE: DNA

<213> ORGANISM: Homo sapiens

<400> SEQUENCE: 101

| | | |
|---|---|---|
| atgggcccncg ggctcctctg ctgggcactg ctttgtctcc tgggagcagg cttagtggac | 60 |
| gctggagtca cccaaagtcc cacacacctg atcaaaacga gaggacagca agtgactctg | 120 |
| agatgctctc ctaagtctgg gcatgacact gtgtcctggt accaacaggc cctgggtcag | 180 |
| ggcccccagt ttatctttca gtattatgag gaggaagaga gacagagagg caacttccct | 240 |
| gatcgattct caggtcacca gttccctaac tatagctctg agctgaatgt gaacgccttg | 300 |
| ttgctggggg actcggccct ctatctctgt gccagcagct tgg | 343 |

<210> SEQ ID NO 102
<211> LENGTH: 343
<212> TYPE: DNA
<213> ORGANISM: Homo sapiens

<400> SEQUENCE: 102

| | | |
|---|---|---|
| atgggcccncg ggctcctctg ctgggtgctg ctttgtcccc taggagaagg cccagtggac | 60 |
| gctggagtca cccaaagtcc cacacacctg atcaaaacga gaggacagca cgtgactctg | 120 |
| agatgctctc ctatctctgg gcacaccagt gtgtcctcgt accaacaggc cctgggtcag | 180 |
| ggcccccagt ttatctttca gtattatgag aagaagaga gaggaagagg aaacttccct | 240 |
| gatcaattct caggtcacca gttccctaac tatagctctg agctgaatgt gaacgccttg | 300 |
| ttgctagggg actcggccct ctatctctgt gccagcagct tgg | 343 |

<210> SEQ ID NO 103
<211> LENGTH: 343
<212> TYPE: DNA
<213> ORGANISM: Homo sapiens

<400> SEQUENCE: 103

| | | |
|---|---|---|
| atgggaccca ggctcctctt ctgggcactg ctttgtctcc tcggaacagg cccagtggag | 60 |
| gctggagtca cacaaagtcc cacacacctg atcaaaacga gaggacagca agcgactctg | 120 |
| agatgctctc ctatctctgg gcacaccagt gtgtactggt accaacaggc cctgggtctg | 180 |
| ggcctccagt tcctcctttg gtatgacgag ggtgaagaga gaaacagagg aaacttccct | 240 |
| cctagatttt caggtcgcca gttccctaat tatagctctg agctgaatgt gaacgccttg | 300 |
| gagctggagg actcggccct gtatctctgt gccagcagct tgg | 343 |

<210> SEQ ID NO 104
<211> LENGTH: 344
<212> TYPE: DNA
<213> ORGANISM: Homo sapiens

<400> SEQUENCE: 104

| | | |
|---|---|---|
| atgagcatcg ggctcctgtg ctgtgtggcc ttttctctcc tgtgggcaag tccagtgaat | 60 |
| gctggtgtca ctcagacccc aaaattccag gtcctgaaga caggacagag catgacactg | 120 |
| cagtgtgccc aggatatgaa ccataactcc atgtactggt atcgacaaga cccaggcatg | 180 |
| ggactgaggc tgatttatta ctcagcttct gagggtacca ctgacaaagg agaagtcccc | 240 |
| aatggctaca atgtctccag attaaacaaa cgggagttct cgctcaggct ggagtcggct | 300 |
| gctccctccc agacatctgt gtacttctgt gccagcagtg aagc | 344 |

<210> SEQ ID NO 105
<211> LENGTH: 344

<212> TYPE: DNA
<213> ORGANISM: Homo sapiens

<400> SEQUENCE: 105

```
atgagcctcg ggctcctgtg ctgtggggcc ttttctctcc tgtgggcagg tccagtgaat    60
gctggtgtca ctcagacccc aaaattccgg gtcctgaaga caggacagag catgacactg   120
ctgtgtgccc aggatatgaa ccatgaatac atgtactggt atcgacaaga cccaggcatg   180
gggctgaggc tgattcatta ctcagttggt gagggtacaa ctgccaaagg agaggtccct   240
gatggctaca atgtctccag attaaaaaaa cagaatttcc tgctggggtt ggagtcggct   300
gctccctccc aaacatctgt gtacttctgt gccagcagtt actc                   344
```

<210> SEQ ID NO 106
<211> LENGTH: 344
<212> TYPE: DNA
<213> ORGANISM: Homo sapiens

<400> SEQUENCE: 106

```
atgagcctcg ggctcctgtg ctgtggggtc ttttctctcc tgtgggcagg tccagtgaat    60
gctggtgtca ctcagacccc aaaattccgg gtcctgaaga caggacagag catgacactg   120
ctgtgtgccc aggatatgaa ccatgaatac atgtactggt atcgacaaga cccaggcatg   180
gggctgaggc tgattcatta ctcagttggt gagggtacaa ctgccaaagg agaggtccct   240
gatggctaca atgtctccag attaaaaaaa cagaatttcc tgctggggtt ggagtcggct   300
gctccctccc aaacatctgt gtacttctgt gccagcagtt actc                   344
```

<210> SEQ ID NO 107
<211> LENGTH: 344
<212> TYPE: DNA
<213> ORGANISM: Homo sapiens

<400> SEQUENCE: 107

```
atgagaatca ggctcctgtg ctgtgtggcc ttttctctcc tgtgggcagg tccagtgatt    60
gctgggatca cccaggcacc aacatctcag atcctggcag caggacggcg catgacactg   120
agatgtaccc aggatatgag acataatgcc atgtactggt atagacaaga tctaggactg   180
gggctaaggc tcatccatta ttcaaatact gcaggtacca ctggcaaagg agaagtccct   240
gatggttata gtgtctccag agcaaacaca gatgatttcc ccctcacgtt ggcgtctgct   300
gtaccctctc agacatctgt gtacttctgt gccagcagtg actc                   344
```

<210> SEQ ID NO 108
<211> LENGTH: 344
<212> TYPE: DNA
<213> ORGANISM: Homo sapiens

<400> SEQUENCE: 108

```
atgagcatcg gcctcctgtg ctgtgcagcc ttgtctctcc tgtgggcagg tccagtgaat    60
gctggtgtca ctcagacccc aaaattccag gtcctgaaga caggacagag catgacactg   120
cagtgtgccc aggatatgaa ccatgaatac atgtcctggt atcgacaaga cccaggcatg   180
gggctgaggc tgattcatta ctcagttggt gctggtatca ctgaccaagg agaagtcccc   240
aatggctaca atgtctccag atcaaccaca gaggatttcc cgctcaggct gctgtcggct   300
gctccctccc agacatctgt gtacttctgt gccagcagtt actc                   344
```

<210> SEQ ID NO 109

<211> LENGTH: 344
<212> TYPE: DNA
<213> ORGANISM: Homo sapiens

<400> SEQUENCE: 109

```
atgagcatca gcctcctgtg ctgtgcagcc tttcctctcc tgtgggcagg tccagtgaat      60
gctggtgtca ctcagacccc aaaattccgc atcctgaaga taggacagag catgacactg     120
cagtgtaccc aggatatgaa ccataactac atgtactggt atcgacaaga cccaggcatg     180
gggctgaagc tgatttatta ttcagttggt gctggtatca ctgataaagg agaagtcccg     240
aatggctaca cgtctccag atcaaccaca gaggatttcc cgctcaggct ggagttggct     300
gctccctccc agacatctgt gtacttctgt gccagcagtt actc                      344
```

<210> SEQ ID NO 110
<211> LENGTH: 344
<212> TYPE: DNA
<213> ORGANISM: Homo sapiens

<400> SEQUENCE: 110

```
atgagcctcg ggctcctgtg ctgtgtggcc ttttctctcc tgtgggcagg tccaatgaat      60
gctggtgtca ctcagacccc aaaattccac gtcctgaaga caggacagag catgactctg     120
ctgtgtgccc aggatatgaa ccatgaatac atgtatcggt atcgacaaga cccaggcaag     180
gggctgaggc tgatttacta ctcagttgct gctgctctca ctgacaaagg agaagttccc     240
aatggctaca atgtctccag atcaaacaca gaggatttcc ccctcaagct ggagtcagct     300
gctccctctc agacttctgt ttacttctgt gccagcagtt actc                      344
```

<210> SEQ ID NO 111
<211> LENGTH: 341
<212> TYPE: DNA
<213> ORGANISM: Homo sapiens

<400> SEQUENCE: 111

```
atgagcctcg ggctcctgtg ctgtgcggcc ttttctctcc tgtgggcagg tcccgtgaat      60
gctggtgtca ctcagacccc aaaattccac atcctgaaga caggacagag catgacactg     120
cagtgtgccc aggatatgaa ccatggatac atgtcctggt atcgacaaga cccaggcatg     180
gggctgagac tgatttacta ctcagctgct gctggtacta ctgacaaaga agtcccaat     240
ggctacaatg tctctagatt aaacacagag gatttcccac tcaggctggt gtcggctgct     300
ccctcccaga catctgtgta cttgtgtgcc agcagttact c                         341
```

<210> SEQ ID NO 112
<211> LENGTH: 344
<212> TYPE: DNA
<213> ORGANISM: Homo sapiens

<400> SEQUENCE: 112

```
atgagcatcg ggctcctgtg ctgtgtggcc ttttctctcc tgtgggcagg tccagtgaat      60
gctggtgtca ctcagacccc aaaattccac atcctgaaga caggacagag catgacactg     120
cagtgtgccc aggatatgaa ccatggatac ttgtcctggt atcgacaaga cccaggcatg     180
gggctgaggc gcattcatta ctcagttgct gctggtatca ctgacaaagg agaagtcccc     240
gatggctaca atgtatccag atcaaacaca gaggatttcc cgctcaggct ggagtcagct     300
gctccctccc agacatctgt atacttctgt gccagcagtt attc                      344
```

<210> SEQ ID NO 113
<211> LENGTH: 347
<212> TYPE: DNA
<213> ORGANISM: Homo sapiens

<400> SEQUENCE: 113

```
atgggcacaa ggctcctctg ctgggcagcc atatgtctcc tgggggcaga tcacacaggt    60
gctggagtct cccagtccct gagacacaag gtagcaaaga agggaaagga tgtagctctc   120
agatatgatc aatttcagg tcataatgcc ctttattggt accgacagag cctggggcag    180
ggcctggagt ttccaattta cttccaaggc aaggatgcag cagacaaatc ggggcttccc   240
cgtgatcggt tctctgcaca gaggtctgag ggatccatct ccactctgaa gttccagcgc   300
acacagcagg gggacttggc tgtgtatctc tgtgccagca gctcagc                  347
```

<210> SEQ ID NO 114
<211> LENGTH: 347
<212> TYPE: DNA
<213> ORGANISM: Homo sapiens

<400> SEQUENCE: 114

```
atgggcacca ggctcctctt ctgggtggcc ttctgtctcc tgggggcaga tcacacagga    60
gctggagtct cccagtcccc cagtaacaag gtcacagaga agggaaagga tgtagagctc   120
aggtgtgatc aatttcagg tcatactgcc ctttactggt accgacagag cctggggcag    180
ggcctggagt ttttaattta cttccaaggc aacagtgcac cagacaaatc agggctgccc   240
agtgatcgct tctctgcaga gaggactggg ggatccgtct ccactctgac gatccagcgc   300
acacagcagg aggactcggc cgtgtatctc tgtgccagca gcttagc                  347
```

<210> SEQ ID NO 115
<211> LENGTH: 347
<212> TYPE: DNA
<213> ORGANISM: Homo sapiens

<400> SEQUENCE: 115

```
atgggcacca ggctcctctg ctgggcagcc ctgtgcctcc tgggggcaga tcacacaggt    60
gctggagtct cccagacccc cagtaacaag gtcacagaga agggaaaata tgtagagctc   120
aggtgtgatc aatttcagg tcatactgcc ctttactggt accgacaaag cctggggcag    180
ggcccagagt ttctaattta cttccaaggc acgggtgcgg cagatgactc agggctgccc   240
aacgatcggt tctttgcagt caggcctgag ggatccgtct ctactctgaa gatccagcgc   300
acagagcggg gggactcagc cgtgtatctc tgtgccagca gcttaac                  347
```

<210> SEQ ID NO 116
<211> LENGTH: 347
<212> TYPE: DNA
<213> ORGANISM: Homo sapiens

<400> SEQUENCE: 116

```
atgggcacca ggctcctctg ctgggtggtc ctgggtttcc tagggacaga tcacacaggt    60
gctggagtct cccagtcccc aaggtacaaa gtcgcaaaga gggacgggga tgtagctctc   120
aggtgtgatt caatttcggg tcatgtaacc ctttattggt accgacagac cctggggcag   180
ggctcagagg ttctgactta ctcccagagt gatgctcaac gagacaaatc agggcggccc   240
agtggtcggt tctctgcaga gaggcctgag agatccgtct ccactctgaa gatccagcgc   300
acagagcagg gggactcagc tgtgtatctc tgtgccagca gcttagc                  347
```

<210> SEQ ID NO 117
<211> LENGTH: 347
<212> TYPE: DNA
<213> ORGANISM: Homo sapiens

<400> SEQUENCE: 117

| | | | | | |
|---|---|---|---|---|---|
| atgggcacca | gtctcctatg | ctgggtggtc | ctgggtttcc | tagggacaga | tcacacaggt | 60 |
| gctggagtct | cccagtctcc | caggtacaaa | gtcacaaaga | gggacagga | tgtagctctc | 120 |
| aggtgtgatc | caatttcggg | tcatgtatcc | ctttattggt | accgacaggc | cctggggcag | 180 |
| ggcccagagt | ttctgactta | cttcaattat | gaagcccaac | aagacaaatc | agggctgccc | 240 |
| aatgatcggt | tctctgcaga | gaggcctgag | ggatccatct | ccactctgac | gatccagcgc | 300 |
| acagagcagc | gggactcggc | catgtatcgc | tgtgccagca | gcttagc | | 347 |

<210> SEQ ID NO 118
<211> LENGTH: 347
<212> TYPE: DNA
<213> ORGANISM: Homo sapiens

<400> SEQUENCE: 118

| | | | | | |
|---|---|---|---|---|---|
| atgggtacca | gtctcctatg | ctgggtggtc | ctgggtttcc | tagggacaga | tcacacaggt | 60 |
| gctggagtct | cccagtctcc | caggtacaaa | gtcacaaaga | ggggacagga | tgtaactctc | 120 |
| aggtgtgatc | caatttcgag | tcatgcaacc | ctttattggt | atcaacaggc | cctggggcag | 180 |
| ggcccagagt | ttctgactta | cttcaattat | gaagctcaac | cagacaaatc | agggctgccc | 240 |
| agtgatcggt | tctctgcaga | gaggcctgag | ggatccatct | ccactctgac | gattcagcgc | 300 |
| acagagcagc | gggactcagc | catgtatcgc | tgtgccagca | gcttagc | | 347 |

<210> SEQ ID NO 119
<211> LENGTH: 347
<212> TYPE: DNA
<213> ORGANISM: Homo sapiens

<400> SEQUENCE: 119

| | | | | | |
|---|---|---|---|---|---|
| atgggcacca | ggctcctctg | ctgggtggtc | ctgggtttcc | tagggacaga | tcacacaggt | 60 |
| gctggagtct | cccagtcccc | taggtacaaa | gtcgcaaaga | gaggacagga | tgtagctctc | 120 |
| aggtgtgatc | caatttcggg | tcatgtatcc | ctttttggt | accaacaggc | cctggggcag | 180 |
| gggccagagt | ttctgactta | tttccagaat | gaagctcaac | tagacaaatc | ggggctgccc | 240 |
| agtgatcgct | tctttgcaga | aaggcctgag | ggatccgtct | ccactctgaa | gatccagcgc | 300 |
| acacagcagg | aggactccgc | cgtgtatctc | tgtgccagca | gcttagc | | 347 |

<210> SEQ ID NO 120
<211> LENGTH: 347
<212> TYPE: DNA
<213> ORGANISM: Homo sapiens

<400> SEQUENCE: 120

| | | | | | |
|---|---|---|---|---|---|
| atgggcacca | gcctcctctg | ctggatggcc | ctgtgtctcc | tggggcaga | tcacgcagat | 60 |
| actggagtct | cccagaaccc | cagacacaag | atcacaaaga | ggggacagaa | tgtaactttc | 120 |
| aggtgtgatc | caatttctga | acacaaccgc | ctttattggt | accgacagac | cctggggcag | 180 |
| ggcccagagt | ttctgactta | cttccagaat | gaagctcaac | tagaaaaatc | aaggctgctc | 240 |
| agtgatcggt | tctctgcaga | gaggcctaag | ggatctttct | ccaccttgga | gatccagcgc | 300 |
| acagagcagg | gggactcggc | catgtatctc | tgtgccagca | gcttagc | | 347 |

<210> SEQ ID NO 121
<211> LENGTH: 343
<212> TYPE: DNA
<213> ORGANISM: Homo sapiens

<400> SEQUENCE: 121

```
atgggcttca ggctcctctg ctgtgtggcc ttttgtctcc tgggagcagg cccagtggat      60
tctggagtca cacaaacccc aaagcacctg atcacagcaa ctggacagcg agtgacgctg     120
agatgctccc ctaggtctgg agacctctct gtgtactggt accaacagag cctggaccag     180
ggcctccagt tcctcattca gtattataat ggagaagaga gagcaaaagg aaacattctt     240
gaacgattct ccgcacaaca gttccctgac ttgcactctg aactaaacct gagctctctg     300
gagctggggg actcagcttt gtatttctgt gccagcagcg tag                      343
```

<210> SEQ ID NO 122
<211> LENGTH: 344
<212> TYPE: DNA
<213> ORGANISM: Homo sapiens

<400> SEQUENCE: 122

```
atgggcacga ggctcttctt ctatgtggcc ctttgtctgc tgtgggcagg acacagggat      60
gctgaaatca cccagagccc aagacacaag atcacagaga caggaaggca ggtgaccttg     120
gcgtgtcacc agacttggaa ccacaacaat atgttctggt atcgacaaga cctgggacat     180
ggctgaggc tgatccatta ctcatatggt gttcaagaca ctaacaaagg agaagtctca     240
gatggctaca gtgtctctag atcaaacaca gaggacctcc ccctcactct ggagtctgct     300
gcctcctccc agacatctgt atatttctgc gccagcagtg agtc                     344
```

<210> SEQ ID NO 123
<211> LENGTH: 344
<212> TYPE: DNA
<213> ORGANISM: Homo sapiens

<400> SEQUENCE: 123

```
atgggcacca ggctcttctt ctatgtggcc ctttgtctgc tgtgggcagg acacagggat      60
gctggaatca cccagagccc aagatacaag atcacagaga caggaaggca ggtgaccttg     120
atgtgtcacc agacttggag ccacagctat atgttctggt atcgacaaga cctgggacat     180
ggctgaggc tgatctatta ctcagcagct gctgatatta cagataaagg agaagtcccc     240
gatggctatg ttgtctccag atccaagaca gagaatttcc ccctcactct ggagtcagct     300
acccgctccc agacatctgt gtatttctgc gccagcagtg agtc                     344
```

<210> SEQ ID NO 124
<211> LENGTH: 344
<212> TYPE: DNA
<213> ORGANISM: Homo sapiens

<400> SEQUENCE: 124

```
atgggcacaa ggttgttctt ctatgtggcc ctttgtctcc tgtggacagg acacatggat      60
gctggaatca cccagagccc aagacacaag gtcacagaga caggaacacc agtgactctg     120
agatgtcacc agactgagaa ccaccgctat atgtactggt atcgacaaga cccggggcat     180
gggctgaggc tgatccatta ctcatatggt gttaaagata ctgacaaagg agaagtctca     240
gatggctata gtgtctctag atcaaagaca gaggatttcc tcctcactct ggagtccgct     300
```

```
accagctccc agacatctgt gtacttctgt gccatcagtg agtc        344
```

<210> SEQ ID NO 125
<211> LENGTH: 347
<212> TYPE: DNA
<213> ORGANISM: Homo sapiens

<400> SEQUENCE: 125

```
atgagcacca ggcttctctg ctggatggcc ctctgtctcc tggggcaga actctcagaa     60
gctgaagttg cccagtcccc cagatataag attacagaga aaagccaggc tgtggctttt    120
tggtgtgatc ctatttctgg ccatgctacc ctttactggt accggcagat cctgggacag    180
ggcccggagc ttctggttca atttcaggat gagagtgtag tagatgattc acagttgcct    240
aaggatcgat tttctgcaga gaggctcaaa ggagtagact ccactctcaa gatccagcct    300
gcagagcttg gggactcggc catgtatctc tgtgccagca gcttagc                  347
```

<210> SEQ ID NO 126
<211> LENGTH: 347
<212> TYPE: DNA
<213> ORGANISM: Homo sapiens

<400> SEQUENCE: 126

```
atgggcacca ggctcctctg ctgggcggcc ctctgtctcc tgggagcaga actcacagaa     60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat tttctgcaga gaggctcaaa ggagtagact ccactctcaa gatccagcct    300
gcaaagcttg aggactcggc cgtgtatctc tgtgccagca gcttaga                  347
```

<210> SEQ ID NO 127
<211> LENGTH: 347
<212> TYPE: DNA
<213> ORGANISM: Homo sapiens

<400> SEQUENCE: 127

```
atgggtacca ggctcctctg ctgggtggcc ttctgtctcc tggtggaaga actcatagaa     60
gctggagtgg ttcagtctcc cagatataag attatagaga aaaaacagcc tgtggctttt    120
tggtgcaatc ctatttctgg ccacaatacc ctttactggt acctgcagaa cttgggacag    180
ggcccggagc ttctgattcg atatgagaat gaggaagcag tagacgattc acagttgcct    240
aaggatcgat tttctgcaga gaggctcaaa ggagtagact ccactctcaa gatccagcct    300
gcagagcttg gggactcggc cgtgtatctc tgtgccagca gcttaga                  347
```

<210> SEQ ID NO 128
<211> LENGTH: 347
<212> TYPE: DNA
<213> ORGANISM: Homo sapiens

<400> SEQUENCE: 128

```
atggactcct ggaccttctg ctgtgtgtcc ctttgcatcc tggtagcgaa gcatacagat     60
gctggagtta tccagtcacc ccgccatgag gtgacagaga tgggacaaga agtgactctg    120
agatgtaaac caatttcagg ccacaactcc cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
```

```
tcagaaccca gggactcagc tgtgtacttc tgtgccagca gtttagc              347
```

<210> SEQ ID NO 129
<211> LENGTH: 347
<212> TYPE: DNA
<213> ORGANISM: Homo sapiens

<400> SEQUENCE: 129

```
atggactcct ggaccctctg ctgtgtgtcc ctttgcatcc tggtagcaaa gcacacagat   60
gctggagtta tccagtcacc ccggcacgag gtgacagaga tgggacaaga agtgactctg  120
agatgtaaac caatttcagg acacgactac ctttttctggt acagacagac catgatgcgg  180
ggactggagt tgctcattta ctttaacaac aacgttccga tagatgattc agggatgccc  240
gaggatcgat tctcagctaa gatgcctaat gcatcattct ccactctgaa gatccagccc  300
tcagaaccca gggactcagc tgtgtacttc tgtgccagca gtttagc              347
```

<210> SEQ ID NO 130
<211> LENGTH: 347
<212> TYPE: DNA
<213> ORGANISM: Homo sapiens

<400> SEQUENCE: 130

```
atggccacca ggctcctctg ctgtgtggtt ctttgtctcc tgggagaaga gcttatagat   60
gctagagtca cccagacacc aaggcacaag gtgacagaga tgggacaaga agtaacaatg  120
agatgtcagc aatttttagg ccacaatact gtttttctggt acagacagac catgatgcaa  180
ggactggagt tgctggctta cttccgcaac cgggctcctc tagatgattc ggggatgccg  240
aaggatcgat tctcagcaga gatgcctgat gcaactttag ccactctgaa gatccagccc  300
tcagaaccca gggactcagc tgtgtatttt tgtgctagtg gtttggt              347
```

<210> SEQ ID NO 131
<211> LENGTH: 374
<212> TYPE: DNA
<213> ORGANISM: Homo sapiens

<400> SEQUENCE: 131

```
atgcttagtc ctgacctgcc tgactctgcc tggaacacca ggctcctctg ccatgtcatg   60
ctttgtctcc tgggagcagt ttcagtggct gctggagtca tccagtcccc aagacatctg  120
atcaaagaaa agagggaaac agccactctg aaatgctatc ctatccctag acacgacact  180
gtctactggt accagcaggg tccaggtcag gaccccccagt tcctcatttc gttttatgaa  240
aagatgcaga gcgataaagg aagcatccct gatcgattct cagctcaaca gttcagtgac  300
tatcattctg aactgaacat gagctccttg gagctggggg actcagccct gtacttctgt  360
gccagcagct tagg                                                  374
```

<210> SEQ ID NO 132
<211> LENGTH: 347
<212> TYPE: DNA
<213> ORGANISM: Homo sapiens

<400> SEQUENCE: 132

```
atggtttcca ggcttctcag tttagtgtcc ctttgtctcc tgggagcaaa gcacatagaa   60
gctggagtta tcagttccc cagccacagc gtaatagaaa agggccagac tgtgactctg  120
agatgtgacc caatttctgg acatgataat ctttattggt atcgacgtgt tatgggaaaa  180
```

| | |
|---|---|
| gaaataaaat ttctgttaca ttttgtgaaa gagtctaaac aggatgagtc cggtatgccc | 240 |
| aacaatcgat tcttagctga aaggactgga gggacgtatt ctactctgaa ggtgcagcct | 300 |
| gcagaactgg aggattctgg agtttatttc tgtgccagca gccaaga | 347 |

<210> SEQ ID NO 133
<211> LENGTH: 344
<212> TYPE: DNA
<213> ORGANISM: Homo sapiens

<400> SEQUENCE: 133

| | |
|---|---|
| atgggtcctg ggcttctcca ctggatggcc cttttgtctcc ttggaacagg tcatggggat | 60 |
| gccatggtca tccagaaccc aagataccag gttacccagt ttggaaagcc agtgaccctg | 120 |
| agttgttctc agactttgaa ccataacgtc atgtactggt accagcagaa gtcaagtcag | 180 |
| gccccaaagc tgctgttcca ctactatgac aaagatttta acaatgaagc agacacccct | 240 |
| gataacttcc aatccaggag gccgaacact tctttctgct tcttgacat ccgctcacca | 300 |
| ggcctggggg acacagccat gtacctgtgt gccaccagca gaga | 344 |

<210> SEQ ID NO 134
<211> LENGTH: 347
<212> TYPE: DNA
<213> ORGANISM: Homo sapiens

<400> SEQUENCE: 134

| | |
|---|---|
| atgagcccaa tattcacctg catcacaatc ctttgtctgc tggctgcagg ttctcctggt | 60 |
| gaagaagtcg cccagactcc aaaacatctt gtcagagggg aaggacagaa agcaaaatta | 120 |
| tattgtgccc aataaaagg acacagttag gttttttggt accaacaggt cctgaaaaac | 180 |
| gagttcaagt tcttgatttc cttccagaat gaaaatgtct ttgatgaaac aggtatgccc | 240 |
| aaggaaagat tttcagctaa gtgcctccca aattcaccct gtagccttga gatccaggct | 300 |
| acgaagcttg aggattcagc agtgtatttt tgtgccagca gccaatc | 347 |

<210> SEQ ID NO 135
<211> LENGTH: 344
<212> TYPE: DNA
<213> ORGANISM: Homo sapiens

<400> SEQUENCE: 135

| | |
|---|---|
| atggatatct ggctcctctg ctgggtgacc ctgtgtctct tggcggcagg acactcggag | 60 |
| cctggagtca gccagacccc cagacacaag gtcaccaaca tgggacagga ggtgattctg | 120 |
| aggtgcgatc catcttctgg tcacatgttt gttcactggt accgacagaa tctgaggcaa | 180 |
| gaaatgaagt tgctgatttc cttccagtac caaaacattg cagttgattc agggatgccc | 240 |
| aaggaacgat tcacagctga agacctaac ggaacgtctt ccacgctgaa gatccatccc | 300 |
| gcagagccga gggactcagc cgtgtatctc tacagtagcg gtgg | 344 |

<210> SEQ ID NO 136
<211> LENGTH: 347
<212> TYPE: DNA
<213> ORGANISM: Homo sapiens

<400> SEQUENCE: 136

| | |
|---|---|
| atggacacca gagtactctg ctgtgcggtc atctgtcttc tggggcagg tctctcaaat | 60 |
| gccggcgtca tgcagaaccc aagacacctg gtcaggagga gggacagga ggcaagactg | 120 |
| agatgcagcc caatgaaagg acacagtcat gtttactggt atcggcagct cccagaggaa | 180 |

```
ggtctgaaat tcatggttta tctccagaaa gaaaatatca tagatgagtc aggaatgcca    240
aaggaacgat tttctgctga atttcccaaa gagggcccca gcatcctgag gatccagcag    300
gtagtgcgag gagattcggc agcttatttc tgtgccagct caccacc                  347
```

<210> SEQ ID NO 137
<211> LENGTH: 344
<212> TYPE: DNA
<213> ORGANISM: Homo sapiens

<400> SEQUENCE: 137

```
atgagcaacc aggtgctctg ctgtgtggtc ctttgtttcc tgggagcaaa caccgtggat    60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact ttcagaaagg agatatagct    240
gaagggtaca gcgtctctcg ggagaagaag gaatcctttc ctctcactgt gacatcggcc    300
caaaagaacc cgacagcttt ctatctctgt gccagtagta taga                     344
```

<210> SEQ ID NO 138
<211> LENGTH: 335
<212> TYPE: DNA
<213> ORGANISM: Homo sapiens

<400> SEQUENCE: 138

```
atgctgctgc ttctgctgct tctggggcca ggctccgggc ttggtgctgt cgtctctcaa    60
catccgagct gggttatctg taagagtgga acctctgtga agatcgagtg ccgttccctg    120
gactttcagg ccacaactat gttttggtat cgtcagttcc cgaaacagag tctcatgctg    180
atggcaactt ccaatgaggg ctccaaggcc acatacgagc aaggcgtcga aggacaag     240 tttctcatca accatgcaag cctgaccttg tccactctga cagtgaccag tgcccatcct   300
gaagacagca gcttctacat ctgcagtgct agaga                              335
```

<210> SEQ ID NO 139
<211> LENGTH: 347
<212> TYPE: DNA
<213> ORGANISM: Homo sapiens

<400> SEQUENCE: 139

```
atgggcacca ggctcctcgg ctgtgcagcc ctgtgtctcc tggcagcaga ctcttttcat    60
gccaaagtca cacagactcc aggacatttg gtcaaaggaa aaggacagaa aacaaagatg    120
gattgtaccc ccgaaaaagg acatactttt gtttattggt atcaacagaa tcagaataaa    180
gagtttatgc ttttgatttc ctttcagaat gaacaagttc ttcaagaaac ggagatgcac    240
aagaagcgat tctcatctca atgccccaag aacgcaccct gcagcctggc aatcctgtcc    300
tcagaaccgg gagacacggc actgtatctc tgcgccagca gtcaatc                 347
```

<210> SEQ ID NO 140
<211> LENGTH: 345
<212> TYPE: DNA
<213> ORGANISM: Homo sapiens

<400> SEQUENCE: 140

```
atggcctccc tgctcttctt ctgtggggcc ttttatctcc tgggaacagg gtccatggat    60
gctgatgtta cccagacccc aaggaatagg atcacaaaga caggaaagag gattatgctg    120
```

```
gaatgttctc agactaaggg tcatgataga atgtactggt atcgacaaga cccaggactg    180
ggcctacggt tgatctatta ctcctttgat gtcaaagata taaacaaagg agagatctct    240
gatggataca gtgtctctcg acaggcacag gctaaattct ccctgtccct agagtctgcc    300
atccccaacc agacagctct ttacttctgt gccaccagtg atttg                    345
```

<210> SEQ ID NO 141
<211> LENGTH: 344
<212> TYPE: DNA
<213> ORGANISM: Homo sapiens

<400> SEQUENCE: 141

```
atgactatca ggctcctctg ctacatgggc ttttattttc tggggcagg cctcatggaa      60 gctgacatct accagacccc aagatacctt gttataggga caggaaagaa gatcactctg    120
gaatgttctc aaaccatggg ccatgacaaa atgtactggt atcaacaaga tccaggaatg    180
gaactacacc tcatccacta ttcctatgga gttaattcca cagagaaggg agatctttcc    240
tctgagtcaa cagtctccag aataaggacg gagcattttc ccctgaccct ggagtctgcc    300
aggccctcac atacctctca gtacctctgt gccagcagtg aata                     344
```

<210> SEQ ID NO 142
<211> LENGTH: 344
<212> TYPE: DNA
<213> ORGANISM: Homo sapiens

<400> SEQUENCE: 142

```
atgggccccc agctccttgg ctatgtggtc ctttgccttc taggagcagg ccccctggaa      60
gcccaagtga cccagaaccc aagatacctc atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca agtctctcg aaaagagaag aggaatttcc ccctgatcct ggagtcgccc    300
agccccaacc agacctctct gtacttctgt gccagcagtt tatc                     344
```

<210> SEQ ID NO 143
<211> LENGTH: 344
<212> TYPE: DNA
<213> ORGANISM: Homo sapiens

<400> SEQUENCE: 143

```
atgggaatca ggctcctctg tcgtgtggcc ttttgtttcc tggctgtagg cctcgtagat      60
gtgaaagtaa cccagagctc gagatatcta gtcaaaagga cgggagagaa agtttttctg    120
gaatgtgtcc aggatatgga ccatgaaaat atgttctggt atcgacaaga cccaggtctg    180
gggctacggc tgatctattt ctcatatgat gttaaaatga agaaaaagg agatattcct    240 gaggggtaca gtgtctctag agagaagaag gagcgcttct ccctgattct ggagtccgcc    300
agcaccaacc agacatctat gtacctctgt gccagcagtt tatg                     344
```

<210> SEQ ID NO 144
<211> LENGTH: 335
<212> TYPE: DNA
<213> ORGANISM: Homo sapiens

<400> SEQUENCE: 144

```
atgctgagtc ttctgctcct tctcctggga ctaggctctg tgttcagtgc tgtcatctct      60
caaaagccaa gcagggatat ctgtcaacgt ggaacctccc tgacgatcca gtgtcaagtc    120
```

```
gatagccaag tcaccatgat gttctggtac cgtcagcaac ctggacagag cctgacactg   180
atcgcaactg caaatcaggg ctctgaggcc acatatgaga gtggatttgt cattgacaag   240
tttcccatca gccgcccaaa cctaacattc tcaactctga ctgtgagcaa catgagccct   300
gaagacagca gcatatatct ctgcagcgtt gaaga                              335

<210> SEQ ID NO 145
<211> LENGTH: 335
<212> TYPE: DNA
<213> ORGANISM: Homo sapiens

<400> SEQUENCE: 145
atgctctgct ctctccttgc ccttctcctg ggcactttct ttggggtcag atctcagact    60
attcatcaat ggccagcgac cctggtgcag cctgtgggca gcccgctctc tctggagtgc   120
actgtggagg gaacatcaaa ccccaaccta tactggtacc gacaggctgc aggcaggggc   180
ctccagctgc tcttctactc cgttggtatt ggccagatca gctctgaggt gcccccagaat   240 ctctcagcct ccagacccca ggaccggcag ttcatcctga ttctaagaa gctccttctc   300 agtgactctg gcttctatct ctgtgcctgg agtgt                              335

<210> SEQ ID NO 146
<211> LENGTH: 624
<212> TYPE: DNA
<213> ORGANISM: Artificial Sequence
<220> FEATURE:
<223> OTHER INFORMATION: DNA encoding soluble AH1.23 TCR alpha chain
      with introduced disulfide interchain bond

<400> SEQUENCE: 146
atgaaggagg tggagcagaa ttctggaccc ctcagtgttc cagagggagc cattgcctct    60
ctcaactgca cttacagtga ccgaggttcc cagtccttct tctggtacag acaatattct   120
gggaaaagcc ctgagttgat aatgttcata tactccaatg gtgacaaaga agatggaagg   180
tttacagcac agctcaataa agccagccag tatgtttctc tgctcatcag agactcccag   240
cccagtgatt cagccaccta cctctgtgcc gtgaaggggg ggtctggggg ttaccagaaa   300 gttaccttg gaactggaac aaagctccaa gtcatcccaa atatccagaa cccggatcct   360
gccgtgtacc agctgagaga ctctaaatcc agtgacaagt ctgtctgcct attcaccgat   420
tttgattctc aaacaaatgt gtcacaaagt aaggattctg atgtgtatat cacagacaaa   480
tgtgtgctag acatgaggtc tatggacttc aagagcaaca gtgctgtggc ctggagcaac   540
aaatctgact ttgcatgtgc aaacgccttc aacaacagca ttattccaga agacaccttc   600
ttccccagcc agaaagttc ctaa                                           624

<210> SEQ ID NO 147
<211> LENGTH: 735
<212> TYPE: DNA
<213> ORGANISM: Artificial Sequence
<220> FEATURE:
<223> OTHER INFORMATION: DNA encoding soluble AH1.23 TCR beta chain with
      introduced disulfide interchain bond

<400> SEQUENCE: 147
atgggcgtca tgcagaaccc aagacacctg gtcaggagga ggggacagga ggcaagactg    60
agatgcagcc aatgaaagg acacagtcat gtttactggt atcggcagct cccagaggaa   120
ggtctgaaat tcatggttta tctccagaaa gaaaatatca tagatgagtc aggaatgcca   180
```

```
aaggaacgat ttctgctga atttcccaaa gagggcccca gcatcctgag gatccagcag    240
gtagtgcgag gagattcggc agcttatttc tgtgccagct caccacagac aggggggcaca   300 gatacgcagt attttggccc aggcacccgg ctgacagtgc tcgaggacct gaaaaacgtg    360
ttcccacccg aggtcgctgt gtttgagcca tcagaagcag agatctccca cacccaaaag   420
gccacactgg tgtgcctggc cacaggcttc taccccgacc acgtggagct gagctggtgg   480
gtgaatggga aggaggtgca cagtggggtc tgcacagacc cgcagcccct caaggagcag   540
cccgccctca atgactccag atacgctctg agcagccgcc tgagggtctc ggccaccttc   600
tggcaggacc cccgcaacca cttccgctgt caagtccagt tctacgggct ctcggagaat   660
gacgagtgga cccaggatag ggccaaaccc gtcacccaga tcgtcagcgc cgaggcctgg   720
ggtagagcag actaa                                                    735

<210> SEQ ID NO 148
<211> LENGTH: 207
<212> TYPE: PRT
<213> ORGANISM: Artificial Sequence
<220> FEATURE:
<223> OTHER INFORMATION: Soluble AH1.23 TCR alpha chain with introduced
      disulfide interchain bond

<400> SEQUENCE: 148

Met Lys Glu Val Glu Gln Asn Ser Gly Pro Leu Ser Val Pro Glu Gly
 1               5                  10                  15

Ala Ile Ala Ser Leu Asn Cys Thr Tyr Ser Asp Arg Gly Ser Gln Ser
             20                  25                  30

Phe Phe Trp Tyr Arg Gln Tyr Ser Gly Lys Ser Pro Glu Leu Ile Met
         35                  40                  45

Phe Ile Tyr Ser Asn Gly Asp Lys Glu Asp Gly Arg Phe Thr Ala Gln
     50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val Lys Gly Gly Ser Gly
                 85                  90                  95

Gly Tyr Gln Lys Val Thr Phe Gly Thr Gly Thr Lys Leu Gln Val Ile
            100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
        195                 200                 205

<210> SEQ ID NO 149
<211> LENGTH: 244
<212> TYPE: PRT
<213> ORGANISM: Artificial Sequence
<220> FEATURE:
<223> OTHER INFORMATION: Soluble AH1.23 TCR beta chain with introduced
      disulfide interchain bond
```

```
<400> SEQUENCE: 149

Met Gly Val Met Gln Asn Pro Arg His Leu Val Arg Arg Arg Gly Gln
1               5                   10                  15

Glu Ala Arg Leu Arg Cys Ser Pro Met Lys Gly His Ser His Val Tyr
                20                  25                  30

Trp Tyr Arg Gln Leu Pro Glu Gly Leu Lys Phe Met Val Tyr Leu
            35                  40                  45

Gln Lys Glu Asn Ile Ile Asp Glu Ser Gly Met Pro Lys Glu Arg Phe
        50                  55                  60

Ser Ala Glu Phe Pro Lys Glu Gly Pro Ser Ile Leu Arg Ile Gln Gln
65                  70                  75                  80

Val Val Arg Gly Asp Ser Ala Ala Tyr Phe Cys Ala Ser Ser Pro Gln
                85                  90                  95

Thr Gly Gly Thr Asp Thr Gln Tyr Phe Gly Pro Gly Thr Arg Leu Thr
                100                 105                 110

Val Leu Glu Asp Leu Lys Asn Val Phe Pro Pro Glu Val Ala Val Phe
            115                 120                 125

Glu Pro Ser Glu Ala Glu Ile Ser His Thr Gln Lys Ala Thr Leu Val
        130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
        210                 215                 220

Gln Asp Arg Ala Lys Pro Val Thr Gln Ile Val Ser Ala Glu Ala Trp
225                 230                 235                 240

Gly Arg Ala Asp
```